Figure 1:
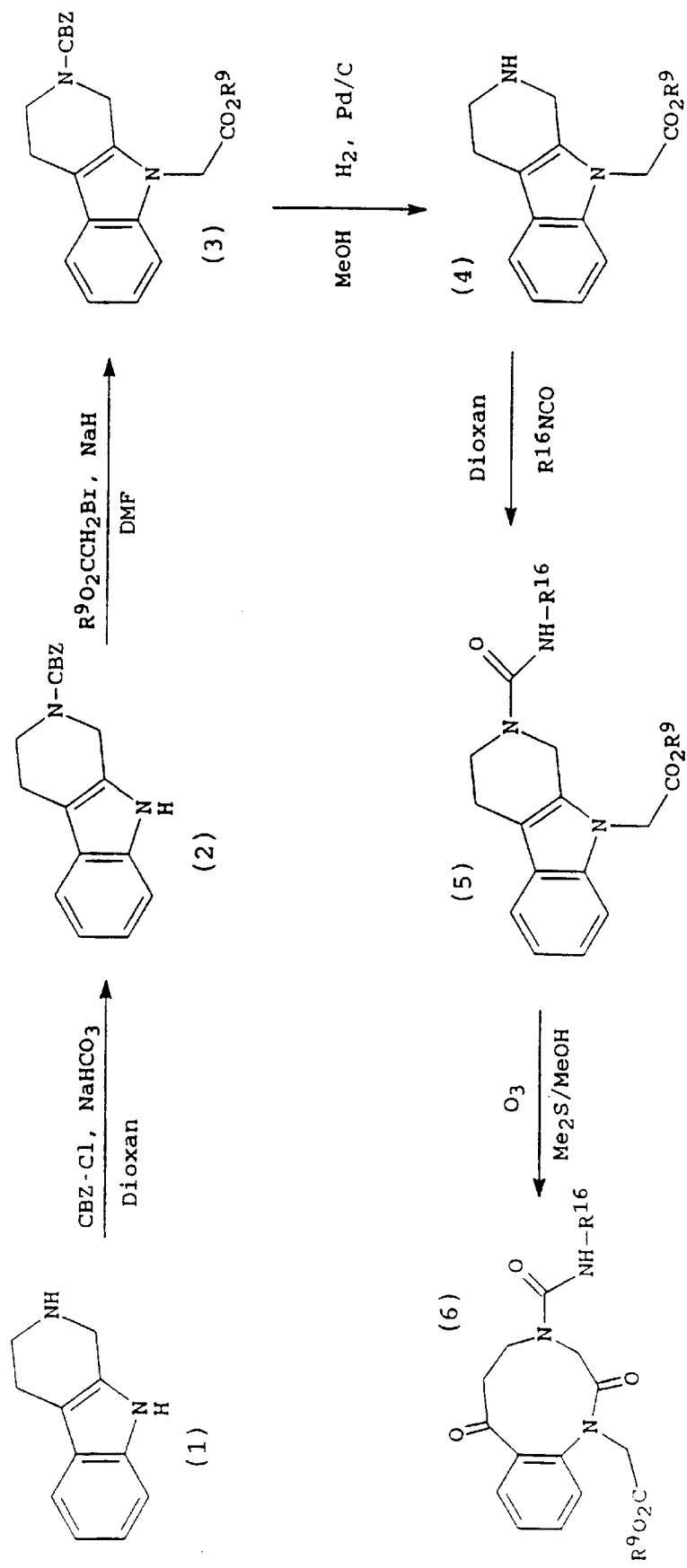

United States Patent [19]
Kalindjian et al.

[11] Patent Number: 6,057,311
[45] Date of Patent: May 2, 2000

[54] BENZODIAZONINE DERIVATIVES BINDING TO CHOLECYSTOKININ OR GASTRIN RECEPTORS

[75] Inventors: Sarkis Barret Kalindjian, Banstead; Iain Mair McDonald, Paddock Wood; Michael John Pether, Orpington; Caroline Minli Rachel Low, London; Katherine Isobel Mary Steel, Beckenham; Ian Duncan Linney, Guildford, all of United Kingdom

[73] Assignee: James Black Foundation Limited, London, United Kingdom

[21] Appl. No.: 09/142,533

[22] PCT Filed: Mar. 7, 1997

[86] PCT No.: PCT/GB97/00632

§ 371 Date: Oct. 26, 1998

§ 102(e) Date: Oct. 26, 1998

[87] PCT Pub. No.: WO97/32860

PCT Pub. Date: Sep. 12, 1997

[30] Foreign Application Priority Data

Mar. 8, 1996 [GB] United Kingdom ................... 9604996

[51] Int. Cl.[7] ..................... A61K 31/395; C07D 245/06; C07D 255/04
[52] U.S. Cl. ........................... 514/183; 540/460; 540/461
[58] Field of Search ..................... 540/460, 461; 514/183

[56] References Cited

U.S. PATENT DOCUMENTS 5,206,234  4/1993  Bock et al. .............................. 514/213

OTHER PUBLICATIONS

Kikugawa et al. (J. Chem. Soc., Chem. Commun. (1991), (19), 1354–5), 1991.

*Primary Examiner*—Richard L. Raymond
*Assistant Examiner*—Bruck Kifle
*Attorney, Agent, or Firm*—Foley & Lardner

[57] ABSTRACT

Compounds of the formula

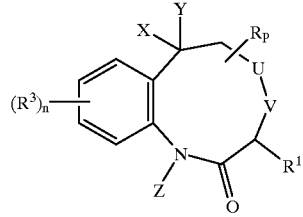

(I)

wherein
one of U and V is —$CHR^2$—, and the other of U and V is selected from —$N(COR^4)$—, —$CH(COR^4)$—, —$N(SO_2R^4)$— and —$CH(SO_2R^4)$—,
and pharmaceutically acceptable salts thereof are ligands at gastrin and/or cholecystokinin receptors.

34 Claims, 11 Drawing Sheets

BENZODIAZONINE DERIVATIVES BINDING TO CHOLECYSTOKININ OR GASTRIN RECEPTORS

This application is a 371 of PCT/GB97/00632, filed Mar. 7, 1997.

This invention relates to benzodiazonine derivatives, and more particularly to benzodiazonine derivatives which bind to cholecystokinin and/or gastrin receptors. The invention also relates to methods for preparing such benzodiazonine derivatives.

Gastrin and the CCK's are structurally-related neuropeptides which exist in gastrointestinal tissue and in the CNS (see Mutt V., *Gastrointestinal Hormones*, Glass G. B. J., ed., Raven Press, N. Y., p. 169 and Nisson G., ibid, p. 127).

Gastrin is one of the three primary stimulants of gastric acid secretion. Several forms of gastrin are found including 34-, 17-, and 14-amino acid species with the minimum active fragment being the C-terminal tetrapeptide (TrpMetAspPhe-NH$_2$) which is reported in the literature to have full pharmacological activity (see Tracey H. J. and Gregory R. A., Nature (London), 1964, 204, 935). Much effort has been devoted to the synthesis of analogues of this tetrapeptide (and the N-protected derivative Boc-TrpMetAspPhe-NH$_2$) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

Members of this family of hormones are reported to be important in the regulation of appetite. They stimulate intestinal motility, gall bladder contraction, pancreatic enzyme secretion, and are known to have a trophic action on the pancreas. They also inhibit gastric emptying and have various effects in the CNS.

Compounds which bind to cholecystokinin and/or gastrin receptors are important because of their potential pharmaceutical use as antagonists of the natural peptides. A number of gastrin antagonists have been proposed for various therapeutic applications, including the prevention of gastrin-related disorders, gastrointestinal ulcers, Zollinger-Ellison syndrome, antral G Cell hyperplasia and other conditions in which lowered gastrin activity is desirable. The hormone has also been shown to have a trophic action on cells of the gastrointestinal tract and so an antagonist may be expected to be useful in the treatment of cancers, particularly in the stomach.

Possible therapeutic uses for gastrin and cholecystokinin antagonists include the control of appetite disorders such as anorexia nervosa, and the treatment of pancreatic inflammation, biliary tract disease and various psychiatric disorders. Other possible uses are in the potentiation of opiate (e.g. morphine) analgesia, and in the treatment of cancers, especially of the pancreas. Moreover, ligands for gastrin/cholecystokinin receptors in the brain (so-called $CCK_B$ receptors) have been claimed to possess anxiolytic activity.

U.S. Pat. No. 5,206,234 discloses certain benzolactam analogs which are said to be antagonists of gastrin and CCK.

According to the present invention, there are provided compounds of the formula

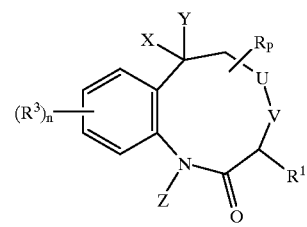

(I)

wherein one of U and V is —$CHR^2$—, and the other of U and V is selected from —$N(COR^4)$—, —$CH(COR^4)$—, —$N(SO_2R^4)$— and —$CH(SO_2R^4)$—, in which
  $R^2$ is H, —$COOR^5$ (wherein $R^5$ is H or $C_1$ to $C_4$ hydrocarbyl), —$CONR^6R^7$ (wherein $R^6$ is H or methyl and $R^7$ is aryl, substituted aryl, or a group of the formula —($C_1$ to $C_4$)alkylene-W, in which W is amidino, hydroxy, acyloxy, sulphamoyl, hydroxysulphonyl, carboxy, esterified carboxy, amidated carboxy, tetrazolyl, hydroxamyl, $R^{14}$—$SO_2$—NH—, $R^{14}$—$SO_2$—NH—CO—, $R^{14}$—$SO_2$—, $R^{14}$—SO—, $R^{14}$—CO—, $R^{14}$—CO—NH—, $R^{14}$—CO—NH—SO—, $R^{14}$—CO—NH—$SO_2$—, or $R^{15}$—NH—$SO_2$— wherein $R^{14}$ is H (except when $R^{14}$ is attached to a sulphur atom), $C_1$ to $C_6$ alkyl, $C_1$ to $C_6$ haloalkyl, aryl or substituted aryl, and $R^{15}$ is H, $C_1$ to $C_6$ alkyl, $C_1$ to $C_6$ haloalkyl, aryl, substituted aryl, —OH or —CN; or $R^6$ and $R^7$ together form a carboxy-substituted propylene, butylene or pentylene group) or —$COR^7$ (wherein $R^7$ is as defined above); and
  $R^4$ is H, $C_1$ to $C_6$ hydrocarbyl (in which up to three of the carbon atoms may be replaced by a nitrogen, oxygen or sulphur atom, provided that $R^4$ does not contain a —O—O— group), or a group of the formula —Q—$R^{16}$ wherein Q is a bond, —$NR^{17}$— (in which $R^{17}$ is H or $C_1$ to $C_3$ alkyl) or —O—, and $R^{16}$ is aryl, substituted aryl, arylalkyl or (substituted aryl)alkyl;

R is independently $C_1$ to $C_3$ alkyl, $R^1$ is H or $C_1$ to $C_{15}$ hydrocarbyl wherein one or more hydrogen atoms may be replaced by halogen atoms, and one carbon atom may be replaced by a nitrogen, oxygen or sulphur atom;

$R^3$ is independently halo, alkyl, alkoxy, —$NO_2$, —$NH_2$ or —$NHCOR^5$ (wherein $R^5$ is as defined above);

X is H and Y is H or $C_1$ to $C_{10}$ hydrocarbyl wherein one or more hydrogen atoms may be replaced by halogen atoms, and one carbon atom may be replaced by a nitrogen, oxygen or sulphur atom; or X and Y together are =O or =$CH_2$;

Z is H, $C_1$ to $C_{15}$ hydrocarbyl (in which one or more hydrogen atoms may be replaced by a halogen atom, and up to three of the carbon atoms may be replaced by a nitrogen, oxygen or sulphur atom, provided that Z does not contain a —O—O— group) or —$(CHR^{18})_m$—$R^8$ (wherein $R^{18}$ is H or $C_1$ to $C_3$ alkyl and $R^8$ is phenyl, substituted phenyl or a group of the formula —$COOR^9$ or —$CONR^9R^{10}$, in which $R^9$ and $R^{10}$ are independently H or $C_1$ to $C_6$ alkyl, or $R^9$ and $R^{10}$ together form a propylene, butylene, pentylene or hexylene group);

m is from 1 to 3; and n and p are independently from 0 to 3, and pharmaceutically acceptable salts thereof.

Preferably, U is —CHR$^2$— and V is —N(COR$^4$)—.

The term "hydrocarbyl", as used herein, refers to monovalent groups consisting of carbon and hydrogen. Hydrocarbyl groups thus include alkyl, alkenyl, and alkynyl groups (in both straight and branched chain forms), cycloalkyl (including polycycloalkyl), cycloalkenyl, and aryl groups, and combinations of the foregoing, such as alkylaryl, alkenylaryl, alkynylaryl, cycloalkylaryl, and cycloalkenylaryl groups, A "carbocyclic" group, as the term is used herein, comprises one or more closed chains or rings, which consist entirely of carbon atoms. Included in such groups are alicyclic groups (such as cyclopropyl, cyclobutyl, cyclopentyl, cyclohexyl and adamantyl), groups containing both alkyl and cycloalkyl moieties (such as adamantanemethyl), and aromatic groups (such as phenyl, naphthyl, indanyl, fluorenyl, (1,2,3,4)-tetrahydronaphthyl, indenyl and isoindenyl).

The term "aryl" is used herein to refer to aromatic carbocyclic groups, including those mentioned above.

A "heterocyclic" group comprises one or more closed chains or rings which have at least one atom other than carbon in the closed chain or ring. Examples include benzimidazolyl, thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

The terms "halogen" and "halo", as used herein, refer to any of fluorine, chlorine, bromine and iodine. Most usually, however, halogen substituents in the compounds of the invention are chlorine or fluorine substituents. When R$^{14}$ or R$^{15}$ is a substituted aryl group, the substituents are preferably from one to three (usually one) in number and are preferably selected from the groups recited above for R$^3$. When R$^7$ is a substituted aryl group or R$^8$ is a substituted phenyl group, the substituents are preferably from one to three (usually one) in number and are preferably selected from the groups recited above for R$^3$ or carboxyl. When R$^{16}$ is a substituted aryl group, the substituents are preferably from one to three (usually one) in number and are preferably selected from the groups recited above for R$^3$ or W.

When R$^3$ is an alkyl or alkoxy group, or R$^{16}$ contains an alkylene group, such groups generally contain from 1 to 6 carbon atoms, and more usually from 1 to 3 carbon atoms.

Preferably, R$^1$ is H, C$_1$ to C$_6$ alkyl or cycloalkyl-(C$_1$ to C$_6$)alkyl. For example, R$^1$ may be H, t-butylmethyl, cycloheptylmethyl or (1-adamantyl)methyl.

R$^4$ is preferably H, methyl, methoxy, carboxymethylene, carboxyethylene, benzyloxy or a group of the formula —NH-Ar (wherein Ar is an aromatic group such as methylphenyl, carboxyphenyl, dicarboxyphenyl, dichlorophenyl, naphthyl or indolyl).

When R$^8$ is substituted phenyl, the (or each) substituent is preferably selected from the groups recited above for R$^3$ and W. For example, the (or each) substituent may be selected from chloro, methoxy and amino.

R$^8$ is preferably t-butyloxycarbonyl, ethoxycarbonyl, pyrrolidinoyl, phenyl, 3-methoxyphenyl, 4-methoxyphenyl, 3-chlorophenyl, 4-chlorophenyl or 3-aminophenyl.

When X is H, Y is preferably H, —OH or —CH$_3$.

The invention also comprehends derivative compounds ("pro-drugs") which are degraded in vivo to yield the species of formula (I). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al, "Prodrugs", *Drug Delivery Systems*, pp. 112–176 (1985), and *Drugs*, 29, pp. 455–473 (1985).

Pro-drug forms of the pharmacologically-active compounds of the invention will generally be compounds according to formula (I) in which free acid groups have been esterified or amidated. Included in such esterified acid groups are groups of the form —COOR$^{11}$, wherein R$^{11}$ is C$_1$ to C$_5$ alkyl, phenyl, substituted phenyl, benzyl, substituted benzyl, or one of the following:

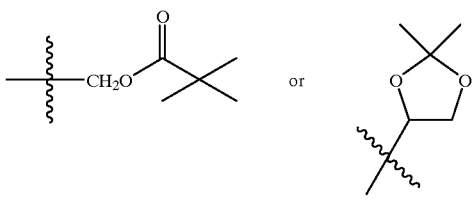

Amidated acid groups include groups of the formula —CONR$^{12}$R$^{13}$, wherein R$^{12}$ is H, C$_1$ to C$_5$ alkyl, phenyl, substituted phenyl, benzyl, or substituted benzyl, and R$^{13}$ is —OH or one of the groups just recited for R$^{12}$.

Pharmaceutically acceptable salts of the acidic compounds of the invention include salts with alkali metals and alkaline earth metals, such as sodium, potassium, calcium and magnesium, and salts with organic bases. Suitable organic bases include amines such as N-methyl-D-glucamine.

Pharmaceutically acceptable salts of the basic compounds of the invention include salts derived from organic or inorganic acids. Suitable acids include hydrochloric acid, phosphoric acid, oxalic acid, maleic acid, succinic acid and citric acid.

The compounds of the invention exist in various enantiomeric and diastereomeric forms. It will be understood that the invention comprehends the different enantiomers and diastereomers in isolation from each other, as well as mixtures of enantiomers and diastereomers.

FIGS. 1 to 12 depict reaction schemes which may be employed to prepare compounds according to the invention.

The reaction scheme illustrated in FIG. 1 is suitable for preparing compounds (such as the compound of Example 1), in which Z is a group of the formula —CH$_2$COOR$^9$. 1,2,3,4-Tetrahydro-9H-pyrido[3,4-b]indole (1) is first reacted with benzylchloroformate, or other suitable reagent, to protect the nitrogen atom of the piperidine moiety. The partially N-protected product (2) is then admixed with sodium hydride in a suitable solvent (such as DMF), and a bromoacetic acid ester is then added to form compound (3). The nitrogen atom of the piperidine moiety of compound (3) is then deprotected (e.g. by hydrogenation over palladium/charcoal), and the resulting product (4) is then reacted with an isocyanate (R$^{16}$NCO). The product (5) of this reaction is dissolved in a suitable solvent (such as methanol), and ozone is bubbled through the solution to form the desired product (6).

Figure 2:
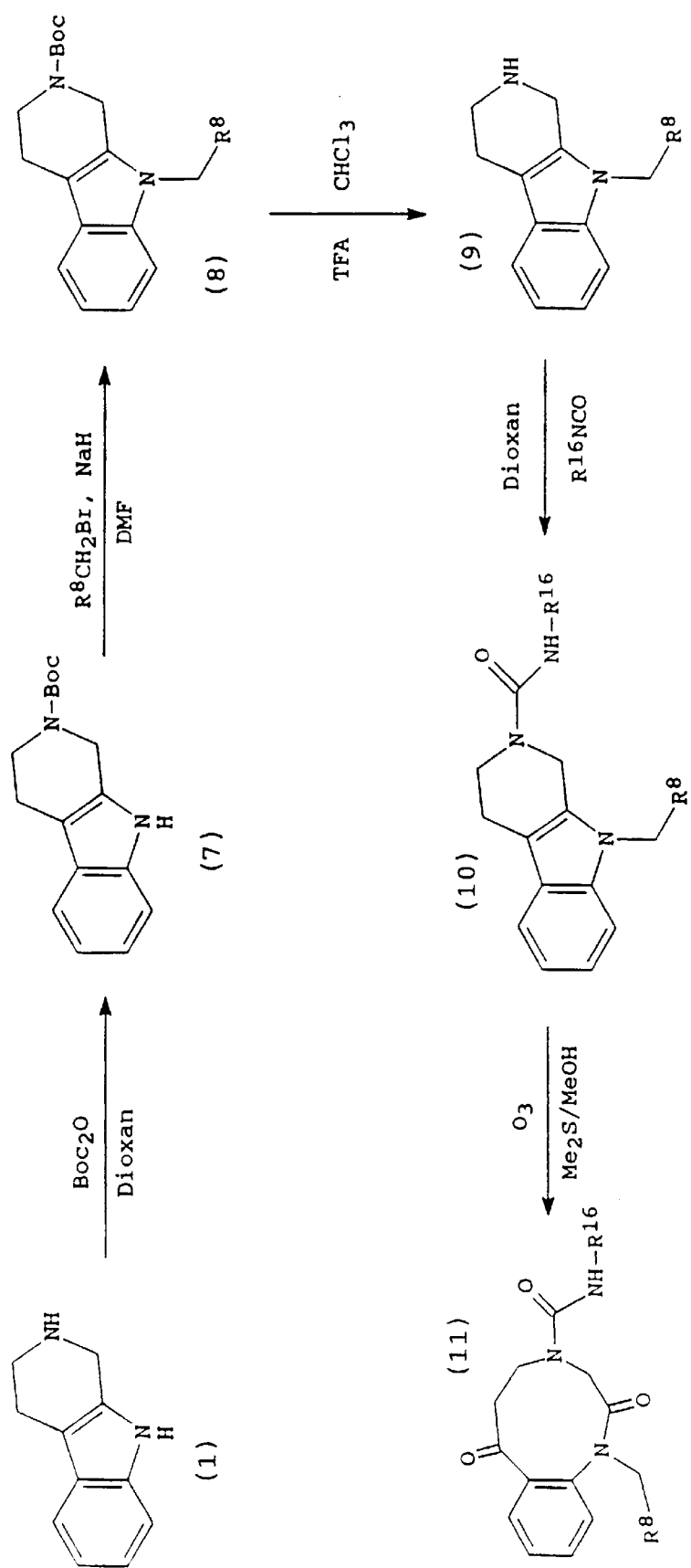

FIG. 2 illustrates a reaction scheme which is suitable for preparing compounds in which Z is benzyl or substituted benzyl. In this case, the nitrogen atom of the piperidine moiety of compound (1) is protected using a reagent such as di-t-butyl dicarbonate, and the partially N-protected product (7) is reacted with sodium hydride and benzyl bromide or a substituted benzyl bromide. The reaction product (8) is then deprotected using trifluoroacetic acid to form compound (9). This is then reacted with an isocyanate and then with ozone, in a manner analogous to that described above in connection with FIG. 1.

Figure 3:
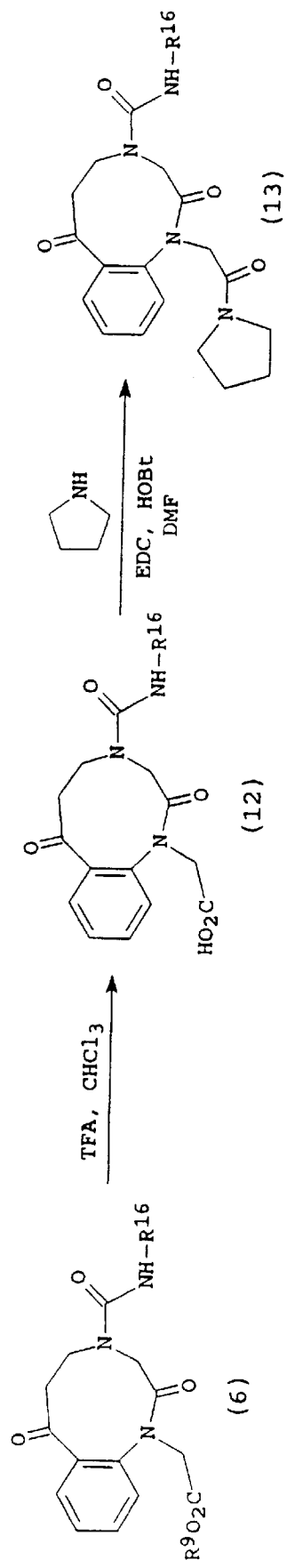

Compounds in which Z is a pyrrolidinoylmethyl group may be prepared by the reaction scheme which is depicted in FIG. 3. Compound (6), which may be prepared as shown in FIG. 1, is treated with trifluoroacetic acid to yield the carboxylic acid derivative (12). This is then reacted with pyrrolidine to form the desired compound (13).

Figure 4:
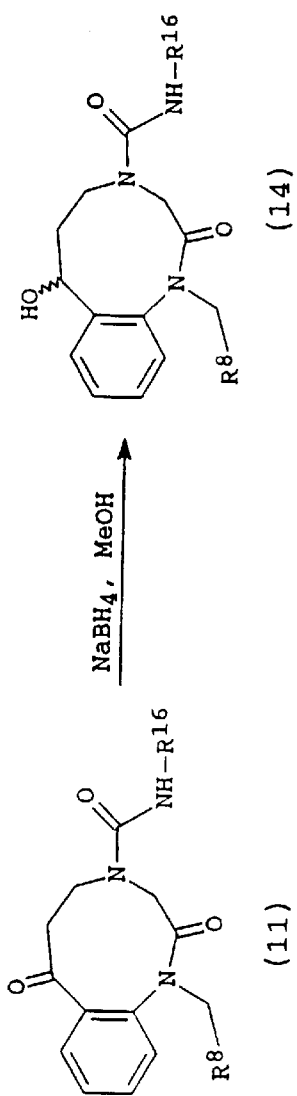

Compounds in which X is hydrogen and Y is —OH may be obtained by the reaction which is illustrated in FIG. 4. In this case, compound (11), obtained by the reaction scheme illustrated in FIG. 2, is treated with sodium borohydride to produce the desired derivative (14).

Figure 5:
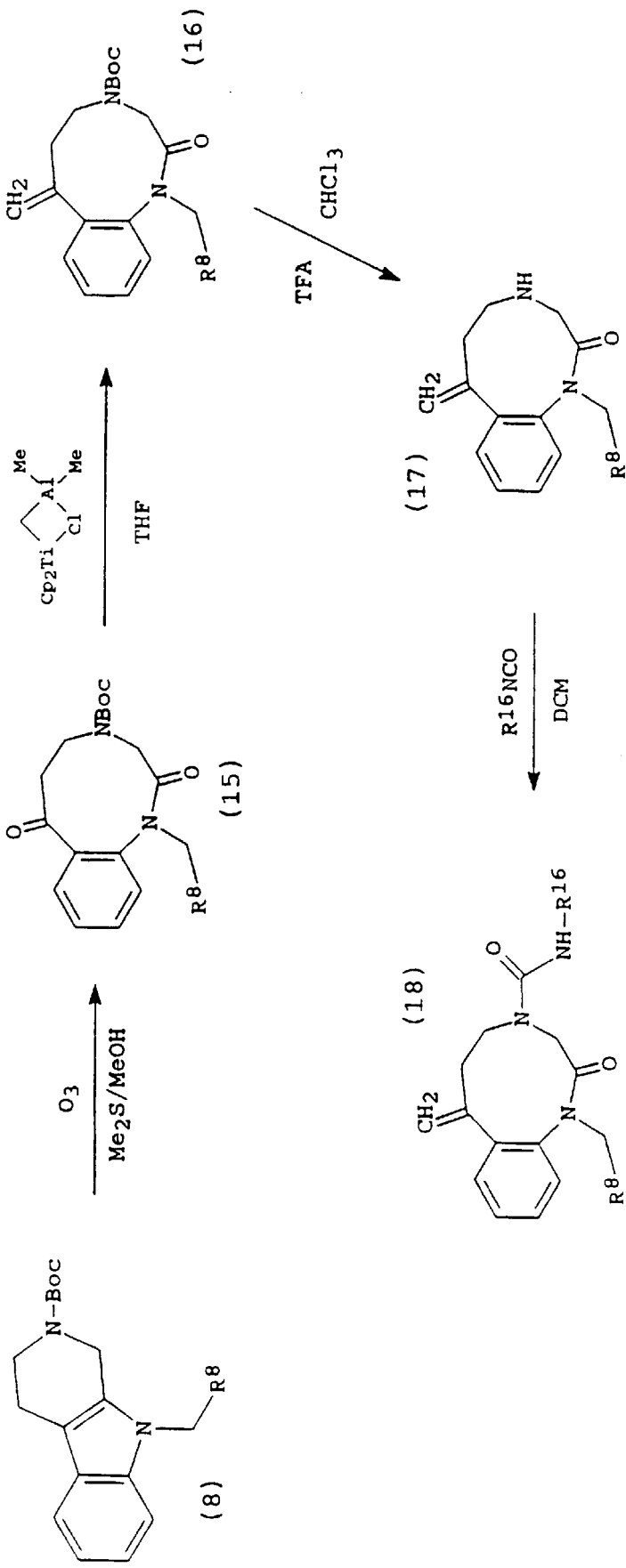

Compounds according to the invention in which X and Y together form a methylene group may be obtained by the reaction scheme illustrated in FIG. 5. Compound (8), obtained as an intermediate in the reaction scheme shown in FIG. 2, is treated with ozone to provide the benzodiazonine (15). $\mu$-Chloro-$\mu$-methylene-[bis(cyclopentadienyl) titanium]dimethylaluminium is then added to a solution of the compound (15) to form compound (16). The N-protecting group is then removed using trifluoroacetic acid to form compound (17). This is then reacted with an isocyanate to produce the desired compound (18).

Figure 6:
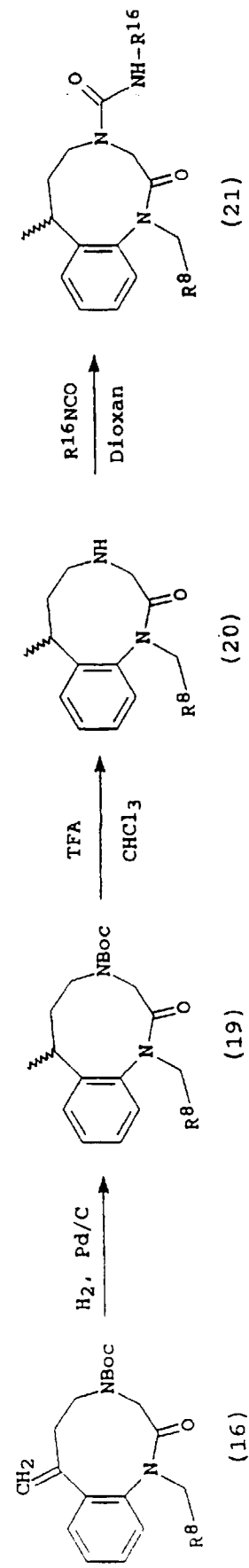

Compounds in which X is H and Y is —CH$_3$ may be prepared by the reaction scheme illustrated in FIG. 6. In this scheme, compound (16), which is formed as an intermediate in the reaction scheme illustrated in FIG. 5, is reduced by hydrogenation over palladium on charcoal to form compound (19). The N-protecting group is then removed using trifluoroacetic acid, and the resulting compound (20) is then reacted with an isocyanate in a manner analogous to that shown in FIG. 5.

Figure 7:
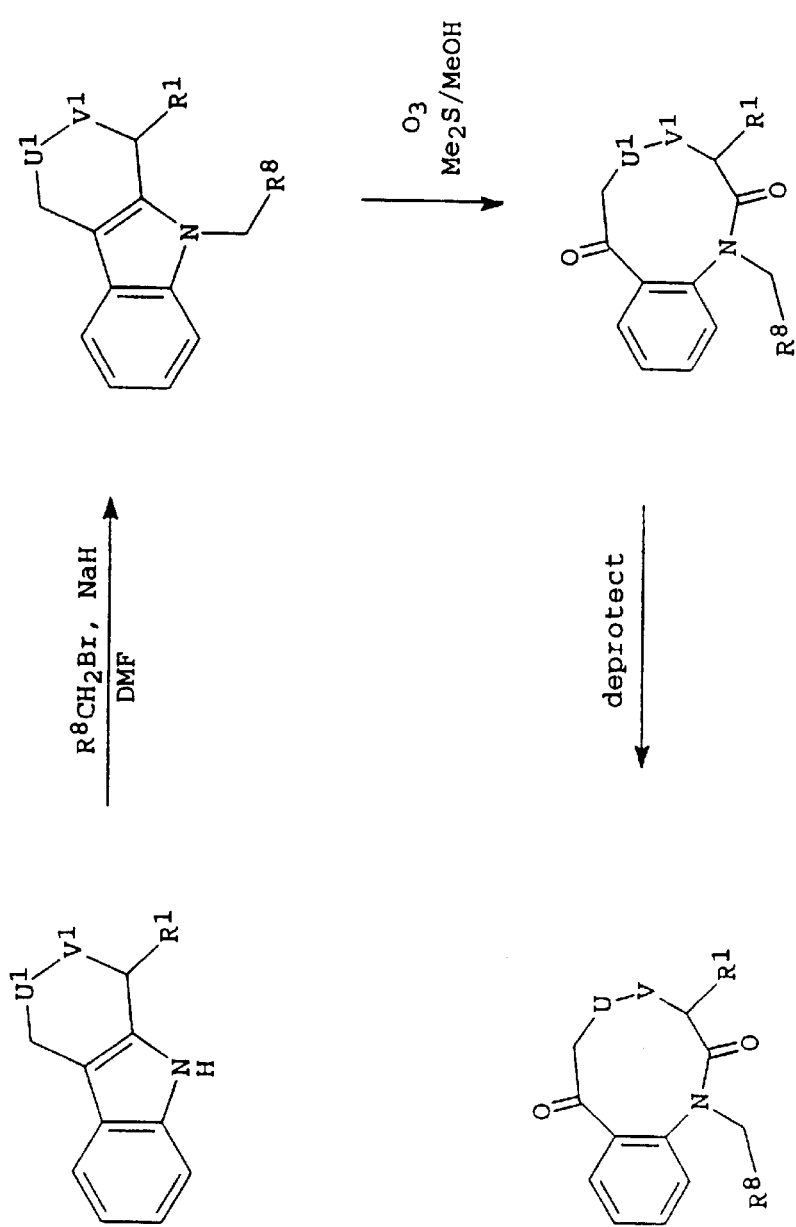

FIG. 7 illustrates a general scheme whereby compounds of the invention in which R$^1$ and R$^2$ are other than hydrogen may be prepared from various tetrahydrocarbolines and 1,2,3,4-tetrahydrocarbazoles. In FIG. 7, U$^1$ and V$^1$ represent the groups defined above for U and V, respectively, or suitably protected derivatives thereof.

Figure 8:
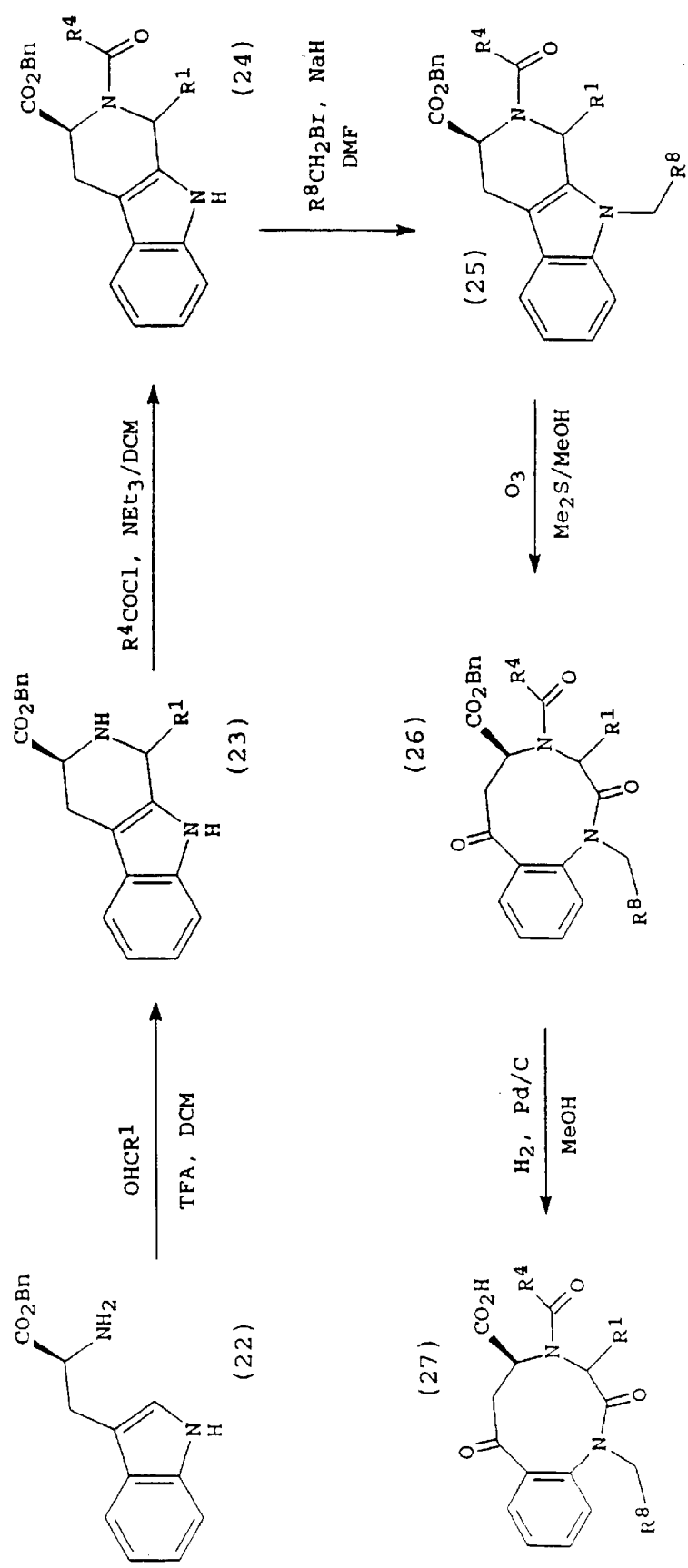

The general scheme shown in FIG. 7 is exemplified in FIG. 8 for the case in which U is —CH(CO$_2$H)— and V is —N(COR$^4$)—. The L-tryptophan ester (22) is reacted with an aldehyde to form the 1,2,3,4-tetrahydro-9H-pyrido[3,4-b]indole derivative (23). This is then reacted with an acid chloride to form compound (24), and this in turn is reacted with benzyl bromide (or a substituted benzyl bromide) to form derivative (25). This is then reacted with ozone to form the benzodiazonine (26), and the 5-carboxyl group is then deprotected by catalytic hydrogenation to yield the desired compound (27).

Figure 9:
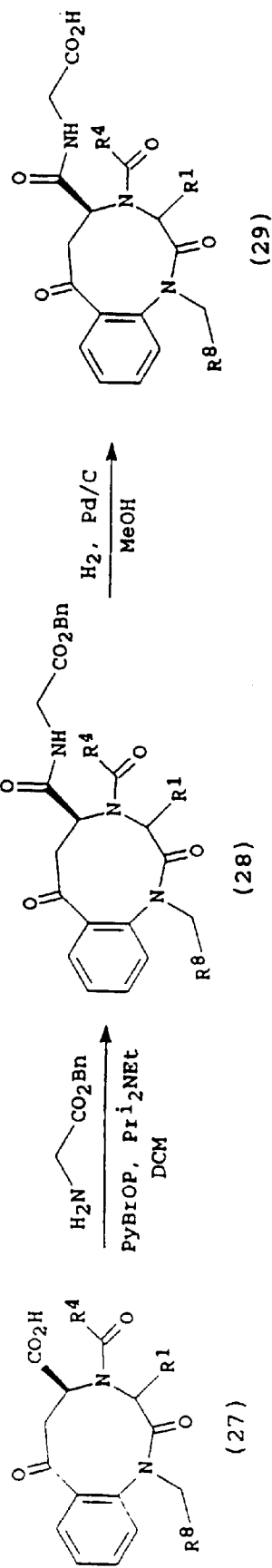

Compound (27) may be used to provide further derivatives, as shown in FIG. 9. For example, the 5-carboxyl group may be reacted with an amine (such as glycine benzyl ester p-toluene sulphonate) to form the amide (28). This is then subjected to catalytic hydrogenation to yield the free acid compound (29).

Figure 10:
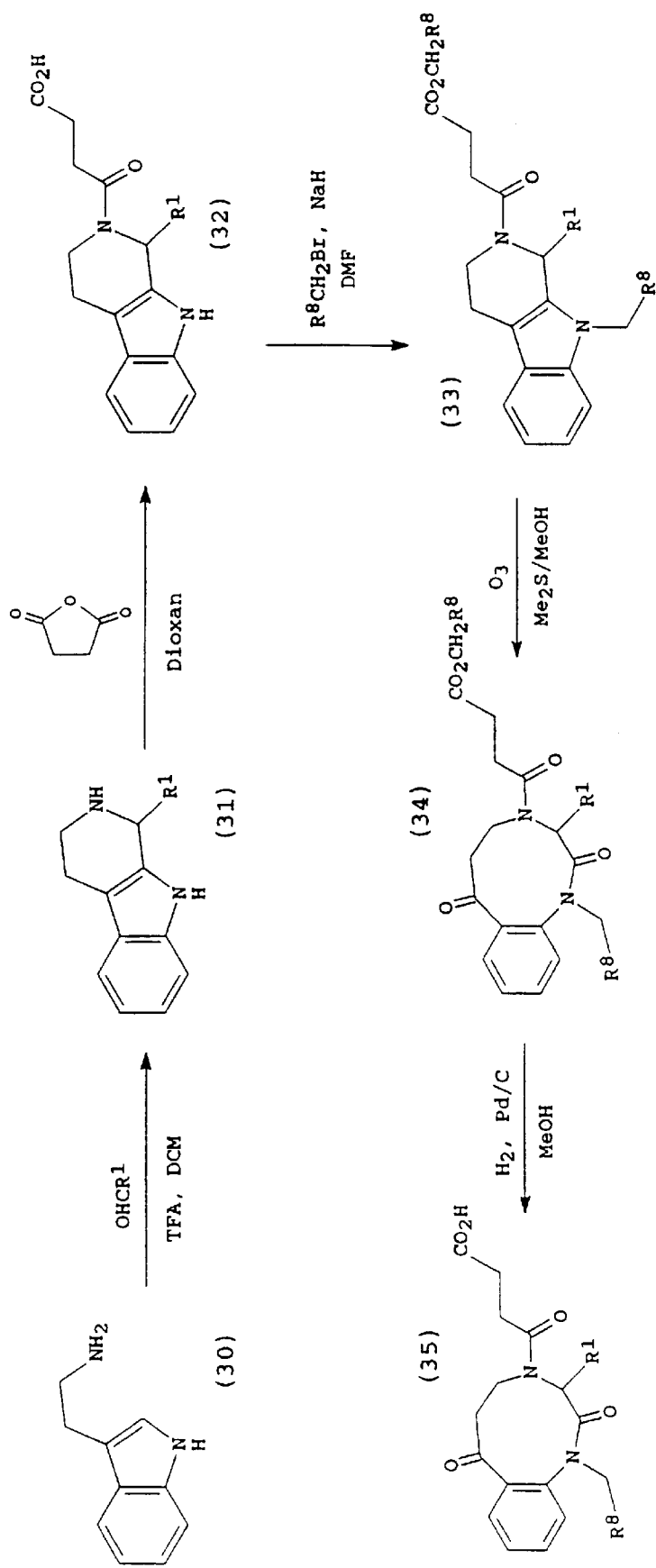

Compounds in which R$^1$ is other than hydrogen may also be formed by means of a reaction scheme such as that illustrated in FIG. 10. Tryptamine (30) is reacted with an aldehyde to form the substituted 1,2,3,4-tetrahydro-9H-pyrido[3,4-b]indole (31). Reaction of this compound with succinic anhydride yields the compound (32), which is then reacted with benzyl bromide (or a substituted benzyl bromide) to form compound (33). This is then reacted with ozone to form the benzodiazonine (34), which in turn is treated with hydrogen over a palladium on charcoal catalyst to yield the desired compound (35).

Figure 11:
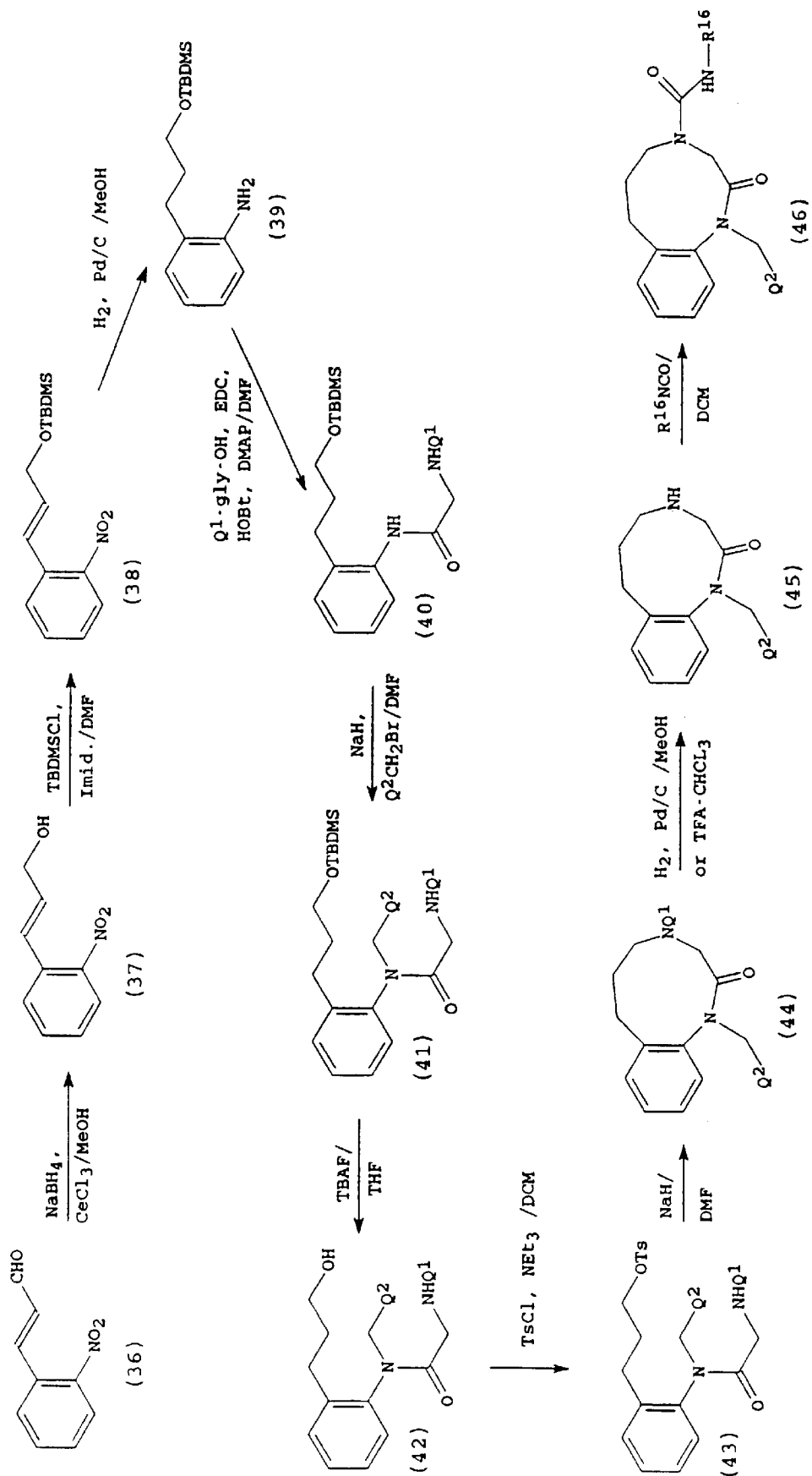

Compounds in which R$^4$ is a group of the formula —NH—R$^{16}$ may be obtained by means of the reaction scheme illustrated in FIG. 11. In this scheme, trans-2-nitrocinnamaldehyde (36) is reduced to 2-nitrocinnamyl alcohol (37), such as by adding sodium borohydride to a solution of trans-2-nitrocinnamaldehyde and cerium (III) chloride in methanol. The free hydroxyl group is then protected (eg. by means of tert-butyldimethylchlorosilane and imidazole in DMF) before being reduced to the protected aniline derivative (39). The latter is then reacted with a glycine derivative of the formula Q$^1$-gly-OH (in which Q$^1$ represents a suitable protecting group) to form compound (40). After reaction with sodium hydride, the product is then treated with a compound of formula Q$^2$CH$_2$Br, in which Q$^2$ represents a suitably protected derivative of the group R$^8$, yielding the compound (41). This in turn is deprotected (eg. with tetrabutyl ammonium fluoride in THF) to form the 2-(3-hydroxypropyl)aniline derivative (42). This compound is then tosylated and the product (43) is treated with sodium hydride to form the benzodiazonine (44). Compound (45) may be obtained by catalytic hydrogenation or treatment of (44) with trifluoroacetic acid, and the ring nitrogen atom may then be functionalised by reaction with an isocyanate of the formula R$^{16}$NCO.

Figure 12:
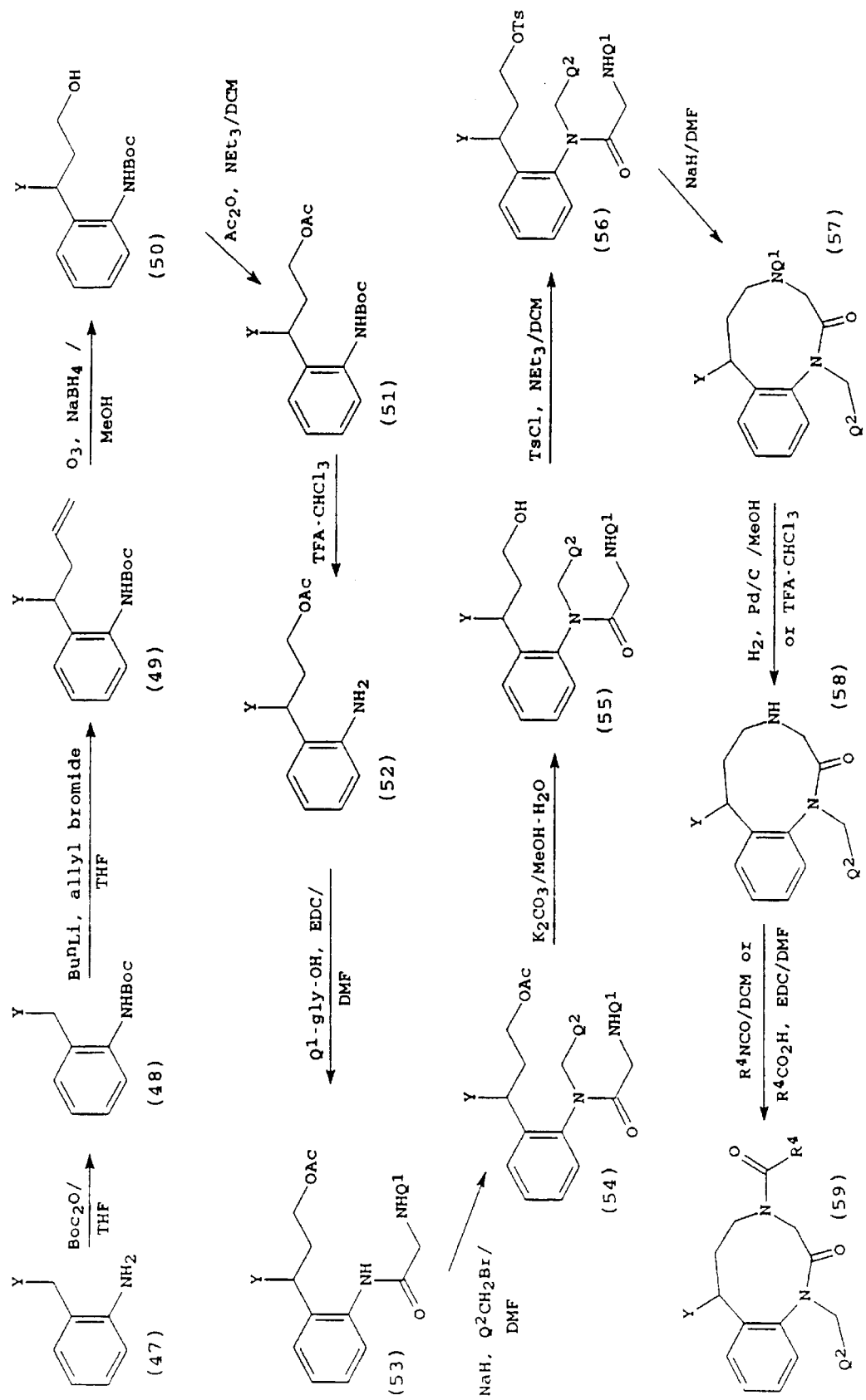

FIG. 12 provides an alternative route to compounds of the invention in which X is H. The aniline derivative (47) is protected (eg. with di-tert-butyldicarbonate), and then reacted with n-butyl lithium and allyl bromide to form compound (49). This is then oxidised (eg. by treatment with ozone, followed by sodium borohydride) to form the alcohol (50). Protection of the free hydroxyl group and deprotection of the amino group gives the aniline derivative (52). This compound is then reacted with the glycine derivative Q$^1$-gly-OH, and the product (53) is treated with sodium hydride and then with a compound of formula Q$^2$CH$_2$Br. After appropriate deprotection (55) and tosylation (56), the benzodiazonine compounds of the invention are obtained by steps analogous to those shown in FIG. 11.

In a further aspect, therefore, the invention also provides a method of preparing a compound according to formula (I) above, said method including the step of reacting a compound of the formula

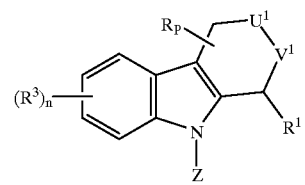

with an oxidant such as ozone to form a compound of the formula

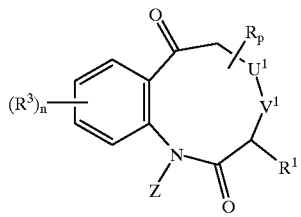

Also provided is a method of preparing a compound according to formula (I) above in which X is H and Y is —OH, said method comprising reducing a compound of the formula

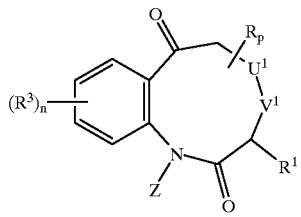

The invention additionally provides a method of preparing a compound according to formula (I) above in which X is H and Y is —CH$_3$, said method comprising reducing a compound of the formula

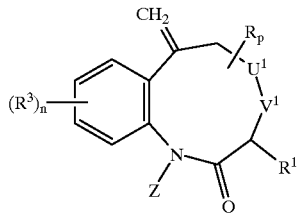

Further provided is a method of preparing a compound according to formula (I) above wherein X and Y together form a methylene group, said method comprising the step of reacting a compound of formula

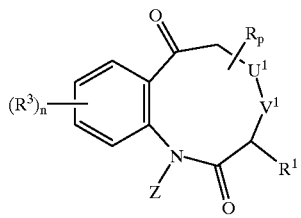

with μ-chloro-μ-methylene-[bis(cyclopentadienyl)titanium] dimethylaluminium.

In a still further aspect, the invention provides a method of preparing a compound according to formula I above, said method comprising the step of reacting a compound of the formula

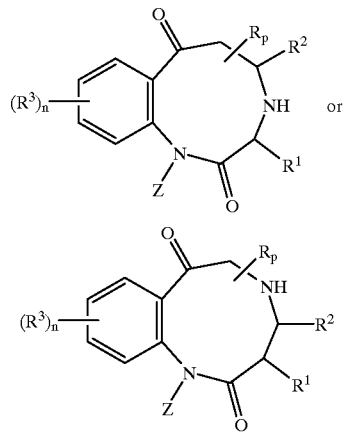

with an isocyanate of the formula R$^{16}$NCO or a carboxylic acid of the formula R$^4$COOH.

Pharmaceutically acceptable salts of the acidic or basic compounds of the invention can of course be made by conventional procedures, such as by reacting the free base or acid with at least a stoichiometric amount of the desired salt-forming acid or base.

The compounds of the invention can be administered by oral or parenteral routes, including intravenous, intramuscular, intraperitoneal, subcutaneous, rectal and topical administration.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including the severity of the condition being treated, the route of administration and the weight of the patient. In general, however, the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be between 0.01 μg/kg and 50 mg/kg, especially between 10 μg/kg and 10 mg/kg, eg. between 100 μg/kg and 2 mg/kg.

The compounds of the following examples were prepared by the synthetic routes outlined in FIGS. 1 to 12. The structures of the title compounds are set out below:

Ex. 1
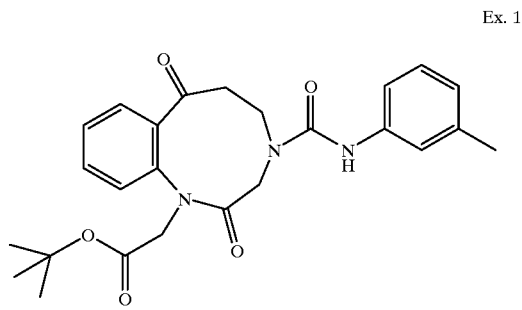

Ex. 2
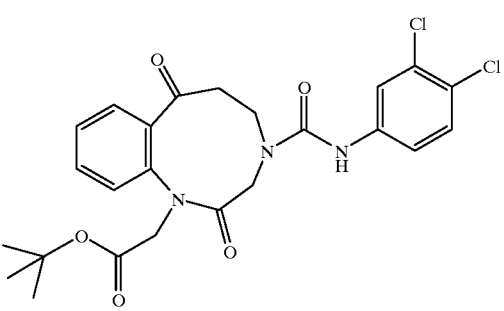

Ex. 3
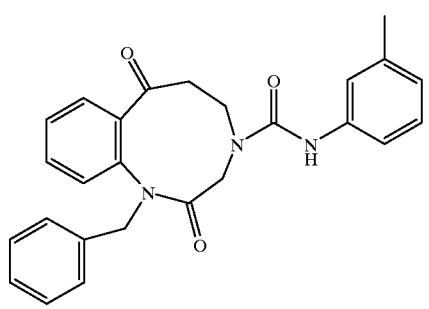

Ex. 4
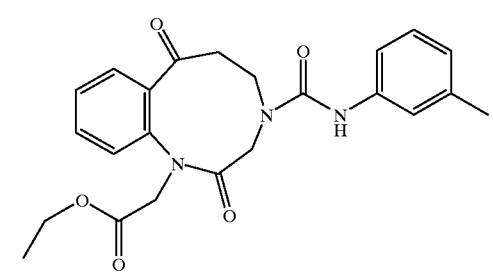

-continued

Ex. 5
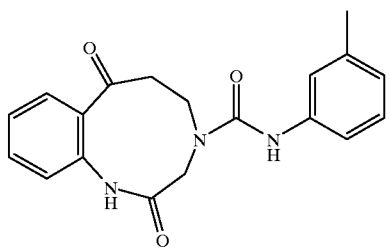

Ex. 6
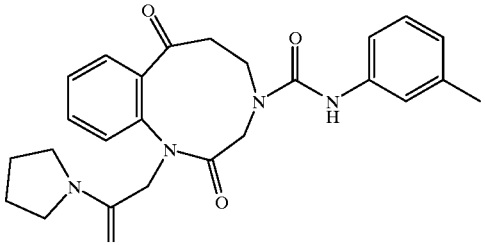

Ex. 7
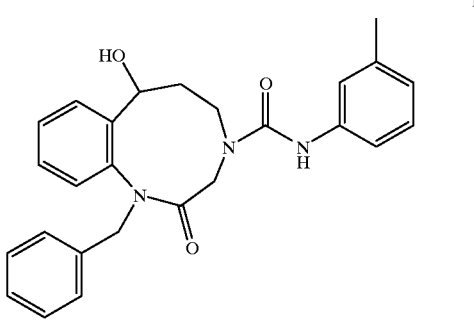

Ex. 8
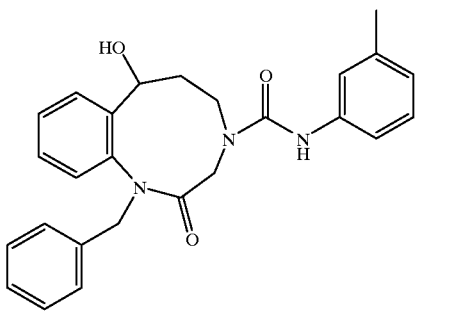

Ex. 9
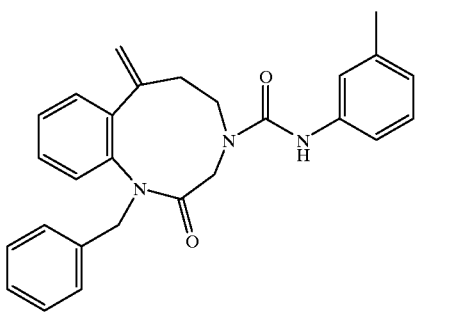

Ex. 10
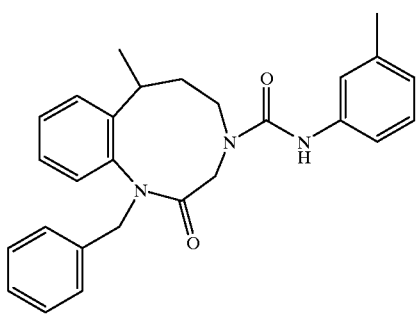
Ex. 11
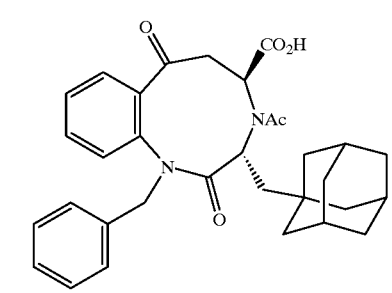
Ex. 12
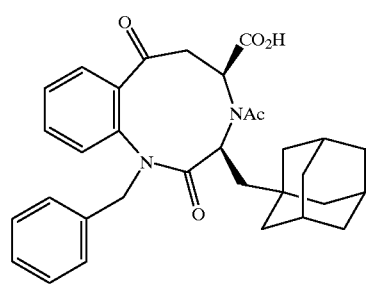
Ex. 13
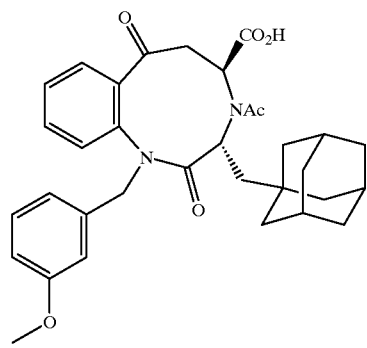
Ex. 14
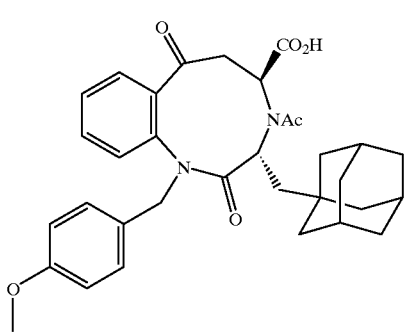
Ex. 15
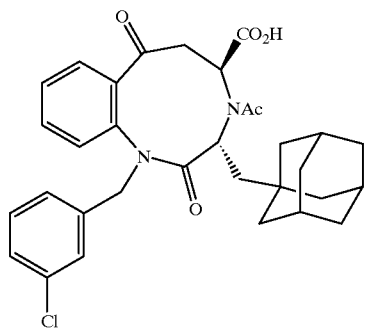
Ex. 16
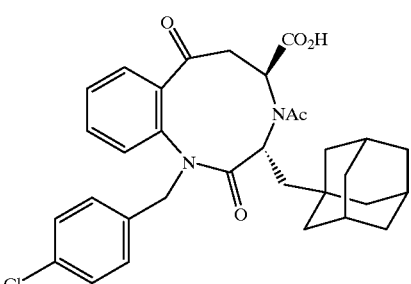
Ex. 17
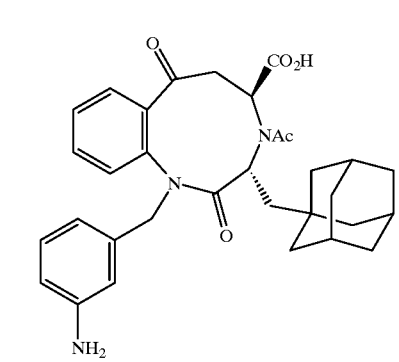
Ex. 18
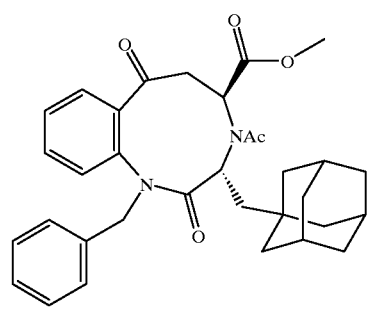
Ex. 19
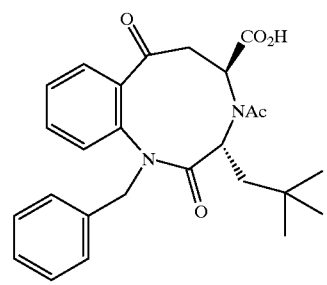

Ex. 20
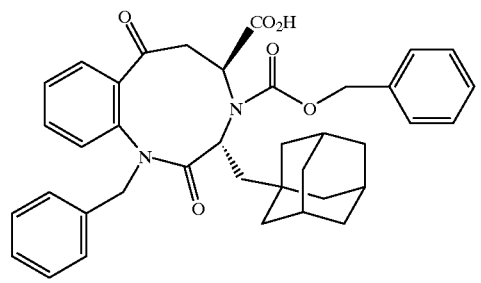
Ex. 21
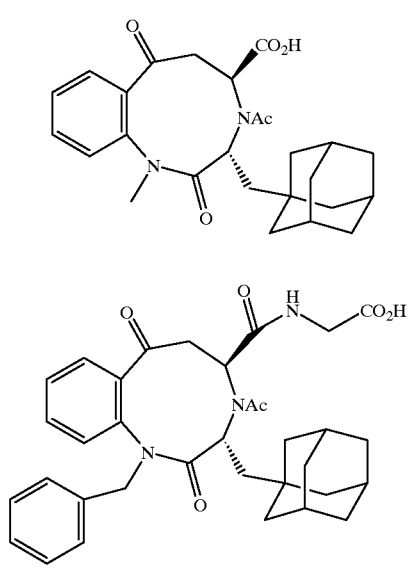
Ex. 22
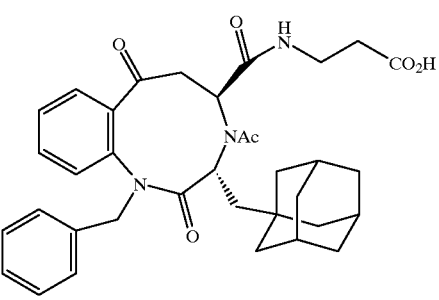
Ex. 23
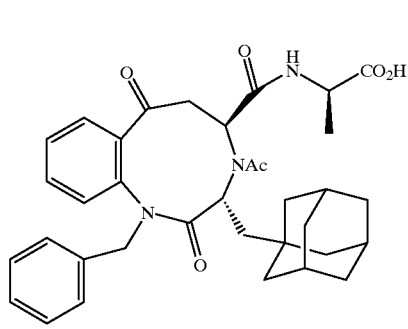
Ex. 24
Ex. 25
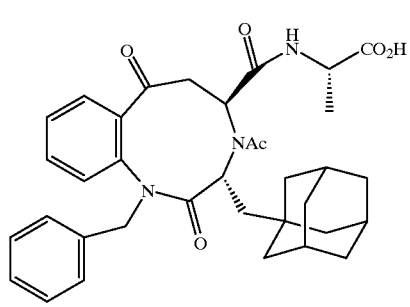
Ex. 26
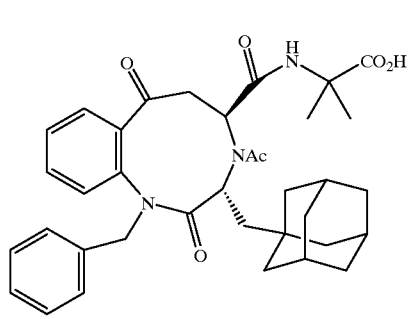
Ex. 27
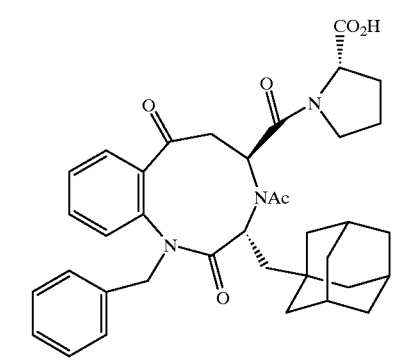
Ex. 28
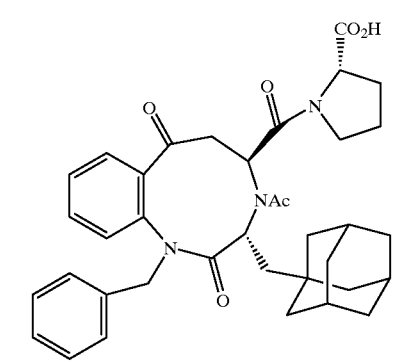

-continued
Ex. 29
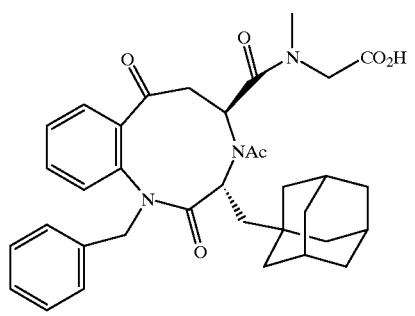
Ex. 30
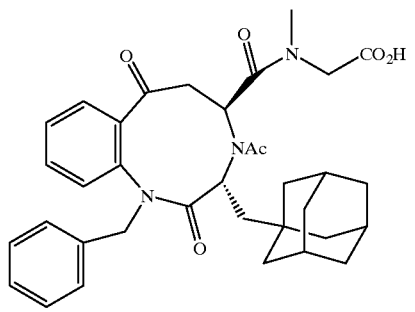
Ex. 31
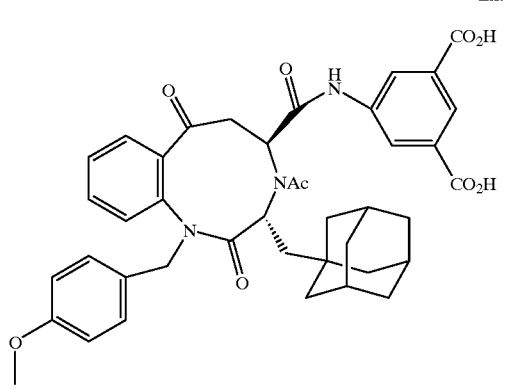
Ex. 32
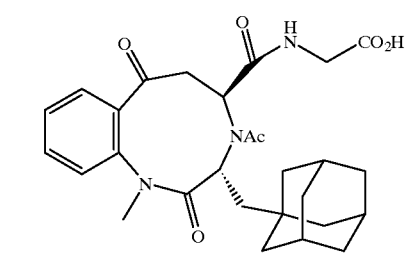
Ex. 33
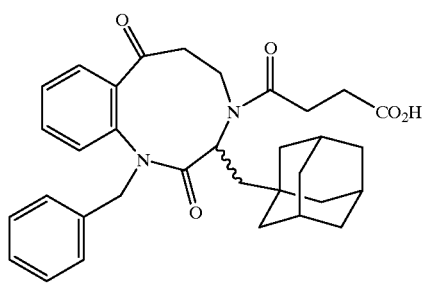
-continued
Ex. 34
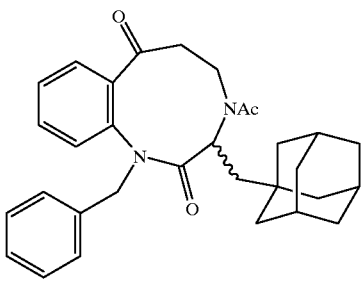
Ex. 35
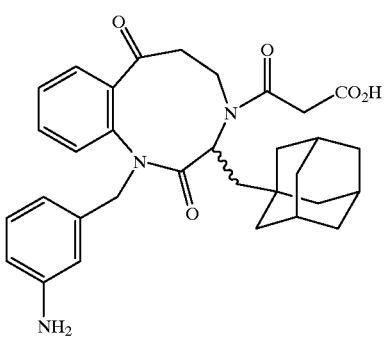
Ex. 36
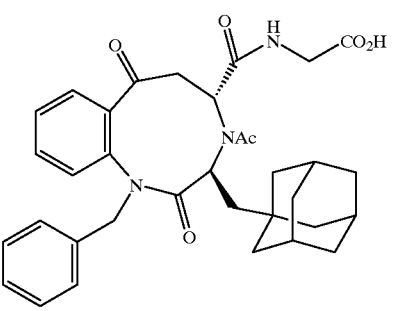
Ex. 37
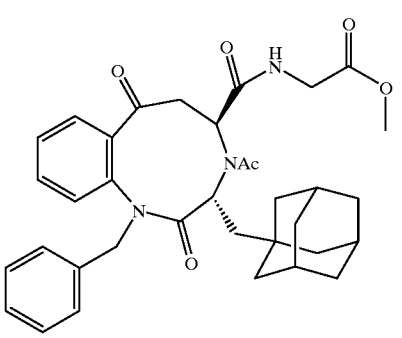
Ex. 38
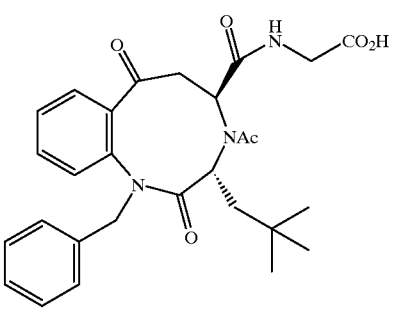

Ex. 39
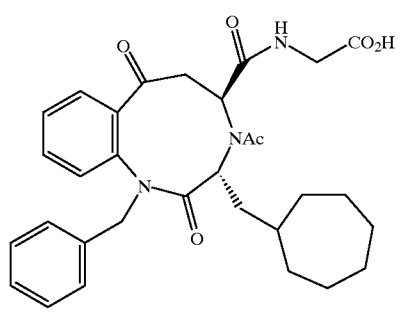
Ex. 40
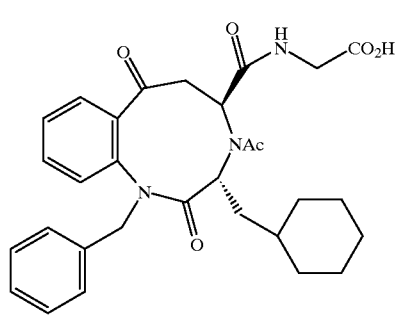
Ex. 41
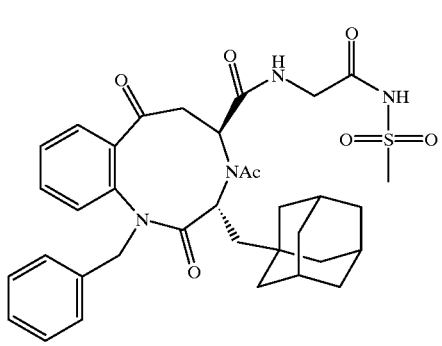
Ex. 42
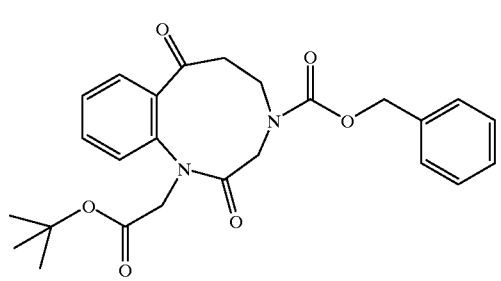
Ex. 43
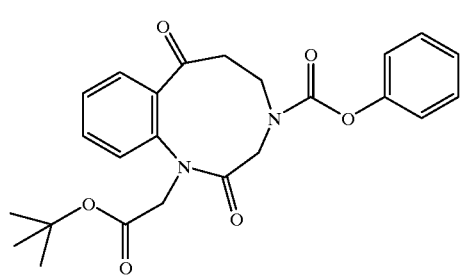
Ex. 44
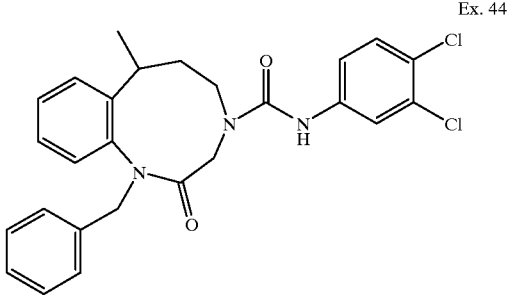
Ex. 45
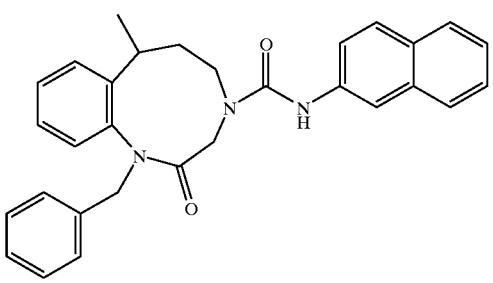
Ex. 46
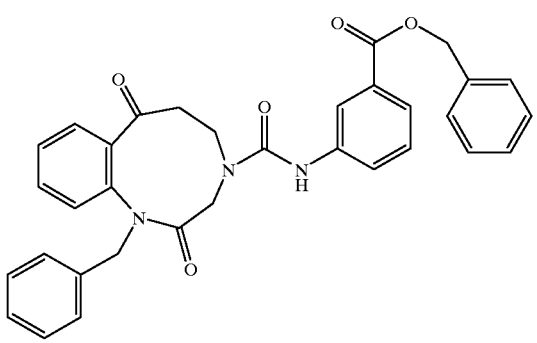
Ex. 47
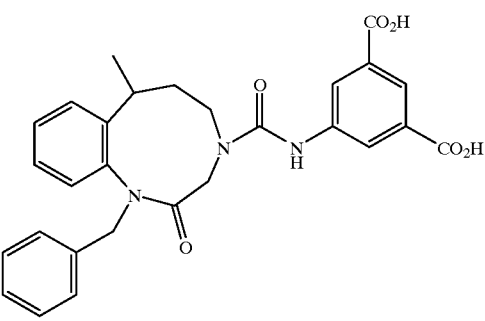
Ex. 48
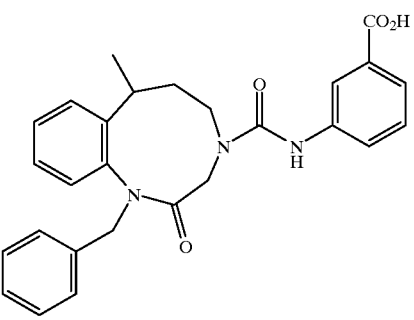

Ex. 49
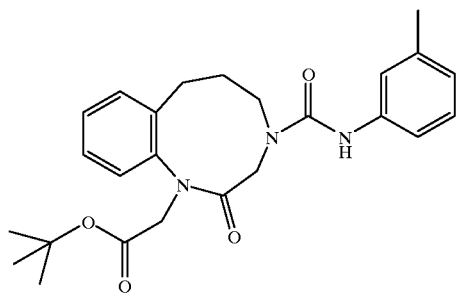
Ex. 50
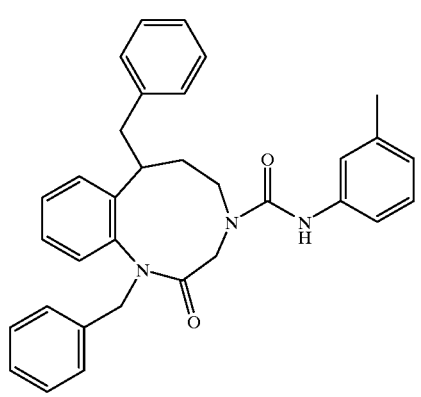
Ex. 51
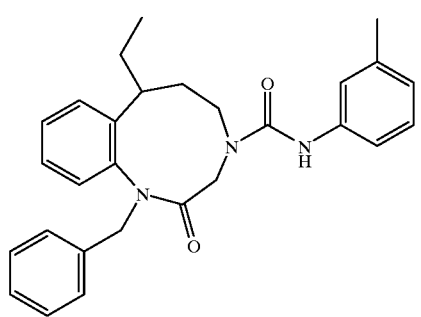
Ex. 52
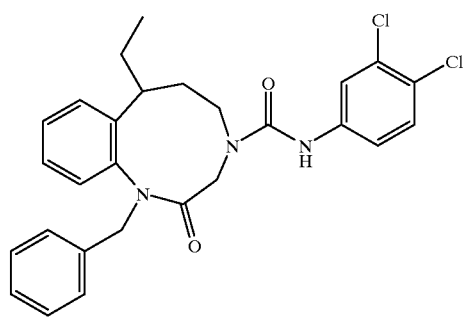
Ex. 53
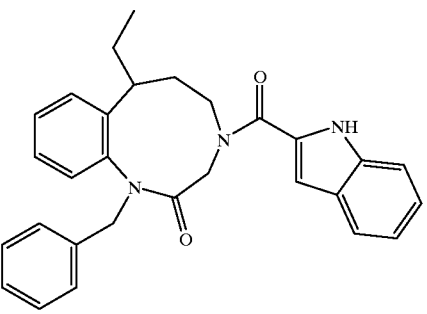
Ex. 54
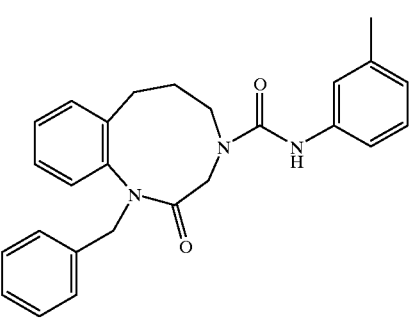
Ex. 55
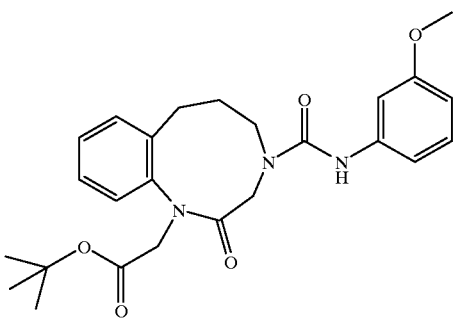
Ex. 56
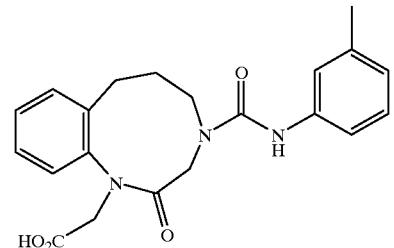
Ex. 57
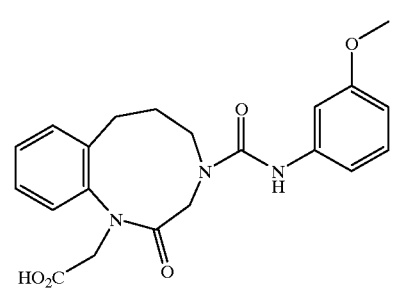

Ex. 58
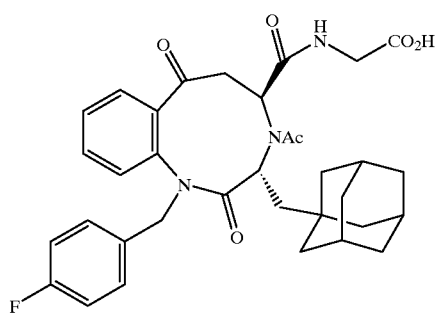
Ex. 59
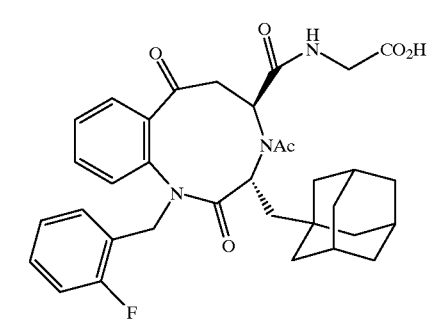
Ex. 60
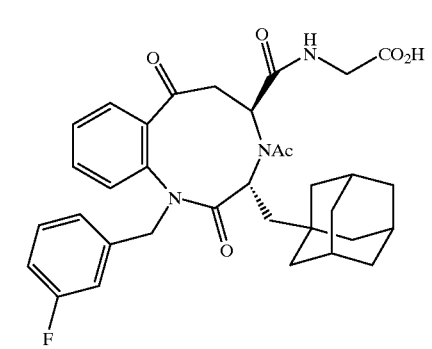
Ex. 61
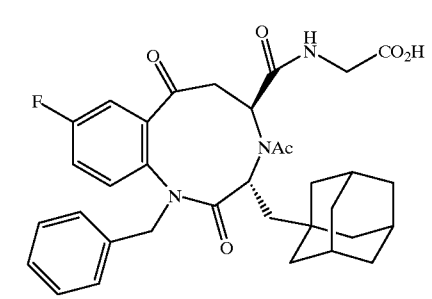
Ex. 62
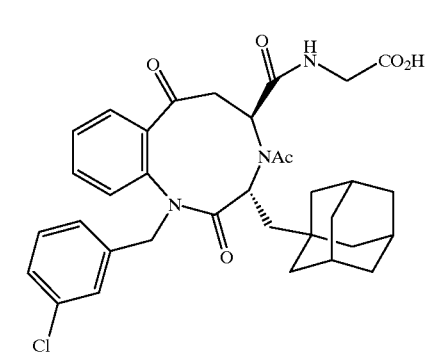
Ex. 63
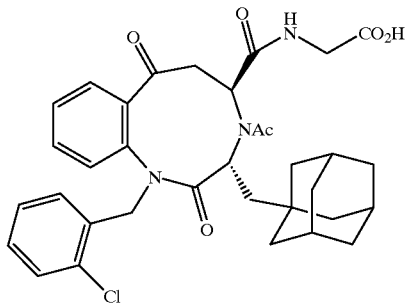
Ex. 64
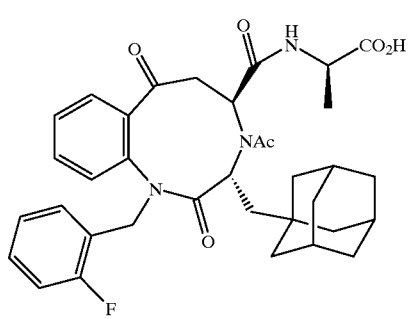
Ex. 65
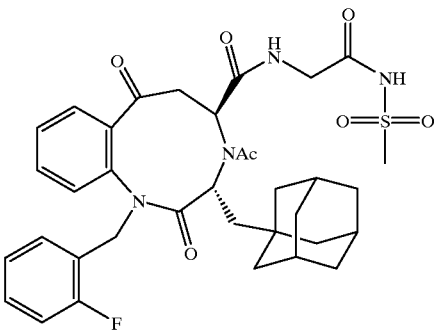
Ex. 66
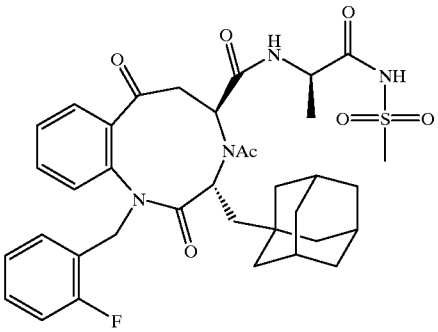
Ex. 67
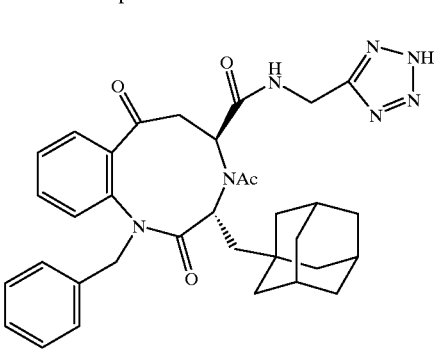

23
-continued

Ex. 68
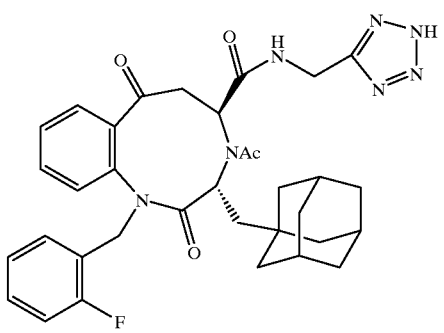

Ex. 69
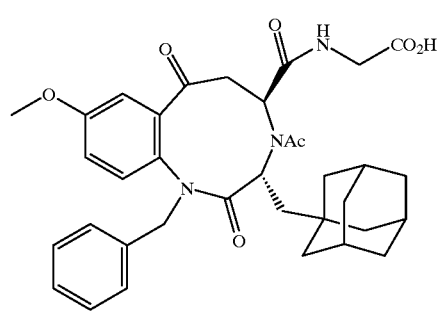

Ex. 70
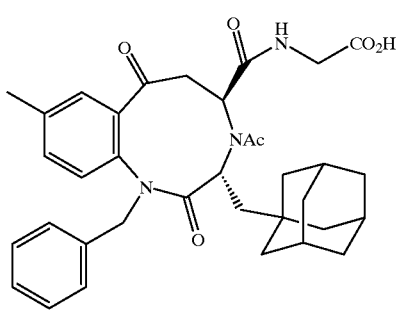

Ex. 71
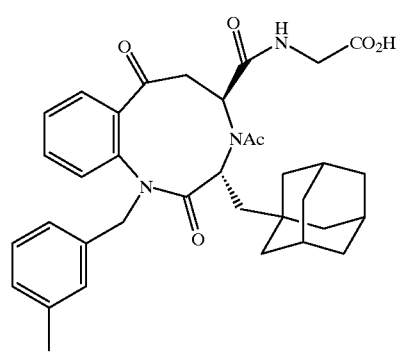

Ex. 72
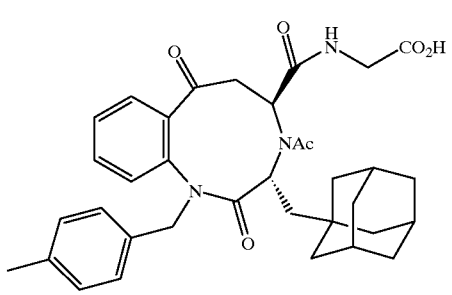

24
-continued

Ex. 73
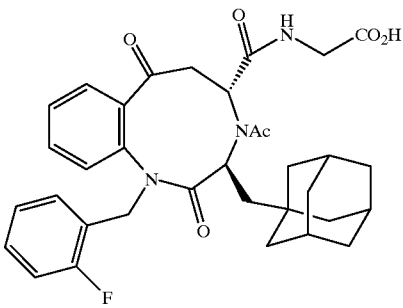

Ex. 74
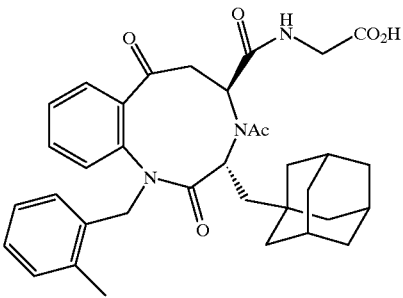

Ex. 75
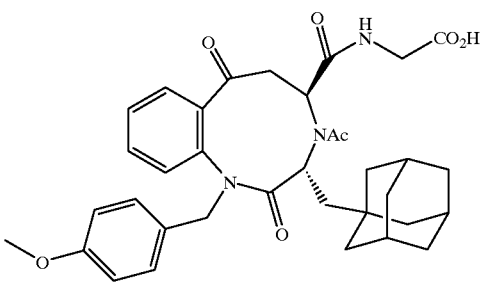

EXAMPLE 1

Preparation of 1-tert-butyloxycarbonylmethyl-4-(3-methylphenyl)carbamyl-2,7-dioxo-2,3,4,5,6,7-hexahydro-1H-1,4-benzodiazonine a. 2-benzyloxycarbonyl-1,2,3,4-tetrahydro-9H-pyrido[3,4-b]indole Benzyl chloroformate (1.8 ml, 12.6 mmol) was added to a solution of 1,2,3,4-tetrahydro-9H-pyrido[3,4-b]indole (1.72 g, 10.0 mmol) and sodium bicarbonate (1.85 g, 22.0 mmol) in dioxan (50 ml) at room temperature. The mixture was stirred at room temperature for 16 hours, concentrated in vacuo and the residue dissolved in water (50 ml). The aqueous mixture was extracted with chloroform (3×50 ml), and the combined extracts dried (MgSO$_4$). Filtration and evaporation of the solvent gave the crude product which was purified by chromatography on silica gel with hexane-ethyl acetate (3:2) as eluant. (3.07 g, 100%).

b. 2-benzyloxycarbonyl-9-tert-butyloxycarbonylmethyl-1,2,3,4-tetrahydro-9H-pyrido[3,4-b]indole A solution of 2-benzyloxycarbonyl-1,2,3,4-tetrahydro-9H-pyrido[3,4-b]indole (3.06 g, 10.0 mmol) in dry DMF (30 ml) was added dropwise to a slurry of sodium hydride (60% dispersion in oil/480 mg, 12.0 mmol) in dry DMF (20 ml) under nitrogen at room temperature. The reaction mixture was stirred for one hour at room temperature to which was added dropwise tert-butyl bromoacetate (1.48 ml, 10.0 mmol). The reaction was stirred for a further two hours, diluted with ethyl acetate (100 ml), washed with brine (2×100 ml) and dried (MgSO$_4$). Filtration and evaporation of the solvent gave the crude product which was purified by chromatography on silica gel with ethyl acetate-hexane (2:5) as eluant. (3.28 g, 78%).

c. 9-tert-butyloxycarbonylmethyl-1,2,3,4-tetrahydro-9H-pyrido[3,4-b]indole

2-Benzyloxycarbonyl-9-tert-butyloxycarbonylmethyl-1,2,3,4-tetrahydro-9H-pyrido-[3,4-b]indole (3.28 g, 7.81 mmol) was stirred under an atmosphere of hydrogen in the presence of 10% palladium on charcoal (500 mg) in methanol (30 ml) at room temperature for two hours. The reaction mixture was filtered through a pad of celite and evaporated to dryness affording the product. (2.14 g, 96%).

d. 9-tert-butyloxycarbonylmethyl-2-(3-methylphenyl)carbamyl-1,2,3,4-tetrahydro-9H-pyrido[3,4-b]indole A solution of 9-tert-butyloxycarbonylmethyl-1,2,3,4-tetrahydro-9H-pyrido [3,4-b]indole (3.56 g, 12.0 mmol) and 3-methylphenylisocyanate (1.60 ml, 12.4 mmol) was stirred in dioxan (40 ml) at room temperature for 4 hours. Evaporation of the solvent and chromatography on silica gel with ethyl acetate-hexane (1:3) as eluant gave the product. (3.29 g, 65%).

e. 1-tert-butyloxycarbonylmethyl-4-(3-methylphenyl)carbamyl-2,7-dioxo-2,3,4,5,6,7-hexahydro-1H-1,4-benzodiazonine Ozone was bubbled through a solution of 9-tert-butyloxycarbonylmethyl-2-(3-methyl-phenyl)carbamyl1,2,3,4-tetrahydro-9H-pyrido[3,4-b]indole (2.99 g, 7.14 mmol) in methanol (35 ml) at −78° C. until a blue colour persisted. Nitrogen was then bubbled through the solution until clear, followed by the addition of dimethyl sulphide (5.0 ml, 68.1 mmol). The solution was allowed to warm to room temperature and stirring continued for a further two hours, followed by evaporation to dryness. The crude product was purified by chromatography on silica gel with ethyl acetate-hexane (1:1 to 2:1) as eluant. (1.79 g, 56%).

(CDCl$_3$) $\delta_H$ 1.53 (9H, s), 2.33 (3H, s), 2.75 and 4.74 (2H, 2×m), 3.0 (2H, m), 3.35 and 4.16 (2H, 2×d, J=15 Hz), 3.69 and 4.83 (2H, 2×d, J=17 Hz), 6.82 (1H, m), 7.16–7.77 (7H, m), 9.24 (1H, bs).

Found: C, 66.52; H, 6.68; N, 9.45. C$_{25}$H$_{29}$N$_3$O$_5$ requires C, 66.50; H, 6.47; N, 9.31%

EXAMPLE 2

Preparation of 1-tert-butyloxycarbonylmethyl-4-(3,4-dichlorophenyl)-carbamyl-2,7-dioxo-2,3,4,5,6,7-hexahydro-1H-1,4-benzodiazonine The compound was prepared by an identical method to that used in the preparation of example 1 except that 3,4-dichlorophenylisocyanate was used in step d in place of 3-methylphenylisocyanate.

(CDCl$_3$) $\delta_H$ 1.54 (9H, s), 2.75 and 4.70 (2H, 2×m), 3.0 (2H, m), 3.45 and 4.14 (2H, 2×m d, J=15 Hz), 3.69 and 4.86 (2H, 2×d, J=17 Hz), 7.30 (2H, m), 7.48–7.76 (5H, m), 9.54 (1H, s).

Found: C, 56.80; H, 5.05; N 8.42. C$_{24}$H$_{25}$Cl$_2$N$_3$O$_5$ requires C, 56.90; H, 4.98; N, 8.30%

EXAMPLE 3

Preparation of 1-benzyl-4-(3-methylphenyl)carbamyl-2,7-dioxo-2,3,4,5,6,7-hexahydro-1H-1,4-benzodiazonine a. 2-butyloxycarbonyl-1,2,3,4-tetrahydro-9H-pyrido[3,4-b]indole

A solution of 1,2,3,4-tetrahydro-9H-pyrido[3,4-b]indole (8.96 g, 52 mmol) and di-tert-butyl dicarbonate (11.4 g, 52 mmol) in dioxan (180 ml) was stirred at room temperature for 17 hours. The solvent was evaporated to afford the crude product which was then recrystallised from dichloromethane-hexane. (13.9 g, 98%).

b. 9-benzyl-2-tert-butyloxycarbonyl-1,2,3,4-tetrahydro-9H-pyrido[3,4-b]indole A solution of 2-tert-butyloxycarbonyl-1,2,3,4-tetrahydro-9H-pyrido[3,4-b]indole(2.96 g, 10.9 mmol) in dry DMF (15 ml) was added dropwise to a slurry of sodium hydride (60% dispersion in oil/479 mg, 12.0 mmol) in dry DMF (15 ml) maintained under nitrogen at room temperature. After stirring for 45 minutes at room temperature benzyl bromide (1.3 ml, 10.9 mmol) was added dropwise. The reaction was stirred for a further 2 hours, diluted with ethyl acetate (75 ml), washed with brine (2×80 ml) and dried (MgSO$_4$). Filtration and evaporation of the solvent gave the crude product which was purified by chromatography on silica gel with ethyl acetate-hexane (2:7) as eluant. (3.68 g, 92%).

c. 9-benzyl-1,2,3,4-tetrahydro-9H-pyrido[3,4-b]indole

A solution of 9-benzyl-2-tert-butyloxycarbonyl-1,2,3,4-tetrahydro-9H-pyrido[3,4-b]-indole (3.66 g, 10.1 mmol) in chloroform (50 ml) was stirred with trifluoroacetic acid (20 ml) at room temperature for 2 hours. The mixture was evaporated to dryness and the residue partitioned between chloroform and saturated potassium carbonate solution (150 ml/1:2). The organic layer was separated and dried (MgSO$_4$). Filtration and evaporation of the solvent gave the product. (2.66 g, 100%).

d. 9-benzyl-2-(3-methylphenyl)carbamyl-1,2,3,4-tetrahydro-9H-pyrido[3,4-b]-indole A solution of 9-benzyl-1,2,3,4-tetrahydro-9H-pyrido[3,4-b]indole(2.66 g, 10.1 mmol) and 3-methylphenylisocyanate (1.42 ml, 11.0 mmol) was stirred in dioxan (40 ml) at room temperature for 4 hours. Evaporation of the solvent and chromatography on silica gel with ethyl acetate-hexane (2:3) as eluant gave the product. (3.04 g, 76%).

e. 1-benzyl-4-(3-methylphenyl)carbamyl-2,7-dioxo-2,3,4,5,6,7-hexahydro-1H-1,4-benzodiazonine Ozone was bubbled through a solution of 9-benzyl-2-(3-methylphenyl)carbamyl-1,2,3,4-tetrahydro-9H-pyrido[3,4-b]indole (2.98 g, 7.54 mmol) in methanol (40 ml) at −78° C. until a blue colour persisted. Nitrogen was then bubbled through the solution until clear, followed by the addition of dimethyl sulphide (5.0 ml, 68.1 mmol). The solution was allowed to warm to room temperature and stirring continued for a further 2 hours, followed by evaporation to dryness. The crude product was purified by chromatography on silica gel with ethyl acetate-hexane (3:2) as eluant. (2.0 g, 62%).

(CDCl$_3$) $\delta_H$ 2.34 (3H, s), 2.70 and 4.75 (2H, 2×m), 3.0 (2H, m), 3.51 and 4.21 (2H, 2×d, J=15 Hz), 4.05 and 5.77 (2H, 2×d, J=14 Hz), 6.80 (2H, m), 7.18–7.50 (11H, m), 9.50 (1H, s).

(CDCl$_3$) $\delta_c$ 21.4, 44.8, 47.5, 52.9, 54.4, 116.7, 120.2, 123.4, 125.8, 127.8, 128.6, 129.0, 129.1, 129.4, 131.0, 136.0, 138.0, 138.5, 139.0, 140.0, 155.0, 170.0, 204.3.

Found: C, 72.81; H, 5.94; N, 9.85. C$_{26}$H$_{25}$N$_3$O$_3$ requires C, 73.05; H, 5.89; N, 9.83%

EXAMPLE 4

Preparation of 1-ethoxycarbonylmethyl-4-(3-methylphenyl)carbamyl-2,7-dioxo-2,3,4,5,6,7-hexahydro-1H-1,4-benzodiazonine The compound was prepared by an identical route to that used in the preparation of example 3 except that ethylbromoacetate was used in step b in place of benzyl bromide.

(CDCl$_3$) $\delta_H$ 1.34 (3H, t), 2.33 (3H, s), 2.76 and 4.76 (2H, 2×m), 3.03 (2H, m), 3.41 and 4.22 (2H, 2×d, J=15 Hz), 3.85 and 4.97 (2H, 2×d, J=17 Hz), 4.30 (2H, m), 6.82 (1H, m), 7.2 (3H, m), 7.48–7.61 (3H, m), 7.75–7.89 (1H, m), 9.19 (1H, s).

Found: C, 56.60; H, 6.49; N, 8.71. C$_{23}$H$_{25}$N$_3$O$_5$. 3.5 H$_2$O requires C, 56.70; H, 6.58; N, 8.64%

EXAMPLE 5

Preparation of 4-(3-methylphenyl)carbamyl-2,7-dioxo-2,3,4,5,6,7-hexahydro-1H-1,4-benzodiazonine The compound was prepared by an identical route to that used in the preparation of example 3 except that 1,2,3,4-tetrahydro-9H-pyrido[3,4-b]indole was used in step d in place of 9-benzyl-1,2,3,4-tetrahydro-9H-pyrido[3,4-b]-indole.

(CDCl$_3$) $\delta_H$ 2.37 (3H, s), 3.0 (2H, t, J=6 Hz), 3.74 (4H, bs), 6.85 (1H, m), 7.17–7.59 (8H, m), 9.12 (1H, s).

Found: C, 67.31; H, 5.73; N, 12.22. C$_{19}$H$_{19}$N$_3$O$_3$ requires C, 67.64; H, 5.68; N, 12.46%

EXAMPLE 6

Preparation of 4-(3-methylphenyl)carbamyl-2,7-dioxo-1-pyrrolidinoyl-methyl-2,3,4,5,6,7-hexahydro-1H-1,4-benzodiazonine a. 1-carboxymethyl-4-(3-methylphenyl)carbamyl-2,7-dioxo-2,3,4,5,6,7-hexahydro-1H-1,4-benzodiazonine A solution of 1-tert-butyloxycarbonyl-4-(3-methylphenyl)carbamyl-2,7-dioxo-2,3,4,5,6,7-hexahydro-1H-1,4-benzodiazonine (452 mg, 1.0 mmol) in chloroform (4 ml) was stirred with trifluoroacetic acid (4 ml) at room temperature for 2 hours. The mixture was evapoarted to dryness and the residue dissolved in chloroform (50 ml), washed with brine (3×40 ml), and dried (MgSO$_4$). Filtration and evaporation of the solvent gave the product. (393 mg, 99%).

b. 4-(3-methylphenyl)carbamyl-2,7-dioxo-1-pyrrolidinoylmethyl-2,3,4,5,6,7-hexahydro- 1H-1,4-benzodiazonine Pyrrolidine (117 μl, 1.41 mmol) was added to a solution of 1-carboxymethyl-4-(3-methylphenyl)carbamyl-2,7-dioxo-2,3,4,5,6,7-hexahydro-1H-1,4-benzodiazonin(373 mg, 0.94 mmol), EDC (181 mg, 0.94 mmol) and HOBt (127 mg, 0.94 mmol) in DMF (3 ml) at room temperature. The reaction mixture was stirred at room temperature for 28 hours, diluted with water (50 ml), and extracted with ethyl acetate (50 ml). The organic extract was washed with 10% citric acid solution (50 ml), brine (2×50 ml) and dried (MgSO$_4$). Filtration and evaporation of the solvent gave the crude product which was purified by chromatography on silica gel with ethyl acetate as eluant. (138 mg, 34%).

(CDCl$_3$) $\delta_H$ 1.86–2.05 (4H, m), 2.31 (3H, s), 2.80 and 4.75 (2H, 2×m), 3.0 (2H, m), 3.32–3.78 (6H, m), 4.17 and 4.96 (2H, 2×d, J=16 Hz), 6.80 (1H, m), 7.15–7.58 (6H, m), 8.02 (1H, m), 9.32 (1H, s).

Found: C, 66.70; H, 6.41; N, 12.60. C$_{25}$H$_{28}$N$_4$O$_4$ requires C, 66.90; H, 6.29; N, 12.50%

EXAMPLE 7

Preparation of 1-benzyl-7-hydroxy-4-(3-methylphenyl)carbamyl-2-oxo-2,3,4,5,6,7-hexahydro-1H-1,4-benzodiazonine (isomer 1)

Sodium borohydride (19 mg, 0.5 mmol) was added in a single portion to a solution of 1-benzyl-4-(3-methylphenyl)carbamyl-2,7-dioxo-2,3,4,5,6,7-hexahydro-1H-1,4-benzodiazonine (213 mg, 0.5 mmol) in methanol (5 ml) at room temperature. The reaction mixture was stirred at room temperature for 10 minutes followed by the addition of saturated ammonium chloride solution (40 ml). The mixture was extracted with chloroform (3×40 ml), and the combined extracts dried over magnesium sulphate. Filtration and evaporation of the solvent gave the crude product. The compound was obtained by isolation of the less polar component by chromatography on silica gel, with ethyl acetate-hexane (1:1) as eluant. (104 mg, 48%)

(CDCl$_3$) $\delta_H$ 1.50 (2H, m), 1.79 (1H, dt, J=14, 3 Hz), 2.33–2.42 (4H, m), 3.22 (1H, d, J=15 Hz), 4.08–4.33 (4H, m), 5.84 (1H, d, J=14 Hz), 6.87 (1H, m), 7.12–7.49 (12H, m), 9.40 (1H, s).

Found: C, 71.31; H, 6.35; N, 9.65. C$_{26}$H$_{27}$N$_3$. 0.5 H$_2$O requires C, 71.21; H, 6.44; N, 9.58%

EXAMPLE 8

Preparation of 1-benzyl-7-hydroxy-4-(3-methylphenyl)carbamyl-2-oxo-2,3,4,5,6,7-hexahydro-1H-1,4-benzodiazonine (isomer 2)

The compound was prepared by an identical route to that used in the preparation of example 7 except that the more polar component was isolated by chromatography. (78 mg, 36%)

(CDCl$_3$) $\delta_H$ 1.50 (2H, m), 1.79 (1H, dt, J=14, 3 Hz), 2.33–2.42 (4H, m), 3.22 (1H, d, J=15 Hz), 4.08–4.33 (4H, m), 5.84 (1H, d, J=14 Hz), 6.87 (1H, m), 7.12–7.49 (12H, m), 9.40 (1H, s).

Found: C, 72.39; H, 6.41; N, 9.50. C$_{26}$H$_{27}$N$_3$O$_3$ requires C, 72.71; H, 6.34; N, 9.78%

EXAMPLE 9

Preparation of 1-benzyl-7-methylene-4-(3-methylphenyl)carbamyl-2-oxo-2,3,4,5,6,7-hexahydro-1H-1,4-benzodiazonine a. 1-benzyl-4-tert-butyloxycarbonyl-2,7-dioxo-2,3,4,5,6,7-hexahydro-1H-1,4-benzodiazonine Ozone was bubbled through a solution of 9-benzyl-2-tert-butyloxycarbonyl-1,2,3,4-tetrahydro-9H-pyrido[3,4-b]

indole (6.0 g, 16.6 mmol) in methanol (90 ml) at -78° C. until a blue colour persisted. Nitrogen was then bubbled through the solution until clear, followed by the addition of dimethyl sulphide (12.0 ml, 163 mmol). The solution was allowed to warm to room temperature and stirring continued for a further 2 hours, followed by evaporation to dryness. The crude product was purified by chromatography on silica gel with ethyl acetate-hexane (1:1) as eluant. (6.0 g, 92%).

b. 1-benzyl-4-tert-butyloxycarbonyl-7-methylene-2-oxo-2,3,4,5,6,7-hexahydro-1H-1,4-benzodiazonine $\mu$-Chloro-$\mu$-methylene-[bis(cyclopentadienyl)titanium] dimethylaluminium (0.5M in toluene/15 ml, 7.5 mmol) was added to a solution of 1-benzyl-4-tert-butyloxycarbonyl-2,7-dioxo-2,3,4,5,6,7-hexahydro-1H-1,4-benzodiazonine (2.95 g, 7.5 mmol) in tetrahydrofuran (23 ml) at -5° C. The resultant suspension was stirred at -5° C. for 15 minutes then allowed to warm to room temperature. Stirring was continued for a further 30 minutes followed by the addition of ethyl acetate (50 ml) and the mixture was washed with 0.2M sodium hydroxide solution (1.5 ml), and dried (MgSO$_4$). The mixture was filtered through a pad of celite and evaporated to dryness. The crude product was purified by chromatography on silica gel with ethyl acetate-hexane (1:3) as eluant. (981 mg, 33%).

c. 1-benzyl-7-methylene-2-oxo-2,3,4,5,6,7-hexahydro-1H-1,4-benzodiazonine

A solution of 1-benzyl-4-tert-butyloxycarbonyl-7-methylene-2-oxo-2,3,4,5,6,7-hexahydro-1H-1,4-benzodiazonine (154 mg, 0.39 mmol) in chloroform (2 ml) was stirred with trifluoroacetic acid (1 ml) at room temperature for 45 minutes. The mixture was evapoarted to dryness and the residue partitioned between chloroform and saturated potassium carbonate solution (60 ml/1:2). The organic layer was separated and dried (MgSO$_4$). Filtration and evapoartion of the solvent gave the product. (94 mg, 83%).

d. 1-benzyl-7-methylene-4-(3-methylphenyl) carbamyl-2-oxo-2,3,4,5,6,7-hexahydro-1H-1,4-benzodiazonine A solution of 1-benzyl-7-methylene-2-oxo-2,3,4,5,6,7-hexahydro-1H-1,4-benzodiazonine (94 mg, 0.32 mmol) and 3-methylphenylisocyanate (42 $\mu$l, 0.33 mmol) was stirred in dichloromethane (2 ml) at room temperature for 3 hours. Evaporation of the solvent and chromatography on silica gel with ethyl acetate-hexane as eluant (1:1) gave the product. (131 mg, 96%).

(CDCl$_3$) $\delta_H$ 2.25 and 2.80 (1H, 2×m), 2.34 (3H, s), 2.66 and 4.54 (2H, 2×m), 3.30 and 4.21 (2H, 2×d, J=15 Hz), 4.02 and 5.60 (2H, 2×d, J=14 Hz), 4.81 (1H, s), 5.34 (1H, s), 6.93 (1H, m), 7.17 (1H, m), 7.25–7.41 (11H, m), 9.62 (1H, bs).

Found: C, 75.97; H, 6.66; N, 10.01. C$_{27}$H$_{27}$N$_3$O$_2$ requires C, 76.21; H, 6.40; N, 9.87%

EXAMPLE 10

1-benzyl-7-methyl-4-(3-methylphenyl)carbamyl-2-oxo-2,3,4,5,6,7-hexahydro-1H-1,4-benzodiazonine a. 1-benzyl-4-tert-butyloxycarbonyl-7-methyl-2-oxo-2,3,4,5,6,7-hexahydro-1H-1,4-benzodiazonine 1-Benzyl-4-tert-butyloxycarbonyl-7-methylene-2-oxo-2,3,4,5,6,7-hexahydro-1H-1,4-benzodiazonine (160 mg, 0.41 mmol) was stirred under an atmosphere of hydrogen in the presence of 10% palladium on charcoal (20 mg) in dioxan (5 ml) at room temperature for 20 hours. The reaction mixture was filtered through a pad of celite and evaporated to dryness affording the product. (160 mg, 100%).

b. 1-benzyl-7-methyl-2-oxo-2,3,4,5,6,7-hexahydro-1H-1,4-benzodiazonine

A solution of 1-benzyl-4-tert-butyloxycarbonyl-7-methyl-2-oxo-2,3,4,5,6,7-hexahydro- 1H-1,4-benzodiazonine (160 mg, 0.41 mmol) in chloroform (2 ml) was stirred with trifluoroacetic acid (3 ml) at room temperature for 30 minutes. The mixture was evaporated to dryness and the residue partitioned between chloroform and saturated potassium carbonate solution (30 ml/1:2). The organic layer was separated and dried (MgSO$_4$). Filtration and evaporation of the solvent gave the product. (98 mg, 81%).

c. 1-benzyl-7-methyl-4-(3-methylphenyl)carbamyl-2-oxo-2,3,4,5,6,7-hexahydro-1H-1,4-benzodiazonine A solution of 1-benzyl-7-methyl-2-oxo-2,3,4,5,6,7-hexahydro-1H-1,4-benzodiazonine (96 mg, 0.33 mmol) and 3-methylphenylisocyanate (47 $\mu$l, 0.36 mmol) was stirred in dioxan (2 ml) at room temperature for 2 hours. Evaporation of the solvent and chromatography on silica gel with ethyl acetate-hexane (1:2) as eluant gave the product. (102 mg, 72%).

(CDCl$_3$) $\delta_H$ 0.56 (3H, d, J=7 Hz), 1.35 and 1.88 (2H, 2×m), 2.08 and 2.64 (2H, 2×m), 2.36 (3H, s), 3.27 and 4.22 (2H, 2×d, J=15 Hz), 4.28 (1H, m), 4.62 and 5.30 (2H, 2×m d, J=14 Hz), 6.83 (1H, m), 7.10–7.41 (12H, m), 9.51 (1H, s).

Found: C, 75.80; H, 6.89; N, 9.68. C$_{27}$H$_{29}$N$_3$O$_2$ requires C, 75.90; H, 6.84; N, 9.84%

EXAMPLE 11

Preparation of (3R,5S) 4-acetyl-3-[(1-adamantyl)methyl]-1-benzyl-2,7-dioxo-2,3,4,5,6,7-hexahydro-1H-1,4-benzodiazonine-5-carboxylate a. (1R,3S)-benzyl 1-(1-adamantyl)methyl-1,2,3,4-tetrahydro-9H-pyrido[3,4-b]-indole-3-carboxylate Trifluoroacetic acid (270 $\mu$l, 3.5 mmol) was added to a solution of L-tryptophan benzyl ester (10.23 g, 34.8 mmol) and 1-adamantylacetaldehyde (6.2 g, 34.8 mmol) in dry DCM (300 ml) wth 3A molecular sieves (46.5 g) at -10° C. The reaction mixture was allowed to warm to room temperature and stirred for 7 hours. The mixture was cooled to 0° C. trifluoroacetic acid (5.6 ml, 72.7 mmol) added, and stirring continued at room temperature for 16 hours. The reaction mixture was filtered, washed successively with saturated NaHCO$_3$ solution (200 ml), brine (2×200 ml) and dried (MgSO$_4$). Filtration and evaporation of the solvent gave the crude product. The compound was obtained by isolation of the more polar component by flash chromatography on silica gel with ethyl acetate-DCM (1:40) as eluant. (6.2 g, 39%)

b. (1R ,3S)-benzyl 2-acetyl-1-(1-adamantyl)methyl-1,2,3,4-tetrahydro-9H-pyrido-[3,4-b]indole-3-carboxylate Acetyl chloride (1.2 ml, 16.9 mmol) was added to a solution of (1R,3S)-benzyl t-(1-adamantyl)methyl-1,2,3,4-tetrahydro-9H-pyrido[3,4-b]indole-3-carboxylate (6.24 g, 13.7 mmol) and triethylamine (1.9 ml, 13.6 mmol) with DMAP (30 mg) in dry DCM (120 ml) at -20° C. under nitrogen. The solution was allowed to warm to room temperature and after stirring for a further 2 hours was washed successively with 10% citric acid solution (100 ml), brine (2×100 ml) and dried (MgSO$_4$). Filtration and evaporation of the solvent gave the crude product which on trituration with ethyl acetate afforded a white amorphous solid which was isolated by filtration and dried. (6.3 g, 93%).

c. (1R,3S)-benzyl 2-acetyl-1-(1-adamantyl)methyl-9-benzyl-1,2,3,4-tetrahydro-9H-pyrido[3,4-b]indole-3-carboxylate A solution of (1R,3S)-benzyl 2-acetyl-1-(1-adamantyl) methyl-1,2,3,4-tetrahydro-9H-pyrido[3,4-b]indole-3-carboxylate (6.3 g, 12.7 mmol) in dry DMF (50 ml) was added dropwise to a slurry of sodium hydride (60% dispersion in oil/0.56 g, 14 mmol) in dry DMF (20 ml) under nitrogen at room temperature. The reaction mixture was stirred for 15 minutes at room temperature to which was added dropwise a solution of benzyl bromide (1.6 ml, 13.5 mmol) in DMF (10 ml). The reaction was stirred for a further one hour, diluted with ethyl acetate (150 ml), washed successively with 2N HCl (150 ml), brine (3×150 ml) and dried (MgSO$_4$). Filtration and evaporation of the solvent gave the product as a yellow foam which was used without further purification. (7.45 g, 100%).

d. (3R,5S)-benzyl 4-acetyl-3-[(1-adamantyl)methyl]-1-benzyl-2,7-dioxo-2,3,4,5,6,7-hexahydro-1H-1,4-benzodiazonine-5-carboxylate Ozone was bubbled through a solution of (1R,3S)-benzyl 2-acetyl-1-(1-adamantyl)-methyl-9-benzyl-1,2,3,4-tetrahydro-9H-pyrido[3,4-b]indole-3-carboxylat(7.45 g, 12.7 mmol) in methanol (200 ml) at −78° C. until a blue colour persisted. Nitrogen was then bubbled through the solution until clear, followed by the addition of dimethyl sulphide (6.0 ml, 81.7 mmol). The solution was allowed to warm to room temperature and stirring continued for a further 2 hours, followed by evaporation to dryness. The crude product was purified by flash chromatography on silica gel with ethyl acetate-DCM (1:19) as eluant, affording the product as a colourless oil. (5.8 g, 72%).

e. (3R,5S)-4-acetyl-3-[(1-adamantyl)methyl]-1-benzyl-2,7-dioxo-2,3,4,5,6,7-hexahydro-1H-1,4-benzodiazonine-5-carboxylate (3R,5S)-Benzyl 4-acetyl-3-[(1-adamantyl)methyl]-1-benzyl-2,7-dioxo-2,3,4,5,6,7-hexahydro-1H-1,4-benzodiazonine-5-carboxylate (5.8 g, 9.2 mmol) was stirred under an atmosphere of hydrogen in the presence of 10% palladium on charcoal (500 mg) in methanol-tetrahydrofuran (100 ml/1:1) at room temperature for one hour. The reaction mixture was filtered through a pad of celite and evaporated to dryness affording the product as a white amorphous solid. (4.75 g, 96%).

(CDCl$_3$) $\delta_H$ 1.20 (3H, s), 1.21–1.36 (4H, m), 1.53–1.69 (9H, m), 1.94 (3H, s), 2.60 (1H, dd), 3.00 (1H, dd), 3.89–4.05 (4H, m), 5.60 (1H, d), 6.75 (1H, d), 7.22–7.46 (8H, m).

$[\alpha]^D = -82.0°$ (C=1.0%, MeOH)

The compound was further characterised and tested as the N-methyl-D-glucamine salt.

Found: C, 61.58; H. 7.68; N 5.69. C$_{39}$H$_{53}$N$_3$O$_{10}$. 2 H$_2$O requires C, 61.64; H, 7.56; N 5.53%

EXAMPLE 12

Preparation of (3S,5S)-4-acetyl-3-(1-adamantyl)methyl-1-benzyl-2,7-dioxo-2,3,4,5,6,7-hexahydro-1H-1,4-benzodiazonine-5-carboxylate Thee compound was prepared by an identical route to that used in the preparation of example 11 except that the less polar component, (1S,3S)-benzyl 1-(1-adamantyl)-methyl-1,2,3,4-tetrahydro-9H-pyrido[3,4-b]indole-3-carboxylate, was isolated by chromatography in step a and used in step b in place of (1R,3S)-benzyl 1-(1-adamantyl)methyl-1,2,3,4-tetrahydro-9H-pyrido[3,4-b]indole-3-carboxylate.

(CDCl$_3$) $\delta_H$ 1.19 (3H, s), 1.24–1.36 (4H, m), 1.44–1.62 (9H, m), 1.94 (3H, s), 2.63 (1H, dd), 3.00 (1H, dd), 3.90–4.06 (4H, m), 5.65 (1H, d), 6.78 (1H, d), 7.22–7.45 (8H, m).

The compound was further characterised and tested as the N-methyl-D-glucamine salt.

Found: C, 60.94; H, 7.60; N, 5.46. C$_{39}$H$_{53}$N$_3$O$_{10}$. 2.5 H$_2$O requires C, 60.92; H, 7.60; N 5.47%

EXAMPLE 13

Preparation of (3R,5S)-4-acetyl-3-[(1-adamantyl)methyl]-1-(3-methoxy)benzyl-2,7-dioxo-2,3,4,5,6,7-hexahydro-1H-1,4-benzodiazonine-5-carboxylate The compound was prepared by an identical route to that used in the preparation of example 11 except that 3-methoxybenzyl bromide was used in step c in place of benzyl bromide.

(d$^6$-DMSO) $\delta_H$ 1.20 (3H, s), 1.34–1.37 (4H, m), 1.44–1.73 (9H, m), 1.93 (3H, s), 2.65 (1H, dd), 3.00 (1H, m), 3.76 (3H, s), 3.89 (1H, d), 3.97–4.07 (3H, m), 5.64 (1H, d), 6.83 (4H, m), 7.20 (2H,m), 7.44 (2H, m).

$[\alpha]^D = -97.0°$ (C=1.0%, MeOH)

The compound was further characterised and tested as the N-methyl-D-glucamine salt.

Found: C, 61.37; H, 7.55; N, 5.29. C$_{40}$H$_{55}$N$_3$O$_{11}$. 1.5 H$_2$O requires C, 61.52; H, 7.49; N, 5.38%

EXAMPLE 14

Preparation of (3R,5S)-4-acetyl-3-[(1-adamantyl)methyl]-1-(4-methoxy)benzyl-2,7-dioxo-2,3,4,5,6,7-hexahydro-1H-1,4-benzodiazonine-5-carboxylate The compound was prepared by an identical route to that used in the preparation of example 11 except that 4-methoxybenzyl bromide was used in step c in place of benzyl bromide.

(CDCl$_3$) $\delta_H$ 1.18 (3H, s), 1.36 (4H, m), 1.44–1.73 (9H, m), 1.94 (3H, s), 2.60 (1H, dd), 3.00 (1H, m), 3.84 (3H, s), 3.88 (1H, d), 3.97–4.03 (3H, m), 5.56 (1H, 6.74 (1H, d), 6.82 (2H, d), 7.15 (2H, d), 7.33–7.43 (3H, m).

$[\alpha]^D = -104.0°$ (C=0.99%, MeOH)

The compound was further characterised and tested as the N-methyl-D-glucamine salt.

Found: C, 60.19; H, 7.37; N, 5.38. C$_{40}$H$_{55}$N$_3$O$_{11}$. 2.5 H$_2$O requires C, 60.14; H, 7.57; N, 5.25%

EXAMPLE 15

Preparation of (3R,5S)-4-acetyl-3-[(1-adamantyl)methyl-1-(3-chloro)benzyl-2,7-dioxo-2,3,4,5,6,7-hexahydro-1H-1,4-benzodiazonine-5-carboxylate The compound was prepared by an identical route to that used in the preparation of example 11 except that 3-chlorobenzyl bromide was used in step c in place of benzyl bromide.

(CDCl$_3$) $\delta_H$ 1.23 (3H, s), 1.36 (4H, m), 1.54–1.73 (9H, m), 1.96 (3H, s), 2.60 (1H, dd), 3.00 (1H, m), 3.88 (1H, d), 4.00 (3H, m), 5.65 (1H, d), 6.84 (1H, d), 7.08 (1H, d), 7.19–7.47 (6H, m).

$[\alpha]^D = -95.0°$ (C=1.0%, MeOH)

The compound was further characterised and tested as the N-methyl-D-glucamine salt.

Found: C, 61.49; H, 6.93; N 5.76. $C_{39}H_{52}ClN_3O_{10}$ requires C, 61.77; H, 6.91; N, 5.54%

EXAMPLE 16

Preparation of (3R,5S)-4-acetyl-3-[(1-adamantyl)methyl]-1-(4-chloro)benzyl-2,7-dioxo-2,3,4,5,6,7-hexahydro-1H-1,4-benzodiazonine-5-carboxylate The compound was prepared by an identical route to that used in the preparation of example 11 except that 4-chlorobenzyl bromide was used in step c in place of benzyl bromide.

($d^6$-DMSO) $\delta_H$ 1.06 (4H, s), 1.26 (3H, d), 1.46 (3H, d), 1.53–1.65 (6H, m), 1.85 (3H, s), 2.40 (1H, dd), 2.75 (1H, m), 3.70 (1H, m), 4.00 (3H, m), 5.27 (1H, d), 7.13 (1H, d), 7.28 (2H, d), 7.37 (2H, d), 7.50 (3H, m).

$[\alpha]^D = 116.0°$ (C=1.0%, DMF)

The compound was further characterised and tested as the N-methyl-D-glucamine salt.

Found: C, 58.19; H, 7.22; N 5.19. $C_{39}H_{52}ClN_3O_{10}$. 2.5 $H_2O$ requires C, 58.31; H, 7.15; N, 5.23%

EXAMPLE 17

Preparation of (3R,5S)-4-acetyl-3-[(1-adamantyl)methyl]-1-(3-amino)benzyl-2,7-dioxo-2,3,4,5,6,7-hexahydro-1H-1,4-benzodiazonine-5-carboxylate The compound was prepared by an identical route to that used in the preparation of example 11 except that 3-nitrobenzyl bromide was used in step c in place of benzyl bromide.

($d^6$-DMSO) $\delta_H$ 1.05 (4H, s), 1.34 (3H, d), 1.52 (3H, d), 1.61 (6H, m), 1.89 (3H, s), 2.44 (1H, dd), 2.72 (1H, dd), 3.66–3.81 (3H, m), 4.00 (1H, d), 5.28 (1H, d), 6.34 (1H, d), 6.38 (1H,s), 6.45 (1H,d), 6.92 (1H, t), 7.03 (1H, d), 7.50 (3H, m).

$[\alpha]^D = -116.0°$ (C=1.0%, DMF)

The compound was further characterised and tested as the N-methyl-D-glucamine salt.

Found: C, 60.89; H, 7.53; N, 7.42. $C_{39}H_{54}N_4O_{10}$. 1.5 $H_2O$ requires C, 61.16; H, 7.50; N, 7.32%

EXAMPLE 18

Preparation of (3R,5S)-methyl 4-acetyl-3-[(1-adamantyl)methyl]-1-benzyl-2,7-dioxo-2,3,4,5,6,7-hexahydro-1H-1,4-benzodiazonine-5-carboxylate The compound was prepared by an identical route to that used in the preparation of example 11 except that L-tryptophan methyl ester was used in step a in place of L-tryptophan benzyl ester.

(CDCl$_3$) $\delta_H$ 1.18 (4H, s), 1.37 (3H, d), 1.54–1.74 (9H, m), 1.95 (3H, s), 2.61 (1H, dd), 3.01 (1H, dd), 3.70 (3H,s), 3.90 (1H, d), 3.94–4.06 (3H, m), 5.67 (1H, d), 6.78 (1H, d), 7.23–7.44 (8H, m).

$[\alpha]^D = -103.3°$ (C=0.91%, MeOH)

Found: C, 60.89; H, 7.53; N, 7.42. $C_{39}H_{54}N_4O_{10}$. 1.5 $H_2O$ requires C, 61.16; H, 7.50; N, 7.32%

EXAMPLE 19

Preparation of (3R,5S)-4-acetyl-1-benzyl-3-(2,2-dimethylpropyl)-2,7-dioxo-2,3,4,5,6,7-hexahydro-1H-1,4-benzodiazonine-5-carboxylate The compound was prepared by an identical route to that used in the preparation of example 11 except that 3,3-dimethylbutyraldehyde was used in step a in place of 1-adamantylacetaldehyde.

($d^6$-DMSO) $\delta_H$ 0.84 (9H, s), 1.13 (3H, s), 1.35 (1H, d), 2.21 (1H, dd), 2.90 (1H, d), 3.38 (1H, dd), 3.87–3.96 (3H,m), 4.68 (1H, d), 5.48 (1H, d), 6.72 (1H, d), 6.94–7.48 (8H, m).

The compound was further characterised and tested as the N-methyl-D-glucamine salt.

Found: C, 56.64; H, 7.63; N, 6.00. $C_{33}H_{47}N_3O_{10}$. 3.0 $H_2O$ requires C, 56.56; H, 7.36; N, 5.94%

EXAMPLE 20

(3R,5S)-3-(1-adamantyl)methyl-1-benzyl-4-benzyloxycarbonyl-2,7dioxo-2,3,4,5,6,7-hexahydro-1H-1,4-benzodiazonine-5-carboxylate The compound was prepared by an identical route to that used in the preparation of example 11 except that benzyl-chloroformate was used in step b in place of acetyl chloride.

($d^6$-DMSO) $\delta_H$ 1.02 (2H, d), 1.25 (4H, d), 1.38 (2H, d), 1.50 (4H, s), 1.64 (3H, s), 1.85 (1H, s), 2.19 (1H, m), 2.93 (1H, m), 3.75–3.95 (2H, m), 4.19 (2H, m), 4.30 and 4.62 (2H, m), 5.46 (1H, d), 6.74 (1H, d), 7.09–7.43 (8H, m).

The compound was further characterised and tested as the N-methyl-D-glucamine salt.

Found: C, 66.33; H, 7.13; N, 5.18. $C_{45}H_{57}N_3O_{11}$ requires C, 66.24; H, 7.04; N, 5.15%

EXAMPLE 21

Preparation of (3R,5S)-4-acetyl-3-(1-adamantyl)methyl-1-methyl-2,7-dioxo-2;3,4,5,6,7-hexahydro-1H-1,4-benzodiazonine-5-carboxylate The compound was prepared by an identical route to that used in the preparation of example 11 except that methyl iodide was used in step c in place of benzyl bromide.

(CDCl$_3$) $\delta_H$ 1.19 (4H, s), 1.26 (3H, d), 1.56–1.74 (6H, m), 1.91 (3H, s), 2.60 (1H, m), 3.00 (1H, m), 3.22 (3H, s), 3.88–4.12 (3H, m), 7.34 (2H, m), 7.49 (1H, t), 7.58 (1H, m).

The compound was further characterised and tested as the N-methyl-D-glucamine salt.

Found: C, 58.42; H, 7.87; N 6.07. $C_{33}H_{49}N_3O_{10}$. 1.5 $H_2O$ requires C, 58.73; H, 7.77; N, 6.23%

EXAMPLE 22

Preparation of (3R,5S)-4-acetyl-3-(1-adamantyl)methyl-1-benzyl-5-carboxymethylaminocarbonyl-2,7-dioxo-2,3,4,5,6,7-hexahydro-1H-1,4-benzodiazonine a. (3R,5S)-4-acetyl-3-(1-adamantyl)methyl-1-benzyl-5-benzyloxycarbonylmethylaminocarbonyl-2,7-dioxo-2,3,4,5,6,7-hexahydro-1H-1,4-benzodiazonine PyBroP (233 mg, 0.5 mmol) was added to a solution of (3R,5S)-4-acetyl-3-(1-adamantyl)methyl-1-benzyl-2,7-dioxo-2,3,4,5,6,7-hexahydro-1H-1,4-benzodiazonine-5-carboxylate (264 mg, 0.5 mmol), glycine benzyl ester p-toluenesulphonate (170 mg, 0.5 mmol) and diisopropyl-ethylamine (260 μl, 1.5 mmol in dry DCM (5 ml). The reaction mixture was stirred at room temperature for 18 hours, diluted with DCM (20 ml), washed successively with 2N HCl solution (25 ml), brine (25 ml) and dried (MgSO$_4$). Filtration an evaporation of the solvent gave the crude product (350 mg) which was purified by flash chromatography on silica gel with ethyl acetate-DCM (3:7) as eluant, affording the product as a colourless oil. (190 mg, 55%).

b. (3R,5 S)-4-acetyl-3-(1-adamantyl)methyl-1-benzyl-5-carboxymethylaminocarbonyl-2,7-dioxo-2,3,4,5,6,7-hexahydro-1H-1,4-benzodiazonine (3R,5S)-4-acetyl-3-(1-adamantyl)methyl-1-benzyl-5-benzyloxycarbonylmethylaminocarbonyl-2,7-dioxo-2,3,4,5,6,7-hexahydro-1H-1,4-benzodiazonine (190 mg, 0.28 mmol) was stirred under an atmosphere of hydrogen in the presence of 10% palladium on charcoal (50 mg) in methanol-tetrahydrofuran (20 ml)/1:1) at room temperature for one hour. The reaction mixture was filtered through a pad of celite and evaporated to dryness affording the product as a white amorphous solid. (154 mg, 92%).

($d^6$-DMSO) $\delta_H$ 1.04 (3H, s), 1.27 (4H, d), 1.45–1.57 (8H, m), 1.86 (3H, s), 2.31 (1H, t), 2.89 (1H, dd), 3.62–3.75 (3H, m), 3.89–3.99 (3H, m), 5.35 (1H, d), 7.00 (1H, m), 7.21–7.30 (5H, m), 7.38 (1H, t), 7.50 (3H, m).

The compound was further characterised and tested as the N-methyl-D-glucamine salt.

Found: C, 60.46; H, 7.57; N, 6.89. $C_{41}H_{56}N_4O_{11}$. 2.0 $H_2O$ requires C, 60.28; H, 7.40; N, 6.86%

EXAMPLE 23

Preparation of (3R,5S)-4-acetyl-3-(1-adamantyl)methyl-1-benzyl-5-(2-carboxy)ethylaminocarbonyl-2,7-dioxo-2,3,4,5,6,7-hexahydro-1H-1,4-benzodiazonine The compound was prepared by an identical route to that used in the preparation of example 22 except that β-alanine benzyl ester was used in step a in place of glycine benzyl ester p-toluenesulphonate.

($d^6$-DMSO) $\delta_H$ 1.04 (3H, s), 1.27 (4H, d), 1.45–1.57 (8H, m), 1.86 (3H, s), 2.31 (3H, m), 2.89 (1H, dd), 3.16–3.21 (3H, m), 3.61 (1H, m), 3.88–3.98 (3H, m), 5.35 (1H, d), 7.00 (1H, m), 7.06 (1H, t), 7.23–7.28 (5H, m), 7.49 (3H, s).

$[\alpha]^D = -56.0°$ (C=1.0%, MeOH)

The compound was further characterised and tested as the N-methyl-D-glucamine salt.

Found: C, 59.19; H, 7.53; N, 6.47. $C_{42}H_{58}N_4O_{11}$. 3.0 $H_2O$ requires C, 59.42; H, 7.60; N, 6.60%

EXAMPLE 24

Preparation of (3R,5S)-4-acetyl-3-(1-adamantyl)methyl-1-benzyl-5-[(1S)-carboxy]ethylaminocarbonyl-2,7-dioxo-2,3,4,5,6,7-hexahydro-1H-1,4-benzodiazonine The compound was prepared by an identical route to that used in the preparation of example 22 except that L-alanine benzyl ester was used in step a in place of glycine benzyl ester p-toluenesulphonate.

($d^6$-DMSO) $\delta_H$ 1.06 (3H, s), 1.19 (3H, d), 1.27 (4H, m), 1.31–1.62 (9H, m), 1.87 (3H, s), 2.40 (1H, t), 2.89 (1H, dd), 3.65 (1H, m), 3.87–4.01 (3H, m), 4.20 (1H, m), 5.38 (1H, d), 7.00 (1H, d), 7.11 (1H, d), 7.21–7.30 (5H, m), 7.49 (3H, m).

The compound was further characterised and tested as the N-methyl-D-glucamine salt.

Found: C, 60.73; H, 7.61; N 6.84. $C_{42}H_{58}N_4O_{11}$. 2.0 $H_2O$ requires C, 60.71; H, 7.52; N, 6.74%

EXAMPLE 25

Preparation of (3R,5S)-4-acetyl-3-(1-adamantyl)methyl-1-benzyl-5-[(1R)-carboxy]ethylaminocarbonyl-2,7-dioxo-2,3,4,5,6,7-hexahydro-1H-1,4-benzodiazonine The compound was prepared by an identical route to that used in the preparation of example 22 except that D-alanine benzyl ester was used in step a in place of glycine benzyl ester p-toluenesulphonate.

($d^6$-DMSO) $\delta_H$ 1.06 (3H, s), 1.24–1.27 (7H, m), 1.31–1.62 (9H, m), 1.86 (3H, s), 2.40 (1H, t), 3.00 (1H, dd), 3.62 (1H, m), 3.86–3.99 (3H, m), 4.06 (1H, m), 5.38 (1H, d), 7.00 (1H, d), 7.22–7.30 (5H, m), 7.41 (1H, d), 7.49 (3H, m).

The compound was further characterised and tested as the N-methyl-D-glucamine salt.

Found: C, 59.22; H, 7.60; N 6.74. $C_{42}H_{58}N_4O_{11}$. 3.0 $H_2O$ requires C, 59.42; H, 7.60; N, 6.60%

EXAMPLE 26

Preparation of (3R,5S)-4-acetyl-3-(1-adamantyl)methyl-1-benzyl-5-(1-carboxy-1-methyl)ethylaminocarbonyl-2,7-dioxo-2,3,4,5,6,7-hexahydro-1H-1,4-benzodiazonine The compound was prepared by an identical route to that used in the preparation of example 22 except that aminoisobutyric acid benzyl ester was used in step a in place of glycine benzyl ester p-toluenesulphonate.

($d^6$-DMSO) $\delta_H$ 1.07–1.36 (11H, m), 1.48–1.69 (12H, m), 1.80 (3H, m), 2.17 and 2.40 (1H, m), 2.65 and 2.95 (1H, m), 3.60 and 4.00 (1H, 2xm), 4.20 (1H, dd), 4.25 and 4.35 (1H, 2xm), 5.25 and 5.60 (2H, 2xm), 6.25–6.94 (1H, 4xm), 7.11 (1H, m), 7.26 (4H, s), 7.44–7.81 (4H, m).

The compound was further characterised and tested as the N-methyl-D-glucamine salt.

Found: C, 61.68; H, 7.53; N, 6.44. $C_{43}H_{60}N_4O_{11}$. 1.5 $H_2O$ requires C, 61.78; H, 7.60; N, 6.70%

EXAMPLE 27

Preparation of (3R,5S)-4-acetyl-3-(1-adamantyl)methyl-1-benzyl-5-[(2S)-carboxy-pyrrolidinyl]carbonyl-2,7-dioxo-2,3,4,5,6,7-hexahydro-1H-1,4-benzodiazonine (isomer 1)

The compound was prepared by an identical route to that used in the preparation of example 22 except that L-proline benzyl ester was used in step a in place of glycine benzyl ester p-toluenesulphonate, and the less polar component isolated by chromatography. The final compound was then prepared by an identical sequence to that used in the preparation of example 22.

($d^6$-DMSO) $\delta_H$ 0.85 and 0.90 (1H, 2xd), 1.17 (2H, 2xm), 1.31–1.39 (2H, m), 1.60 (8H, m), 1.80 (5H, m), 2.09 and 2.49 (2H, 2xm), 3.00 (1H, m), 3.16–3.49 (5H, m), 3.87 (0.5H, m), 4.10–4.34 (2H, m), 4.95–5.30 (1.5, m), 5.45 and 5.69 (1H, 2xm), 7.05 (2H, m), 7.25 (4H, s), 7.51–7.63 (3H, m).

The compound was further characterised and tested as the N-methyl-D-glucamine salt.

Found: C, 61.49; H, 7.64; N, 6.45. $C_{44}H_{60}N_4O_{11}$. 2.0 $H_2O$ requires C, 61.67; H, 7.53; N, 6.54%

EXAMPLE 28

Preparation of (3R,5S)-4-acetyl-3-(1-adamantyl)methyl-1-benzyl-5-[(2S)-carboxy-pyrrolidinyl]carbonyl-2,7-dioxo-2,3,4,5,6,7-hexahydro-1H-1,4-benzodiazonine (isomer 2)

The compound was prepared by an identical route to that used in the preparation of example 22 except that L-proline ester was used in step a in place of glycine benzyl ester p-toluenesulphonate, and the more polar component isolated by chromatography. The final compound was then prepared by an identical sequence to that used in the preparation of example 22.

(d$^6$-DMSO) $\delta_H$ 1.01 (1H, s), 1.12–1.35 (3H, 2×d), 1.47–1.63 (10H, m), 1.73–1.89 (6H, m), 2.20 and 2.41 (1H, 2×m), 2.49 and 3.00 (1H, 2×m), 3.05–3.65 (5H, m), 3.70–4.27 (4H, m), 4.80 (0.5H, 2×d), 5.27 (1H, 2×d), 5.75 (0.5, 2×d), 6.77 and 6.86 (1H, 2×m), 7.19 (2H, s), 7.27 (3H, s), 7.41–7.54 (3H, m).

The compound was further characterised and tested as a N-methyl-D-glucamine salt.

Found: C, 61.41; H, 7.64; N, 6.55. $C_{44}H_{60}N_4O_{11}$ . 2.0 $H_2O$ requires C, 61.67; H, 7.53; N, 6.54%

EXAMPLE 29

Preparation of (3R,5S)-4-acetyl-3-(1-adamantyl) methyl-1-benzyl-5-carboxymethyl-(N-methyl) aminocarbonyl-2,7-dioxo-2,3,4,5,6,7-hexahydro-1H-1,4-benzodiazonine (isomer 1)

The compound was prepared by an identical route to that used in the preparation of example 22 except that sarcosine benzyl ester was used in step a in place of glycine benzyl ester p-toluenesulphonate, and the less polar component isolated by chromatography. The final compound was then prepared by an identical sequence to that used in the preparation of example 22.

(d$^6$-DMSO) $\delta_H$ 1.02 (2H, s), 1.12–1.35 (5H, m), 1.46–1.62 (9H, m), 1.77–1.88 (3H, m), 2.15 and 2.40 (1H, 2×t), 2.60–2.82 (3H, m), 3.04–3.16 (2H, 3×s), 3.75–4.15 (4H, m), 4.40–4.95 (1H, 3×m), 5.31 (1H, 2×d), 6.77 and 6.86 (1H, 2×m), 7.19 (2H, s), 7.28 (3H, s), 7.28–7.52 (3H, m).

The compound was further characterised and tested as the N-methyl-D-glucamine salt.

Found: C, 60.66; H, 7.67; N, 6.84. $C_{42}H_{58}N_4O_{11}$ . 2.0 $H_2O$ requires C, 60.71; H, 7.52; N, 6.74%

EXAMPLE 30

Preparation of (3R,5S)-4-acetyl-3-(1-adamantyl) methyl-1-benzyl-5-carboxymethyl-(N-methyl) aminocarbonyl-2,7-dioxo-2,3,4,5,6,7-hexahydro-1H-1,4-benzodiazonine (isomer 2)

The compound was prepared by an identical route to that used in the preparation of example 22 except that sarcosine benzyl ester was used in step a in place of glycine benzyl ester p-toluenesulphonate, and the more polar component isolated by chromatography. The final compound was then prepared by an identical sequence to that used in the preparation of example 22.

(d$^6$-DMSO) $\delta_H$ 1.16–1.35 (8H, 4×s), 1.47–1.61 (10H, m), 1.91 (3H, 2×s), 2.18 (2H, s), 2.63–2.77 (3H, 3×s), 3.45–4.16 (3.5H, m), 4.36 (0.5H, m), 5.05–5.75 (1H, 4×m), 7.08 (2H, m), 7.26 (4H, m), 7.52–7.64 (3H, m).

The compound was further characterised and tested as the N-methyl-D-glucamine salt.

Found: C, 59.15; H, 7.63; N, 6.64. $C_{42}H_{58}N_4O_{11}$ . 3.0 $H_2O$ requires C, 59.42; H, 7.60; N, 6.60%

EXAMPLE 31

Preparation of (3R,5S)-4-acetyl-3-(1-adamantyl) methyl-1-benzyl-5-(3,5-dicarboxyphenyl) aminocarbonyl-2,7-dioxo-2,3,4,5,6,7-hexahydro-1H-1,4-benzodiazonine The compound was prepared by an identical route to that used in the preparation of example 22 except that (3R,5S)-4-acetyl-3-(1-adamantyl)methyl-1-(4-methoxy)benzyl-2,7-dioxo-2,3,4,5,6,7-hexahydro-1H-1,4-benzodiazonine-5-carboxylate and dibenzyl aniline-3,5-dicarboxylate were used in step a in place of (3R,5S)-4-acetyl-3-(1-adamantyl) methyl-1-benzyl-2,7-dioxo-2,3,4,5,6,7-hexahydro-1H-1,4-benzodiazonine-5-carboxylate and glycine benzyl ester p-toluenesulphonate respectively.

(d$^6$-DMSO) $\delta_H$ 1.12 (2H, d), 1.26–33 (3H, m), 1.53–1.61 (9H, m), 1.85 (3H, s), 2.35 (1H, s), 2.75 and 3.01 (1H, 2×m), 3.71 (3H, s), 4.00 (2H, t), 4.95 and 5.05 (1H, 2×m), 5.65 (2H, 2×d), 6.83 (4H, m), 7.18–7.35 (4H, m), 8.17 (1H, s), 8.40 (2H, s), 9.40 (1H, m).

The compound was further characterised and tested as the N-methyl-D-glucamine salt.

Found: C, 55.67; H, 7.19; N, 5.99. $C_{55}H_{77}N_5O_{19}$ . 4.0 $H_2O$ requires C, 55.78; H, 7.23; N, 5.91%

EXAMPLE 32

Preparation of (3R,5S)-4-acetyl-3-(1-adamantyl) methyl-5-carboxymethylaminocarbonyl-1-methyl-2, 7-dioxo-2,3,4,5,6,7-hexahydro-1H-1,4-benzodiazonine The compound was prepared by an identical route to that used in the preparation of example 22 except that (3R,5S)-4-acetyl-3-(1-adamantyl)methyl-1-methyl-2,7-dioxo-2,3,4,5,6,7-hexahydro-1H-1,4-benzodiazonine-5-carboxylate was used in step a in place of (3R,5S)-4-acetyl-3-(1-adamantyl) methyl-1-benzyl-2,7-dioxo-2,3,4,5,6,7-hexahydro-1H-1,4-benxodiazonine-5-carboxylate.

(d$^6$-DMSO) $\delta_H$ 1.07 (3H, s), 1.30–1.38 (4H, m), 1.48–1.57 (3H, m), 1.62 (6H, s), 1.90 (3H, s), 2.40 (1H, t), 2.89 (1H, dd), 3.07 (3H, s), 3.53–3.67 (3H, m), 3.91–4.01 (2H, m), 7.36 (1H, t), 7.45 (1H, d), 7.52 (1H, t), 7.65 (2H, m).

The compound was further characterised and tested as the N-methyl-D-glucamine salt.

EXAMPLE 33

Preparation of (R/S)-3-(1-adamantyl)methyl-1-benzyl-4-(2-carboxy)ethylcarbonyl-2,7-dioxo-2,3,4, 5,6,7-hexahydro-1H-1,4-benzodiazonine a. (R/S)-1-(1-adamantyl)methyl-1,2,3,4-tetrahydro-9H-pyrido[3,4-b]indole Trifluoroacetic acid (443 µl, 5.8 mmol) was added to a solution of tryptamine (5.76 g, 36 mmol) and 1-adamantylacetaldehyde (6.52 g, 36.6 mmol) in dry DCM (450 ml) wth 3A molecular sieves (46.5 g) at 0° C. The reaction mixture was stirred at 0° C. for 2 hours, followed by the addition of trifluoroacetic acid (5.76 ml, 74.8 mmol) then allowed to warm to room temperature and stirring continued for a further 16 hours. The resultant suspension was concentrated in vacuo, taken up in ethyl acetate (200 ml), filtered, washed successively with saturated NaHCO$_3$ solution (200 ml), brine (2×200 ml) and dried (MgSO$_4$). Filtration and evaporation of the solvent gave the crude product as an orange foam which was used without further purification. (10.95 g, 95%).

b. (R/S)-1-(1-adamantyl)methyl-2-(2-carboxyethyl) carbonyl-1,2,3,4-tetrahydro-9H-pyrido[3,4-b]indole A mixture of (R/S)-1-(1-adamantyl)methyl-1,2,3,4-tetrahydro-9H-pyrido[3,4-b]indole (640 mg, 2.0 mmol) and succinic anhydride (250 mg, 2.5 mmol) was stirred in dioxan (5 ml) at room temperature for 17 hours. The white precipiate which had formed was isolated by filtration, washed with dioxan and dried. (640 mg, 76%).

c. (R/S)-1-(1-adamantyl)methyl-9-benzyl-2-(2-benzyloxycarbonyl)ethylcarbonyl-1,2,3,4-tetrahydro-9H-pyrido[3,4-b]indole A solution of (R/S)-1-(1-adamantyl)methyl-2-(2-carboxyethyl)carbonyl)-1,2,3,4-tetrahydro-9H-pyrido[3,4-b]indole (534 mg, 1.3 mmol) in dry DMF (8 ml) was added dropwise to a slurry of sodium hydride (60% dispersion in oil/115 mg, 2.9 mmol) in dry DMF (3 ml) under nitrogen at room temperature. The reaction mixture was stirred for 15 minutes at room temperature to which was added benzyl bromide (320 µl, 2.7 mmol). The reaction was stirred for a further 2 hours, diluted with ethyl acetate (25 ml) and washed successively with 2N HCl (25 ml), brine (3×20 ml) and dried (MgSO$_4$). Filtration and evaporation of the solvent gave the product as a yellow oil which was purified by flash chromatography on silica gel with ethyl acetate-DCM-hexane (2:9:9) as eluant affording the product as a white solid. (306 mg, 39%).

d. (R/S)-3-(1-adamantyl)methyl]-1-benzyl-4-(2-benzyloxycarbonyl)ethylcarbonyl-2,7-dioxo-2,3,4,5,6,7-hexahydro-1H-1,4-benzodiazonine Ozone was bubbled through a solution of (R/S)1-(1-adamantyl)methyl-9-benzyl-2-(2-benzyloxycarbonyl) ethylcarbonyl-1,2,3,4-tetrahydro-9H-pyrido[3,4-b]indole (300 mg, 0.5 mmol) in methanol (40 ml) at −78° C. until a blue colour persisted. Nitrogen was then bubbled through the solution until clear, followed by the addition of dimethyl sulphide (0.5 ml, 6.8 mmol). The solution was allowed to warm to room temperature and stirring continued for a further 2 hours, followed by evaporation to dryness. The crude product was purified by flash chromatography on silica gel with ethyl acetate-DCM (1:9) as eluant, affording the product as a colourless oil (200 mg, 64%)

e. (R/S)-3-(1-adamantyl)methyl-1-benzyl-4-(2-carboxy)ethylcarbonyl)-2,7-dioxo-2,3,4,5,6,7-hexahydro-1H-1,4-benzodiazonine (R/S)-3-(1-adamantyl)methyl-1-benzyl-4-(2-benzyloxycarbonyl)ethylcarbonyl)-2,7-dioxo-2,3,4,5,6,7-hexahydro-1H-1,4-benzodiazonine (200 mg, 0.32 mmol) was stirred under an atmosphere of hydrogen in the presence of 10% palladium on charcoal (50 mg) in methanol-tetrahydrofuran (20 ml/1:1) at room temperature for one hour. The reaction mixture was filtered through a pad of celite and evaporated to dryness affording the product as a white amorphous solid. (153 mg, 88%).

(d$^6$-DMSO) $\delta_H$ 0.60–0.98 (2H, m), 1.21–1.38 (4H, m), 1.50–1.62 (8H, m), 1.87–2.01 (5H, m), 2.02–2.32 (2H, m), 2.51–2.98 (2H, m), 3.65 (0.5H, m), 3.81–4.16 (4H, m), 4.55 (0.5H, m), 4.95 (0.5H, m), 5.20–5.40 (1H, m), 5.72 (1H, d), 6.83 and 6.95 (1H, 2×d), 7.05–7.58 (8H, m).

The compound was further characterised and tested as the N-methyl-D-glucamine salt.

Found: C, 60.41; H 7.86; N 5.26. C$_{40}$H$_{55}$N$_3$O$_{10}$. 3.0 H$_2$O requires C, 60.67; H, 7.76; N 5.30%

EXAMPLE 34

Preparation of (R/S)-4-acetyl-3-(1-adamantyl) methyl-1-benzyl-2,7-dioxo-2,3,4,5,6,7-hexahydro-1H-1,4-benzodiazonine The compound was prepared by an identical route to that used in the preparation of example 33 except that acetyl chloride was used in step b in place of succinic anhydride.

(CDCl$_3$) $\delta_H$ 0.86 (1H, d), 1.14 (1.5H, s), 1.38 (3H, d), 1.59–1.75 (11H, m), 1.95 (3H, m), 2.45–2.79 (2H, m), 2.99–3.30 (1.5H, m), 3.45–3.80 (1H, m), 4.03 (1H, dd), 4.26 (0.5H, m), 5.05 (0.5H, m), 5.22 and 5.51 (1H, d), 6.78 and 6.98 (1H, 2×d), 7.09–7.17 (2H, m), 7.27 (3H, m), 7.42–7.51 (2H, m), 7.71 and 7.80 (1H, d×2).

Found: C, 77.03; H, 7.51; N, 5.65. C$_{31}$H$_{36}$N$_2$O$_3$ requires C, 76.83; H, 7.49; N, 5.78%

EXAMPLE 35

Preparation of (R/S)-3-(1-adamantyl)methyl-1-(3-amino)benzyl-4-carboxymethylcarbonyl-2,7-dioxo-2,3,4,5,6,7-hexahydro-1H-1,4-benzodiazonine The compound was prepared by an identical route to that used in the preparation of example 33 except that malonic acid mono-4-nitrobenzyl ester was used in step b in place of succinic anhydride and 3-nitrobenzyl bromide subsequently used in place of benzyl bromide in step c.

(d$^6$-DMSO) $\delta_H$ 1.35–1.55 (15H, s), 1.72–1.79 (4H, m), 3.43–3.55 (1H, q), 4.07 (1H, m), 4.70 (2H, dd), 5.40 (2H, dd), 5.64 (1H, d), 6.16 (2H, d), 6.22 (1H, s), 6.43 (1H, d), 6.92 (1H, t), 7.38 (1H, t), 7.60 (2H, m), 8.22 (3H, d).

The compound was further characterised and tested as the N-methyl-D-glucamine salt.

Found: C, 62.09; H, 7.37; N 7.5 1. C$_{39}$H$_{54}$N$_4$O$_{10}$. 1.0 H$_2$O requires C, 61.89; H, 7.46; N 7.40%

EXAMPLE 36

Preparation of (3S,5R)-4-acetyl-3-(1-adamantyl) methyl-1-benzyl-5-carboxymethylaminocarbonyl-2,7-dioxo-2,3,4,5,6,7-hexahydro-1H-1,4-benzodiazonine a. (3S,5R)-4-acetyl-3-(1-adamantyl)methyl-1-benzyl-2,7-dioxo-2,3,4,5,6,7-hexahydro-1H-1,4-benzodiazonine-5-caboxylate The compound was prepared by an identical route to that used in the preparation of example 11 except that D-tryptophan benzyl ester was used in step a in place of L-tryptophan benzyl ester.

b. (3S,5R)-4-acetyl-3-(1-adamantyl)methyl-1-benzyl-5-carboxymethylaminocarbonyl-2,7-dioxo-2,3,4,5,6,7-hexahydro-1H-1,4-benzodiazonine The compound was prepared by an identical route to that used in the preparation of example 22 except that (3S,5R)-4-acetyl-3-(1-adamantyl)methyl-1-benzyl-2,7-dioxo-2,3,4,5,6,7-hexahydro-1H-1,4-benzodiazonine-5-carboxylate was used in step a in place of (3R,5S)-4-acetyl-3-(1-adamantyl) methyl-1-benzyl-2,7-dioxo-2,3,4,5,6,7-hexahydro-1H-1,4-benzodiazonine-5-carboxylate.

$[\alpha]^D$=+67.0° (C=1.0%, MeOH)

(d$^6$-DMSO) $\delta_H$ 1.04 (3H, s), 1.27 (4H, d), 1.45–1.57(8H, m), 1.86 (3H, s), 2.31 (1H, t), 2.89 (1H, dd), 3.62–3.75 (3H, m), 3.89–3.99 (3H, m), 5.35 (1H, d), 7.00 (1H, m), 7.21–7.30 (5H, m), 7.38 (1H, t), 7.50 (3H, m).

The compound was further characterised and tested as the N-methyl-D-glucamine salt.

Found: C, 60.42; H 7.32; N, 7.20. C$_{41}$H$_{56}$N$_4$O$_{11}$. 2H$_2$O requires C, 60.28; H, 7.40; N, 6.86%

EXAMPLE 37

Preparation of (3R,5S)-4-acetyl-3-(1-adamantyl) methyl-1-benzyl- 5-methoxycarbonylmethylaminocarbonyl-2,7-dioxo-2,3,4,5,6,7-hexahydro-1H-1,4-benzodiazonine The compound was prepared by an identical route to that used in the preparation of example 22 except that glycine methyl ester hydrochloride was used in step a place of glycine benzyl ester p-toluenesulphonate.

(CDCl$_3$) $\delta_H$ 1.15 (3H, s), 1.40–1.74(13H, m), 1.74 (3H, s), 2.70 (1H, t), 3.09 (1H, dd), 3.76 (3H, m), 3.90 (1H, d), 4.00–4.10 (4H, m), 5.60 (1H, d), 6.30 (1H, t), 6.77 (1H, d), 7.23–7.45 (8H, m).

Found: C, 69.22; H 7.02; N, 6.76. C$_{35}$H$_{41}$N$_3$O$_6$. 0.5H$_2$O requires C, 69.06; H, 6.95; N, 6.90%

EXAMPLE 38

Preparation of (3R,5S)-4-acetyl-1-benzyl-5-carboxymethylaminocarbonyl-3-(3,3-dimethyl) propyl-2,7-dioxo-2,3,4,5,6,7-hexahydro-1H-1,4-benzodiazonine a. (3R,5S)-4-acetyl-1-benzyl-3-(3,3-dimethyl) propyl-2,7-dioxo-2,3,4,5,6,7-hexahydro-1H-1,4-benzodiazonine-5-carboxylate The compound was prepared by an identical route to that used in the preparation of example 11 except that 3,3-dimethylbutyraldehyde was used in step a in place of 1-adamantylacetaldehyde.

b. (3R,5S)-4-acetyl-1-benzyl-5-carboxymethylaminocarbonyl-3-(3,3-dimethyl) propyl-2,7-dioxo-2,3,4,5,6,7-hexahydro-1H-1,4-benzodiazonine The compound was prepared by an identical route to that used in the preparation of example 22 except that (3R,5S)-4-acetyl-1-benzyl-3-(3,3-dimetyl)propyl-2,7-dioxo-2,3,4,5,6,7-hexahydro-1H-1,4-benzodiazonine-5-carboxylate was used in step a in place of (3R,5S)-4-acetyl-3-(1-adamantyl) methyl-1-benzyl-2,7-dioxo-2,3,4,5,6,7-hexahydro-1H-1,4-benzodiazonine-5-carboxylate.

(d$^6$-DMSO) $\delta_H$ 0.84 (9H, s), 1.05 (3H, s), 1.56 (1H, d), 2.48(1H, m), 2.90 (1H, dd), 3.61 (3H, m), 3.96 (3H, m), 5.43 (1H, d), 6.97 (1H, m), 7.12–7.47 (9H, m).

The compound was further characterised and tested as the N-methyl-D-glucamine salt.

Found: C, 53.63; H 7.79; N, 6.85. C$_{36}$H$_{52}$N$_4$O$_{11}$. 5H$_2$O requires C, 53.59; H, 7.74; N, 6.94%

EXAMPLE 39

Preparation of (3R,5S)-4-acetyl-1-benzyl-5-carboxymethylaminocarbonyl-3-cycloheptylmethyl-2,7-dioxo-2,3,4,5,6,7-hexahydro-1H-1,4-benzodiazonine The compound was prepared by an identical route to that used in the preparation of example 38 except that (3R,5S)-4-acetyl-1-benzyl-3-cycloheptylmethyl-2,7-dioxo-2,3,4,5,6,7-hexahydro-1H-1,4-benzodiazonine-5-carboxylate was used in step b in place of (3R,5S)-4-acetyl-1-benzyl-3-(3,3-dimethyl)propyl-2,7-dioxo-2,3,4,5,6,7-hexahydro-1H-1,4-benzodiazonine-5-carboxylate.

(d$^6$-DMSO) $\delta_H$ 1.10 (3H, s), 1.26–1.62(13H, m), 2.45(1H, m), 3.07(1H, m), 3.92–4.16(6H, m), 5.66(1H, d), 6.62 (1H, t), 6.73 (1H, d), 7.20–7.43 (8H, m).

The compound was further characterised and tested as the N-methyl-D-glucamine salt.

Found: C, 53.74; H 7.88; N, 6.72. C$_{39}$H$_{56}$N$_4$O$_{11}$. 5H$_2$O requires C, 54.16; H, 7.92; N, 6.48%

EXAMPLE 40

Preparation of (3R,5S)-4-acetyl-1-benzyl- 5-carboxymethylaminocarbonyl-3-cyclohexylmethyl-2,7-dioxo-2,3,4,5,6,7-hexahydro-1H-1,4-benzodiazonine The compound was prepared by an identical route to that used in the preparation of example 38 except that (3R,5S)-4-acetyl-1-benzyl-3-cyclohexylmethyl-2,7-dioxo-2,3,4,5,6, 7-hexahydro-1H-1,4-benzodiazonine-5-carboxylate was used in step b in place of (3R,5S)-4-acetyl-1-benzyl-3-(3,3-dimethyl)propyl-2,7-dioxo-2,3,4,5,6,7-hexahydro-1H-1,4-benzodiazonine-5-carboxylate.

(d$^6$-DMSO) $\delta_H$ 0.90–1.74 (12H, m), 1.17(3H, s), 2.45(1H, m), 3.07(1H, m), 3.93–4.15(6H, m), 5.66(1H, d), 6.62 (1H, t), 6.73 (1H, d), 7.20–7.43 (8H, m).

The compound was further characterised and tested as the N-methyl-D-glucamine salt.

Found: C, 52.97; H 7.65; N, 6.64. C$_{38}$H$_{54}$N$_4$O$_{11}$. 6.5H$_2$O requires C, 53.08; H, 7.85; N, 6.52%

EXAMPLE 41

Preparation of (3R,5S)-4-acetyl-3-(1-adamantyl) methyl-1-benzyl-5-methanesulphonamidocarboxymethylaminocarbonyl-2,7-dioxo-2,3,4,5,6,7-hexahydro-1H-1,4-benzodiazonine.

Methanesulphonamide (540 mg, 5.7 mmol) was added to a solution of (3R,5S)-4-acetyl-3-(1-adamantyl)methyl-1-benzyl-5-carboxymethylaminocarbonyl-2,7-dioxo-2,3,4,5, 6,7-hexahydro-1H-1,4-benzodiazonine (310 mg, 0.52 mmol), EDC (109 mg, 0.57 mmol), 1-hydroxybenzotriazole (77 mg, 0.57 mmol), diisopropylethylamine (150 µl, 0.86 mmol), and DMAP (6 mg, 0.05 mmol), in dry DCM (20 ml) and the reaction mixture stirred at room temperature for 18 hours. The solution was diluted with DCM (30 ml), washed successively with 10% citric acid solution (2×40 ml), brine (2×40 ml) and dried (MgSO$_4$). Filtration and evaporation of the solvent gave the crude product as a yellow foam, which was purified by preparative reverse phase HPLC with acetonitrile-water as eluant. (148 mg, 43%)

R$_t$=16.8 min. (C$_{18}$, 55–70% MeCN—H$_2$O, over 20 mins with 0.1% TFA)

(d$^6$-DMSO) $\delta_H$ 1.06 (3H, s), 1.27–1.64 (13H, m), 1.87 (3H,s), 2.40 (1H, dd), 2.90 (1H, dd), 3.21 (3H, s), 3.74 (2H, m), 3.87–4.00 (4H, m), 5.34 (1H, d), 7.00 (1H, m), 7.21–7.30 (5H, m), 7.42–7.53 (4H, m), 11.48 (1H, s).

The compound was further characterised and tested as the sodium salt.

EXAMPLE 42

Preparationof4-benzyloxycarbonyl-1-tert-butyloxycarbonylmethyl-2,7-dioxo-2,3 4,5,6,7-hexahydro-1H-1,4-benzodiazonine The compound was prepared by an identical route to that used in the preparation of example 1 except that benzyl-chloroformate was used in step d in place of 3-methylphenylisocyanate.

(CDCl$_3$) $\delta_H$ 1.47 (9H, s), 2.97–3.60 (3H, m), 3.81–4.45 (5H, m), 4.94 (2H, dd), 6.74 (2H, m), 7.15–7.70 (7H, m).

Found: C, 66.57; H 6.38; N, 6.23; C$_{25}$H$_{28}$N$_2$O$_6$ requires C, 66.36; H, 6.24; N, 6.19%

EXAMPLE 43

Preparation of 1-tert-butyloxycarbonyl-2,7-dioxo-4-phenoxycarbonylmethyl-2,3,4,5,6,7-hexahydro-1H-1,4-benzodiazonine The compound was prepared by an identical route to that used in the preparation of example 1 except that phenyl-chloroformate was used in step d in place of 3-methylphenylisocyanate.

(CDCl$_3$) $\delta_H$ 1.47 (9H, s), 2.88 and 3.48 (1H, 2×m), 3.05–3.30 (2H, m), 3.84 and 4.36 (1H, 2×m), 4.15 (2H, m), 4.79 and 5.08 (2H, 2×m), 7.19–7.58 (9H, m).

Found: C, 65.86; H, 6.10; N, 6.47. $C_{24}H_{26}N_2O_6$ requires C, 65.74; H, 5.98; N, 6.39%

EXAMPLE 44

Preparation of 1-benzyl-4-(3,4-dichlorophenyl) carbamyl-7-methyl-2-oxo-2,3,4,5,6,7-hexahydro-1H-1,4-benzodiazonine.

The compound was prepared by an identical route to that used in the preparation of example 10 except that 3,4-dichlorophenylisocyanate was used in step c in place of 3-methylphenylisocyanate.

(CDCl$_3$) $\delta_H$ 0.60 (3H, d, J=7 Hz), 1.38 and 1.89 (2H, 2×m), 2.08 and 2.61 (2H, 2×m), 3.27 and 4.19 (2H, 2×d, J=15 Hz), 4.24 (1H, m), 4.64 and 5.25 (2H, 2×d, J=14 Hz), 7.10–7.77 (12H, m), 9.80 (1H, s).

Found: C, 63.39; H 5.56; N, 8.38. $C_{26}H_{25}Cl_2N_3O_2$·0.5H$_2$O requires C, 63.55; H, 5.33; N, 8.55%

EXAMPLE 45

Preparation of 1-benzyl-7-methyl-4-(2-naphthyl) carbamyl-2-oxo-2,3,4,5,6,7-hexahydro-1H-1,4-benzodiazonine.

The compound was prepared by an identical route to that used in the preparation of example 10 except that 2-naphthylisocyanate was used in step c in place of 3-methylphenylisocyanate.

(CDCl$_3$) $\delta_H$ 0.60 (3H, d, J=7 Hz), 1.47 and 1.93 (2H, 2×m), 2.14 and 2.65 (2H, 2×m), 3.31 and 4.24 (2H, 2×d, J=15 Hz), 4.29 (1H, m), 4.61 and 5.27 (2H, 2×d, J=14 Hz), 7.14–7.42 (11H, m), 7.64 (1H, m), 7.78 (3H, m), 8.12 (1H, d, J=2 Hz), 9.80 (1H, s).

Found: C, 77.41; H 6.54; N, 9.18. $C_{30}H_{29}N_3O_2$ requires C, 77.75; H, 6.26; N, 9.07%

EXAMPLE 46

Preparation of 1-benzyl-4-(3-(benzyloxycarbonyl) phenylcarbamyl-2,7-dioxo-2,3,4,5,6,7-hexahydro-1H-1,4-benzodiazonine.

The compound was prepared by an identical route to that used in the preparation of example 3 except that (3-benzyloxycarbonyl)phenylisocyanate was used in step d in place of 3-methylphenylisocyanate.

(CDCl$_3$) $\delta_H$ 2.74 and 4.73 (2H, m), 3.00 (2H, m), 3.30 and 4.20 (2H, 2×d, J=15 Hz), 4.05 and 5.71 (2H, 2×d, J=14 Hz), 5.35 (2H, dd, J=12 Hz), 6.80 (1H, d), 7.27–7.50 (14H, m), 7.73 (2H, m), 8.13 (1H, m), 9.76 (1H, s).

Found: C, 77.41; H 6.54; N, 9.18. $C_{33}H_{29}N_3O_5$ requires C, 77.75; H, 6.26; N, 9.07%

EXAMPLE 47

Preparation of 1-benzyl-7-methyl-4-(3,5-dicarboxyphenyl)carbamyl-2-oxo-2,3,4,5,6,7-hexahydro-1H-1,4-benzodiazonine.

a. 1-benzyl-7-methyl-4-(3,5-dibenzyloxycarbonyl) phenylcarbamyl-2-oxo-2,3,4,5,6,7-hexahydro-1H-1, 4-benzodiazonine The compound was prepared by an identical route to that used in the preparation of example 10 except that 3,5-dibenzyloxycarbonylphenylisocyanate was used in step c in place of 3-methylphenylisocyanate.

b. 1-benzyl-7-methyl-4-(3,5-dicarboxyphenyl) carbamyl-2-oxo-2,3,4,5,6,7-hexahydro-1H-1,4-benzodiazonine.

1-benzyl-7-methyl-4-(3,5-dibenzyloxycarbonyl) phenylcarbamyl-2-oxo-2,3,4,5,6,7-hexahydro-1H-1,4-benzodiazonine (116 mg, 0.17 mmol) was stirred under a hydrogen atmosphere in the presence of 10% palladium on charcoal (20 mg) in methanol-THF(1:1/10 ml) at room temperature for 24 hours. The reaction mixture was filtered through a pad of celite and evaporated to dryness affording the product. (84 mg, 100%)

(d$^6$-DMSO) $\delta_H$ 0.51 (3H, d), 1.44 (1H, m), 1.83–2.01 (2H, m), 2.49(1H, m), 3.2(1H, m), 3.91(1H, bd), 4.32(1H, d), 4.63(1H, d), 5.26(1H, d), 7.16–7.42(9H, m), 8.09(1H, s), 8.22(2H, s), 9.82(1H, bs), 12.5(2H, bs)

The compound was further characterised and tested as the N-methyl-D-glucamine salt.

Found: C, 53.56; H, 6.95; N, 7.04. $C_{42}H_{61}N_5O_{16}$·3H$_2$O requires C, 53.33; H 7.09; N, 7.40%.

EXAMPLE 48

Preparation of 1-benzyl-7-methyl-4-(3-carboxyphenyl)carbamyl-2-oxo-2,3,4,5,6,7-hexahydro-1H-1,4-benzodiazonine.

a. 1-benzyl-7-methyl-4-(3-ethyloxycarbonyl) phenylcarbamyl-2-oxo-2,3,4,5,6,7-hexahydro-1H-1, 4-benzodiazonine The compound was prepared by an identical route to that used in the preparation of example 10 except that 3-ethyloxycarbonylphenylisocyanate was used in step c in place of 3-methylphenylisocyanate.

b. 1-benzyl-7-methyl-4-(3-carboxyphenyl)carbamyl-2-oxo-2,3,4,5,6,7-hexahydro-1H-1,4-benzodiazonine A solution of 1-benzyl-7-methyl-4-(3-ethyloxycarbonyl) phenylcarbamyl-2-oxo-2,3,4,5,6,7-hexahydro-1H-1,4-benzodiazonine(244 mg, 0.5 mmol), in 1M LiOH (2 ml) and THF (2 ml) was stirred at room temperature for 20 hours. The reaction mixture was diluted with 2M HCl (4 ml), extracted with chloroform (3×10 ml), and the combined extracts dried (MgSO$_4$). Filtration and evaporation of the solvent gave the crude product which was purified by flash chromatography on silica gel with methanol-DCM (1:9) as eluant. (197 mg, 86%).

(d$^6$-DMSO) $\delta_H$ 0.57 (3H, d), 1.25–1.42(1H, m), 1.86–1.95(1H, m), 2.10–2.19(1H, m), 2.60–2.66(1H, m), 3.29(1H, d), 4.19–4.31(2H, m), 4.59(1H, d), 5.26(1H, d), 7.12–7.44(10H, m), 7.77–7.84(2H, m), 8.22(1H, s), 9.80 (1H, s).

The compound was further characterised and tested as the N-methyl-D-glucamine salt.

Found: C, 58.86; H, 6.92; N, 8.28. $C_{24}H_{44}N_4O_9$·2.2H$_2$O requires C, 59.04; H 7.04; N, 8.10%.

EXAMPLE 49

Preparation of 1-tert-butyloxycarbonylmethyl-4-(3-methylphenyl)carbamyl-2-oxo-2,3,4,5,6,7-hexahydro-1H-1,4-benzodiazonine a. 2-nitrocinnamyl alcohol Sodium borohydride (1.15 g, 31.1 mmol) was added portionwise to an ice cooled suspension of trans-2- nitrocinnamaldehyde (5.00 g, 28.2 mmol), and cerium (III) chloride (12.61 g, 33.8 mmol) in methanol (140 ml). After stirring at room temperature for 30 minutes the mixture was poured into saturated aqueous NH$_4$Cl (200 ml), extracted with DCM (3×150 ml) and the extacts dried (MgSO$_4$). Filtration and evaporation of the solvent gave the product. (5.03 g, 100%)

b. 2-(3-tert-butyldimethylsilyloxyprop-2-enyl) nitrobenzene

Tert-butyldimethylchlorosilane (5.10 g, 33.8 mmol) was added to a solution of 2-nitrocinnamyl alcohol (5.05 g, 28.2 mmol) and imidazole (2.88 g, 42.3 mmol) in DMF (100 ml). After stirring at room temperature for 18 hours the reaction mixture was partitioned between water (200 ml) and ethyl acetate (200 ml). The organic layer was separated washed with brine (2×m 100 ml) and dried (MgSO$_4$). Filtration and evaporation of the solvent gave the crude product which was purified by flash chromatography on silica gel with ethyl acetate-hexane (1:3) as eluant. (7.82 g, 95%).

c. 2-(3-tert-butyldimethylstlyloxypropyl)aniline

A suspension of 2-(3-tert-butyldimethylsiiyloxyprop-2-enyl)nitrobenzene (7.82 g, 26.7 mmol), and 10% palladium on charcoal (0.8 g) in methanol (100 ml) was stirred under a hydrogen atmosphere for 5 hours. The reaction mixture was filtered through a pad of celite and the filtrate evaporated to give the crude product, which was purified by flash chromatography on silica gel with ethyl acetate-hexane (1:8) as eluant. (6.65 g, 94%)

d. N-(Benzyloxycarbonylaminomethylcarbonyl)-2-(3-tert-butyldimethyl-silyloxypropyl)aniline A solution of 2-(3-tert-butyldimethylsilyloxypropyl)aniline (4.42 g, 15.9 mmol) EDC (3.36 g, 17.5 mmol), HOBt (2.37 g, 17.5 mmol) and Z-glycine (4.99 g, 23.9 mmol) in DMF (50 ml) was stirred at room temperature for 20 hours. The reaction mixture was diluted with water (150 ml), and extracted with ethyl acetate (200 ml). The extract was washed with saturated aqueous sodium bicarbonate solution (200 ml), brine (2×150 ml) and dried (MgSO$_4$). Filtration and evaporation of the solvent gave the crude product which was purified by flash chromatography on silica gel with ethyl acetate-hexane (2:3) as eluant. (6.76 g, 93%).

e. N-(Benzyloxycarbonylaminomethylcarbonyl)-N-(tert-butyloxycarbonylmethyl)-2-(3-tert-butyldimethylsilyloxypropyl)aniline Sodium hydride (60% dispersion in oil/652 mg, 16.3 mmol) was added to a solution of N-(benzyloxycarbonylaminomethylcarbonyl)-2-(3-tert-butyidimethylsilyloxy-propyl)aniline (6.76 g, 14.8 mmol) in DMF (30 ml). After stirring at room temperature for 1 hour, tert-butylbromo acetate (2.19 ml, 14.8 mmol) was added and stirring continued at room temperature for 1 hour. The reaction mixture was diluted with water (150 ml) and extracted with ethyl acetate (2×150 ml). The organic extract was washed with brine (2×150 ml) and dried (MgSO$_4$). Filtration and evaporation of the solvent gave the crude product which was purified by flash chromatography with ethyl acetate-hexane (1:3) as eluant. (3.87 g, 46%)

f. N-(Benzyloxycarbonylaminomethylcarbonyl)-N-(tert-butyloxycarbonylmethyl)-2-(3-hydroxypropyl) aniline Tetrabutylammonium fluoride (1.0M in THF/10 ml, 10 mmol) was added to a solution of N-(benzyloxycarbonylaminomethylcarbonyl)-N-(tert-butyloxycarbonyl-methyl)-2-(3-tert-butyldimethylsilyloxypropyl)aniline(3.87 g, 6.8 mmol) in THF (25 ml) at room temperature. After stirring for 90 minutes the reaction mixture was diluted with ethyl acetate (150 ml), washed with water (150 ml), brine (150 ml) and dried (MgSO$_4$). Filtration and evaporation of the solvent gave the crude product which was purified by flash chromatography on silica gel with ethyl acetate-hexane (2:1) as eluant (2.39 g, 77%).

g. N-(Benzyloxycarbonylaminomethylcarbonyl)-N-(tert-butyloxycarbonylmethyl)-2-(3-(4-methyl) phenylsulphonyloxypropyl)aniline para-Toluenesulphonyl chloride (1.33 g, 6.98 mmol) was added in a single portion to a solution of N-(benzyloxycarbonylaminomethylcarbonyl)-N-(tert-butyloxycarbonylmethyl)-2-(3-hydroxypropyl)aniline (2.12 g, 4.66 mmol), DMAP (132 mg, 1.08 mmol) and triethylamine (1.51 ml, 10.85 mmol) in DCM (10 ml). After stirring at room temperature for 1 hour the mixture was diluted with DCM (100 ml), washed with water (100 ml), 10% citric acid solution (100 ml), saturated aqueous sodium bicarbonate solution (100 ml) and dried (MgSO$_4$). Filtration and evaporation of the solvent gave the crude product which was purified by flash chromatography on silica gel with ethyl acetate-hexane (2:3) as eluant. (2.12 g, 75%).

h. 1-tert-Butyloxycarbonylmethyl-4-benzyloxycarbonyl-2-oxo-2,3,4,5,6,7-hexahydro-1H-1,4-benzodiazonine Sodium hydride (60% dispersion in mineral oil/167 mg, 4.12 mmol) was added in a single portion to a solution of N-(benzyloxycarbonylaminomethylcarbonyl)-N-(tert-butyloxycarbony(methyl)- 2-(3-(4-methyl) phenyisulphonyloxypropyl)aniline (2.12 g, 3.48 mmol) in DMF (40 ml) at room temperature. After stirring for 16 hours the mixture was partitioned between water (100 ml) and ethyl acetate (100 ml). The organic layer was separated washed with brine (3×100 ml) and dried (MgSO$_4$). Filtration and evaporation of the solvent gave the product. (1.52 g, 100%).

i. 1-tert-Butyloxycarbonylmethyl-2-oxo-2,3,4,5,6,7-hexahydro-1H-1,4-benzodiazonine A suspension of 1-tert-butyloxycarbonylmethyl-4-benzyloxycarbonyl-2-oxo-2,3,4,5,6,7-hexahydro-1H-1,4-benzodiazonine(1.52 g, 3.48 mmol), and 10% palladium on charcoal (0.2 g) in methanol (20 ml) was stirred under a hydrogen atmosphere for 4 hours. The reaction mixture was filtered through a pad of celite and the filtrate evaporated to give the crude product, which was purified by flash chromatography on silica gel with methanol-DCM(1:12) as eluant. (996 mg, 95%)

j. 1-tert-Butyloxycarbonylmethyl-(3-methylphenyl) carbamyl-2-oxo-2,3,4,5,6,7-hexahydro-1H-1,4-benzodiazonine A solution of 1-tert-butyloxycarbonylmethyl-2-oxo-2,3,4,5,6,7-hexahydro-1H-1,4-benzodiazonine (438 mg, 1.44 mmol) and m-tolylisocyanate (0.2 ml, 1.6 mmol) in DCM (4 ml) was stirred at room temperature for 90 minutes. Evaporation of the solvent gave the crude product which was purified by flash chromatography on silica gel with ethyl acetate-hexane (1:2) as eluant. (550 mg, 87%)

(CDCl$_3$) $\delta_H$1.51(9H,s), 1.76 and 2.10(1H,m), 2.26 and 4.30(1H,m), 2.33(3H,s),2.66–2.87(2H,m), 3.39 and 4.15 (1H,2×d), 3.79 and 4.65(1H,2×d), 6.82(1H,m), 7.14 7.50 (7H,m), 9.17(1H,bs)

Found: C, 68.71; H, 7.18; N, 9.42. C$_{25}$H$_{31}$N$_3$O$_4$. requires C, 68.63; H 7.14; N, 9.60%

EXAMPLE 50

Preparation of 1-benzyl-7-phenyl-4-(3-methylphenyl)carbamyl-2-oxo-2,3,4,5,6,7-hexahydro-1H-1,4-benzodiazonine a. N-Butyloxycarbonyl-2-benzylaniline

A solution of 2-benzylaniline (6.04 g, 33 mmol), and di-tert-butyldicarbonate (7.92 g, 36 mmol), in THF (30 ml) was heated at reflux for 2 hours. The reaction mixture was concentrated in vacuo and the residue partitioned between ethyl acetate (100 ml) and 10% citric acid solution (100 ml). The organic layer was separated and dried (MgSO$_4$). Filtration and evaporation of the solvent gave the product which was recrystallised from hexane (7.36 g, 79%).

b. N-Butyloxycarbonyl-2-(1-phenylprop-3-enyl)aniline n-Butyl lithium (1.6M in hexane/14 ml, 22 mmol) was added dropwise over 10 minutes to a solution of N-butyloxycarbonyl-2-benzylaniline (2.83 g, 10 mmol) in THF (40 ml) at −40° C. After stirring for 5 minutes allyl bromide (0.87 ml, 10 mmol) was added and the reaction mixture allowed to warm to room temperature, and stirring continued for 1 hour. The reaction mixture was partitioned between ethyl acetate (100 ml) and saturated aqueous NH$_4$Cl solution (100 ml). The organic layer was separated, washed with brine (100 ml) and dried (MgSO$_4$), filtered and evaporated to leave the product. (3.42 g, 100%)

c. N-butyloxycarbonyl-2-(3-hydroxy-1-phenylpropyl)aniline

Ozone was bubbled through a solution of N-butyloxycarbonyl-2-(1-phenylprop-3-enyl)aniline (3.42 g, 10 mmol) in methanol (30 ml) for 30 minutes at −78° C. The solution was then purged with nitrogen followed by the addition of sodium borohydride (925 mg, 25 mmol). After stirring for 10 minutes at −78° C., the reaction mixture was allowed to warm to room temperature and stirring continued for 16 hours. The reaction mixture was diluted with saturated aqueous NH$_4$Cl solution (150 ml), and extracted with ethyl acetate (2×100 ml). The extracts were washed with brine (100 ml) and dried (MgSO$_4$). Filtration and evaporation of the solvent gave the product which was purified by flash chromatography on silica gel with ethyl acetate-hexane (1:2 to 1:1) as eluant. (1.21 g 37%)

d. N-butyloxycarbonyl-2-(3-acetoxy1-phenylpropyl)aniline

Acetic anhydride (0.42 ml, 0.42 mmol) was added to a solution of N-butyloxycarbonyl-2-(3-hydroxy-1-phenylpropyl)aniline (1.21 g, 3.7 mmol), triethylamine (0.77 ml, 5.56 mmol) and DMAP (5 mg) in DCM (25 ml). After stirring at room temperature for 90 minutes the reaction mixture was diluted with DCM (25 ml), washed with 10% aqueous citric acid solution (40 ml), saturated aqueous sodium bicarbonate solution (40 ml) and dried (MgSO$_4$). Filtration and evaporation of the solvent gave the product. (1.39 g, 100%).

e. 2-(3-acetoxy-1-phenylpropyl)aniline

A solution of N-butyloxycarbonyl-2-(3-acetoxy1-phenylpropyl)aniline (1.39 g, 3.7 mmol) in CHCl$_3$-TFA (1:1/10 ml) was stirred at room temperature for 20 minutes. The reaction mixture was neutralised with saturated aqueous sodium bicarbonate solution (30 ml), extracted with DCM (3×30 ml) and the extracts dried (MgSO$_4$). Filtration and evaporation of the solvent gave the product. (939 mg, 94%)

f. 1-benzyl-7-thylphenyl)carbamyl-2-oxo-2,3,4,5,6,7-hexahydro-1H-1,4-benzodiazonine The compound was prepared by an identical route to that used in the preparation of example 49 except that 2-(3-acetoxy-1-phenylpropyl)aniline was used in place of 2-(3-tert-butyldimethylsilyloxypropyl)aniline in step d.

(CDCl$_3$) $\delta_H$ 1.99–2.08(2H,m), 2.35(3H,s), 2.73–2.76(2H, m), 3.36(1H,d). 4.20–4.49(4H,m), 5.51(2H,d), 6.86–7.39 (18H,m), 9.38(1H,s).

Found: C, 78.56; H, 6.47; N, 8.60. C$_{33}$H$_{33}$N$_3$O$_2$. requires C, 78.70; H 6.60; N, 8.34%

EXAMPLE 51

Preparation of 1-benzyl-7-ethyl-4-(3-methylphenyl) carbamyl-2-oxo-5,2,3,4,5,6,7-hexahydro-1H-1,4-benzodiazonine The compound was prepared by a similar method to that used in the preparation of example 50 except that 2-propyl aniline was used in place of 2-benzyl aniline in step a.

(CDCl$_3$) $\delta_H$0.71(3H,t), 1.15–1.57(3H,m), 1.90(1H,m), 2.18–2.35(4H,m), 2.60(1H,m), 3.27(1H,d), 4.21(1H,d), 4.26 (1H,m), 4.48(1H,d), 5.25(1H,d), 6.85–6.88(2H,m), 7.17–7.39(11H,m), 9.44(1H,s).

Found: C, 75.88; H, 7.09; N, 9.48. C$_{28}$H$_{31}$N$_3$O$_2$. requires C, 76.16; H 7.08; N, 9.52%

EXAMPLE 52

Preparation of 1-benzyl-7-ethyl-4-(3,4-dichlorophenyl)carbamyl-2-oxo-2,3,4,5,6,7-hexahydro-1H-1,4-benzodiazonine The compound was prepared by a similar method to that used in the preparation of example 49 except that 3,4-dichlorophenylisocyanate and 1-benzyl-7-ethyl-2-oxo-2,3, 4,5,6,7-hexahydro-1H-1,4-benzodiazonine were used in place of m-tolylisocyanate and 1-tert-butyloxycarbonylmethyl-2-oxo-2,3,4,5,6,7-hexahydro-1H-1,4-benzodiazonine respectively in step j.

(CDCl$_3$) $\delta_H$ 0.72(3H,t), 1.17–1.22(1H,m), 1.51(1H,m), 1.54–1.58(1H,m), 1H,m), 1.93–1.99(1H,m), 2.25–2.30(1H, m), 2.58–2.61(1H,m), 3.27(1H,d), 4.14(1H,d), 4.23–4.29 (1H,m), 4.44(1H, d), 5.27(1H,d), 6.86–6.89(1H,m), 7.21–7.43(10H,m), 7.76(1H,m), 9.72(I1H,s).

Found: C, 64.97; H, 5.52; N, 8.27. C$_{27}$H$_{27}$N$_3$Cl$_2$O$_2$. requires C, 65.32; H 5.48; N, 8.46%

EXAMPLE 53

Preparation of 1-benzyl-7-ethyl-4-(2-indolecarbonyl)-2-oxo-2,3,4,5,6,7-hexahydro-1H-1, 4-benzodiazonine A mixture of 1-benzyl-7-ethyl-2-oxo-2,3,4,5,6,7-hexahydro-1H-1,4-benzodiazonine (446 mg, 1.45 mmol), EDC (306 mg, 1.6 mmol), HOBt (215 mg, 1.6 mmol) and 2-indolecarboxylic acid (350 mg, 2.2 mmol) in DMF (5 ml) was stirred at room temperature for 18 hours. The reaction mixture was partitioned between water (50 ml) and ethyl acetate (50 ml). The organic layer was separated, washed with saturated aqueous NaHCO$_3$ solution (50 ml), brine (2×50 ml) and dried (MgSO$_4$). Filtration and evaporation of the solvent gave the crude product which was purifeid by flash chromatography on silica gel with ethyl acetate-hexane (1:2) as eluant. (479 mg, 73%)

(CDCl$_3$) δ0.77(3H,t), 1.19–1.29(1H,m), 1.56–1.65(2H, m), 2.18–2.24(2H,m), 2.63(1H,m), 3.50–3.52(1H,m), 4.47–4.65(3H,m), 5.31(1H,d), 6.86–7.68(14H,m), 12.0(1H, s)

Found: C, 76.86; H, 6.51; N, 9.27. Cl$_{29}$H$_{29}$N$_3$O$_2$. requires C, 77.13; H 6.47; N, 9.31%

EXAMPLE 54

Preparation of 1-benzyl-4-(3-methylphenyl) carbamyl-2-oxo-2,3,4,5,6,7-hexahydro-1H-1,4-benzodiazonine.

The compound was prepared by an identical route to that used in the preparation of example 49 except that Boc-glycine was used in place of Z-glycine in step d, and benzyl bromide was used in place of tert-butyl bromoacetate in step e.

CDCl$_3$) δ$_H$1.60 (1H, m), 1.97–2.31(4H, m), 2.36(3H, s), 3.32(1H, d), 4.16(1H, d), 421–4.29(1H,m), 4.74(1H, d), 4.98(1H, d), 6.82(1H, d), 7.02–7.38(12H,m), 9.51(1H, s).

Found: C, 75.24; H, 6.59; N, 10.23. C$_{26}$H$_{27}$N$_3$O$_2$. requires C, 75.52; H 6.58; N, 10.16%.

EXAMPLE 55

Preparation of 1-tert-butyloxycarbonylmethyl-4-(3-methoxyphenyl)carbamyl-2-oxo-2,3,4,5,6,7-hexahydro-1H-1,4-benzodiazonine The compound was prepared by a similar route to that used in the preparation of example 49 except that 3-methoxyphenylisocyanate was used in step j in place of 3-methylphenylisocyanate.

(CDCl$_3$) δ$_H$ 1.51(9H,s), 1.75 and 2.10(2H, 2×m), 2.30 and 4.32(2H,2×m), 2.71–2.86(2H,m), 3.39 and 4.15(2H,2×d), 3.78 and 4.64(2H,2×d), 3.81(3H,s), 6.54–6.59(1H, m), 7.00–7.08(1H,m), 7.14–7.50(6H,m), 9.28(1H,s).

Found: C, 66.19; H, 6.92; N, 9.28. C$_{25}$H$_{31}$N$_3$O$_5$. requires C, 66.21; H 6.89; N, 9.27%

EXAMPLE 56

Preparation of 1-carboxymethyl-4-(3-methylphenyl) carbamyl-2-oxo-2,3,4,5,6,7-hexahydro-1H-1,4-benzodiazonine A solution of 1-tert-butyloxycarbonylmethyl-4-(3-methylphenyl)carbamyl-2-oxo-2,3,4,5,6,7-hexahydro-1H-1, 4-benzodiazonine(408 mg, 0.93 mmol) in CHCl$_3$-TFA (5:1/ 12 ml) was stirred at room temperature for 16 hours. Evaporation of the solvent gave the product. (360 mg, 100%)

(d$^6$-DMSO) δ$_H$1.75–2.0(2H,m), 2.26(3H,s), 2.64–2.79 (1H,m), 3.49(1H, d), 3.88(1H, d), 4.04–4.11(2H, m), 4.74 (1H,d), 6.76(1H,m), 7.10–7.48(7H,m), 9.01(1H,s), 12.5(1H, bs).

The compound was further characterised and tested as the N-methyl-D-glucamine salt.

EXAMPLE 57

Preparation of 1-carboxymethyl-4-(3-methoxyphenyl)carbamyl-2-oxo-2,3,4,5,6,7-hexahydro-1H-1,4-benzodiazonine The compound was prepared by an identical route to that used in the preparation of examples 56 except that 1-tert-butyloxycarbonylmethyl-4-(3-methoxyphenyl)carbamyl-2-oxo-2,3,4,5,6,7-hexahydro-1H-1,4-benzodiazonine was used in place of 1-tert-butyloxycarbonylmethyl-4-(3-methylphenyl)carbamyl-2-oxo-2,3,4,5,6,7-hexahydro-1H-1, 4-benzodiazonine.

(d$^6$-DMSO) δ$_H$ 1.82–1.96(2H,m), 2.15 and 4.48(1H,2× m), 2.64–2.79(2H,m), 3.51(1H,d),3.71(3H,s),3.85(1H,d), 4.04–4.10(2H,m),4.48(1H,d),6.51–6.55(1H,m), 6.83–6.85 (1H,m), 7.06–7.17(2H,m)

The compound was further characterised and tested as the N-methyl-D-glucamine salt.

Found: C, 52.01; H, 7.02; N, 8.58. C$_{28}$H$_{40}$N$_4$O$_{10}$. 3H$_2$O requires C, 52.00; H 7.17; N, 8.66%

EXAMPLE 58

Preparation of(3R,5S)-4-acetyl-3-(1-adamantyl) methyl-1-(4-fluorobenzyl)-5-carboxymethylaminocarbonyl-2,7-dioxo-2,3,4,5,6,7-hexahydro-1H-1,4-benzodiazonine.

The compound was prepared by an identical route to that used to prepare example 22 except that (3R,5S)-4-acetyl-3-(1-adamantyl)methyl-1-(4-fluorobenzyl)-2,7-dioxo-2,3,4,5, 6,7-hexahydro-1H-1,4-benzodiazonine-5-carboxylate was used in step a in place of (3R,5S)-4-acetyl-3-(1-adamantyl) methyl-1-benzyl-2,7-dioxo-2,3,4,5,6,7-hexahydro-1H-1,4-benzodiazonine-5-carboxylate.

(CDCl$_3$) δ$_H$ 1.08(1H,d), 1.23(3H,s), 1.20–1.73(12H,m), 1.88(3H,s), 2.35(1H,m), 2.63(1H,t),3.31(1H,t),4.05(4H,m), 4.26(1H,d),5.26(1H,s),5.73(1H,d),6.72(1H,d),

The compound was further characterised and tested as the N-methyl-D-glucamine salt. 6.95(2H, m), 7.2(5H, m).

Found: C, 59.98; H, 7.21; N, 6.50. C$_{41}$H$_{55}$FN$_4$O$_{11}$.1.4H$_2$O requires C, 59.77; H 7.07; N, 6.80%

EXAMPLE 59

Preparation of(3R,5S)-4-acetyl-3-(1-adamantyl) methyl -1-(2-fluorobenzyl)-5-carboxymethyaminocarbonyl-2,7-dioxo-2,3,4,5,6,7-hexahydro-1H-1,4-benzodiazonine.

The compound was prepared by an identical route to that used to prepare example 22 except that (3R,5S)-4-acetyl-3-(1-adamantyl)methyl-1-(2-fluorobenzyl)-2,7-dioxo-2,3,4,5, 6,7-hexahydro-1H-1,4-benzodiazonine-5-carboxylate was used in step a in place of (3R,5S)-4-acetyl-3-(1-adamantyl) methyl-1-benzyl-2,7-dioxo-2,3,4,5,6,7-hexahydro-1H-1,4-benzodiazomine-5-carboxylate (CDCl$_3$) δ$_H$ 1.15(1H,m), 1.22(3H,s), 1.20–1.73(12H,m), 1.88(3H,s), 2.35(1H,dt), 2.64(1H,t), 3.07(1H,q), 4.03 and 4.35(4H,m), 4.10(1H,d), 5.40(1H,d), 6.37(1H,t), 7.04(3H, m), 7.24–7.47(5H,m).

The compound was further characterised and tested as the N-methyl-D-glucamine salt.

Found: C, 59.99; H, 7.03; N, 6.79. C$_{41}$H$_{55}$FN$_4$O$_{11}$.1.2H$_2$O requires C, 60.02; H 7.05; N, 6.83%

EXAMPLE 60

Preparation of (3R,5S)-4-acetyl-3-(1-adamantyl) methyl-1-(3-fluorobenzyl)-5-carboxymethylaminocarbonyl-2,7-dioxo-2,3,4,5,6,7-hexahydro-1H-1,4-benzodiazonine.

The compound was prepared by an identical route to that used to prepare example 22 except that (3R,SS)-4-acetyl-3-

(1-adamantyl)methyl-1-(3-fluorobenzyl)-2,7-dioxo-2,3,4,5,6,7-hexahydro-1H-1,4-benzodiazonine-5-carboxylate was used in step a in place of (3R,5S)-4-acetyl-3-(1-adamantyl)methyl-1-benzyl-2,7-dioxo-2,3,4,5,6,7-hexahydro-1H-1,4-benzodiazonine5-carboxylate.

(CDCl$_3$) δ1.10(1H,d), 1.24(3H,s), 1.20–1.90(12H,m), 1.90(3H,s), 2.37(1H,m), 2.64(1H,m), 3.63(1H,q), 4.02(4H,m), 5.77(1H,d), 6.76(1H,d), 7.03(3H,m), 7.20–7.35(5H,m).

The compound was further characterised and tested as the N-methyl-D-glucamine salt.

Found: C, 59.86; H, 7.18; N, 6.76. $C_{41}H_{55}FN_4O_{11}.1.3H_2O$ requires C, 59.89; H 7.06; N, 6.81%

EXAMPLE 61

Preparation of (+/−)-trans-4-acetyl-3-(1-adamantyl)methyl-1-benzyl-5-carboxymethylaminocarbonyl-2,7-dioxo-9-fluoro-2,3,4,5,6,7-hexahydro-1H-1,4-benzodiazonine.

a. (+/−)-trans-4-acetyl-3-(1-adamantyl)methyl1-benzyl-2,7-dioxo-2,3,4,5,6,7-hexahydro-1H-1,4-benzodiazonine-5-carboxylate The compound was prepared by an identical route to that used to prepare example 11 except that (R/S)-5-fluoro-tryptophan benzyl ester was used in step a in place of L-tryptophan benzyl ester.

b. (+/−)-trans-4-acetyl-3-(1-adamantyl)methyl-1-benzyl-5-carboxymethylaminocarbonyl-2,7-dioxo-9-fluoro-2,3,4,5,6,7-hexahydro-1H-1,4-benzodiazonine The compound was prepared by an identical route to that used to prepare example 22 except that (+/−)-trans-4-acetyl-3-(1-adamantyl)methyl-1-benzyl2,7-dioxo-2,3,4,5,6,7-hexahydro-1H-1,4-benzodiazonine-5-carboxylate was used in step a in place of (3R,5S)-4-acetyl-3-(1-adamantyl)methyl-1-benzyl-2,7-dioxo-2,3,4,5,6,7-hexahydro- 1H-1,4-benzodiazonine-5-carboxylate (CDCl$_3$) δ$_H$ 1.20(1H,d), 1.32(3H,s), 1.38(6H,d), 1.58(6H,q), 2.10(3H,s), 2.72(1H,dd), 3.05(1H,dd), 3.86(1H,d), 4.04(4H,m), 4.08(1H,d), 5.60(1H,d), 6.42(1H,t), 6.70(1H,q), 7.03 and 7.20(1H,m), 7.27(2H,m), 7.30(3H,m).

The compound was further characterised and tested as the N-methyl-D-glucamine salt.

Found: C, 57.71; H, 6.96; N, 6.90. $C_{41}H_{55}FN_4O_{11}.1.35H_2O$ requires C, 59.81; H 7.06; N, 6.81%

EXAMPLE 62

Preparation of (3R,5S)-4-acetyl-3-(1-adamantyl)methyl-1-(3-chlorobenzyl)-5-carboxymethylaminocarbonyl-2,7-dioxo-2,3,4,5,6,7-hexahydro-1H-1,4-benzodiazonine.

The compound was prepared by an identical route to that used to prepare example 22 except that (3R,5S)-4-acetyl-3-(1-adamantyl)methyl-1-(3-chlorobenzyl)-2,7-dioxo-2,3,4,5,6,7-hexahydro-1H-1,4-benzodiazonine-5-carboxylate was used in step a in place of (3R,5S)-4-acetyl-3-(1-adamantyl)methyl-1-benzyl-2,7-dioxo-2,3,4,5,6,7-hexahydro-1H-1,4-benzodiazonine-5-carboxylate (CDCl$_3$) δ$_H$ 1.20(3H,d), 1.36(2H,s), 1.53–1.82(10H,m), 1.95(3H,s), 2.72(1H,t), 3.10(1H,d), 3.88(1H,d), 4.00–4.13(4H,m), 5.63(1H,d), 6.53(1H,bs), 6.84(1H,d), 7.10(1H,d), 7.10–7.51(6H,m).

The compound was further characterised and tested as the N-methyl-D-glucamine salt.

Found: C, 59.08; H, 6.92; N, 6.27. $C_{41}H_{55}ClN_4O_{11}.H_2O$ requires C, 59.10; H 6.89; N, 6.72%

EXAMPLE 63

Preparation of (3R,5S)-4-acetyl-3-(1-adamantyl)methyl-1-(2-chlorobenzyl)-5-carboxymethylaminocarbonyl-2,7-dioxo-2,3,4,5,6,7-hexahydro-1H- 1,4-benzodiazonine.

The compound was prepared by an identical route to that used to prepare example 22 except that (3R,5S)-4-acetyl-3-(1-adamantyl)methyl-1-(2-chlorobenzyl)-2,7-dioxo-2,3,4,5,6,7-hexahydro-1H-1,4-benzodiazonine-5-carboxylate was used in step a in place of (3R,5S)-4-acetyl-3-(1-adamantyl)methyl-1-benzyl-2,7-dioxo-2,3,4,5,6,7-hexahydro-1H-1,4-benzodiazonine-5-carboxylate (CDCl$_3$) δ$_H$1.25(6H,m), 1.40–1.74(12H,m), 1.95(3H,s), 2.69(1H,t), 3.10(1H,q),4.10–4.25(5H,m), 5.64(1H,d), 6.46(1H,bs), 6.86(1H,d), 7.10(1H,t), 7.10–7.42(6H,m).

The compound was further characterised and tested as the N-methyl-D-glucamine salt.

Found: C, 60.09; H, 6.74; N, 6.74. $C_{41}H_{55}ClN_4O_{11}$ requires C, 60.40; H 6.80; N, 6.87%

EXAMPLE 64

Preparation of (3R,5S)-4-acetyl-3-(1-adamantyl)methyl-1-(2-fluorobenzyl)-5-[(1S)-carboxy]ethylaminocarbonyl-2,7-dioxo-2,3,4,5,6,7-hexahydro-1H-1,4-benzodiazonine The compound was prepared by an identical route to that used to prepare example 24 except that (3R,5S)-4-acetyl-3-(1-adamantyl)methyl-1-(2-fluorobenzyl)-2,7-dioxo-2,3,4,5,6,7-hexahydro-1H-1,4-benzodiazonine-5-carboxylate was used in step a in place of (3R,5S)-4-acetyl-3-(1-adamantyl)methyl-1-benzyl-2,7-dioxo-2,3,4,5,6,7-hexahydro-1H-1,4-benzodiazonine-5-carboxylate (CDCl$_3$) δ$_H$ 1.10(1H,d), 1.21(3H,s), 1.28–1.70(13H,s), 1.89(3H,s), 2.70(1H,t), 3.05(1H,d), 4.00–4.20(3H,m), 4.25(1H,d), 4.52(1H,t), 5.45(1H,d), 6.43(1H,d), 7.07(3H,m), 7.27–7.45(6H,m).

Found: C, 60.71; H, 7.70; N, 6.66. $C_{42}H_{57}FN_4O_{11}.H_2O$ requires C, 60.68; H 7.15; N, 6.74%

EXAMPLE 65

Preparation of (3R,5S)-4-acetyl-3-(1-adamantyl)methyl-1-(2-fluorobenzyl)-5-methanesulphonamidocarboxymethylaminocarbonyl-2,7-dioxo-2,3,4,5,6,7-hexahydro-1H-1,4-benzodiazonine The compound was prepared by an identical route to that used to prepare example 41 except that (3R,5S)-4-acetyl-3-(1-adamantyl)methyl-1-(2-fluorobenzyl)-5-carboxymethylaminocarbonyl-2,7-dioxo-2,3,4,5,6,7-hexahydro 1H-1,4-benzodiazonine was used in place of (3R,5S)-4-acetyl-3-(1-adamantyl)methyl-1-benzyl-5-carboxymethylaminocarbonyl-2,7-dioxo-2,3,4,5,6,7-hexahydro-1H-1,4-benzodiazonine (CDCl$_3$) δ$_H$ 1.20(1H,d), 1.24(3H,s), 1.21–1.67(12H,m), 1.83(3H,s), 2.60(1H,dd), 3.11(1H,dd), 3.22(3H,s), 3.90(2H,m), 4.10(3H,m), 4.20(1H,d), 5.35(1H,d), 6.45(1H,s), 7.04(3H,m), 7.33(3H,m), 7.44(3H,m).

The compound was further characterised and tested as the sodium salt.

Found: C, 58.20; H, 5.76; N, 7.82. $C_{35}H_{40}FN_4O_7SNa \cdot H_2O$ requires C, 58.30; H 5.87; N, 7.77%

EXAMPLE 66

Preparation of (3R,5S)-4-acetyl-3-(1-adamantyl)methyl-1-(2-fluorobenzyl)-5-[(1S)-methanesulphonamidocarboxy]ethylaminocarbonyl-2,7-dioxo-2,3,4,5,6,7-hexahydro-1H-1,4-benzodiazonine The compound was prepared by an identical route to that used to prepare example 41 except that (3R,5S)-4-acetyl-3-(1-adamantyl)methyl-1-(2-fluorobenzyl)-5-[(1S)-carboxy]ethylaminocarbonyl-2,7-dioxo-2,3,4,5,6,7-hexahydro-1H-1,4-benzodiazonine was used in place of (3R,5S)-4-acetyl-3-(1-adamantyl)methyl-1-benzyl-5-carboxymethylaminocarbonyl-2,7-dioxo-2,3,4,5,6,7-hexahydro-1H-1,4-benzodiazonine (CDCl$_3$) $\delta_H$ 1.00(1H,d), 1.20–1.26(3H,d), 1.32–1.72(12H,m), 1.90(3H,s), 2.63(1H,t), 3.00(1H,2×dd), 3.25(3H,s), 3.80–4.24(5H,m), 5.40(2H,m), 5.80(1H,bs), 6.25(1H,bs), 7.03(3H,m), 7.27–7.37(4H,m), 7.44–7.48(2H,m), 9.38 and 9.69(1H,2 x s).

The compound was further characterised and tested as the sodium salt.

Found: C, 59.99; H, 5.93; N, 7.86. $C_{36}H_{42}FN_4O_7SNa$ requires C, 60.32; H 5.91; N, 7.82%

EXAMPLE 67

Preparation of (3R,5S)-4-acetyl-3-(1-adamantyl)methyl-1-benzyl-5-tetrazolomethylaminocarbonyl-2,7-dioxo-2,3,4,5,6,7-hexahydro-1H-1,4-benzodiazonine a. (3R,5S)-4-acetyl-3-(1-adamantyl)methyl-1-benzyl-5-N-pivaloyloxymethyl-(5-tetrazolo)methylaminocarbonyl-2,7-dioxo-2,3,4,5,6,7-hexahydro-1H-1,4-benzodiazonine The compound was prepared by an identical route to that used in the preparation of example 24 except that 5-(N-pivaloyloxymethyl)tetrazolmethylamine was used in place of L-alanine benzyl ester.

b. (3R,5S)-4-acetyl-3-(1-adamantyl)methyl-1-benzyl-5-(5-tetrazolo)methylaminocarbonyl-2,7-dioxo-2,3,4,5,6,7-hexahydro-1H-1,4-benzodiazonine A solution of methylamine in IMS (33% w/w; 0.1 ml) was added to a solution of (3R,5S)4-acetyl-3-(1-adamantyl)methyl-1-benzyl-5-N-pivaloyloxymethyl-(5-tetrazolo)methylaminocarbonyl-2,7-dioxo-2,3,4,5,6,7-hexahydro-1H-1,4-benzodiazonine (210 mg, 0.3 mmol) in methanol-DCM (1:8/2.25 ml) at room temperature. After stirring for 17 hours the reaction mixture was diluted with DCM (20 ml), washed with 5% aqueous KHSO$_4$ solution (20 ml), brine (20 ml), and dried (Na$_2$SO$_4$). Filtration and evaporation of the solvent gave the crude product, which was purified by flash chromatography on silica gel with methanol-DCM (1:10) as eluant (123 mg, 70%)

(d$^6$-DMSO) $\delta_H$ 1.04(3H,s), 1.26–1.66(12H,m), 1.87(3H,m), 2.40(1H,t), 3.00(1H,dd), 3.90(1H,m), 3.95(3H,m), 4.40 (2H,d), 5.35(1H,d), 7.05(1H,m), 7.21–7.31(6H,m), 7.50–7.53(3H,m), 7.60(1H,t).

The compound was further characterised and tested as the sodium salt.

Found: C, 61.01; H, 6.12; N, 14.68. $C_{34}H_{38}N_7O_4Na \cdot 2H_2O$ requires C, 61.16; H 6.34; N, 14.68%

EXAMPLE 68

Preparation of (3R,5S)-4-acetyl-3-(1-adamantyl)methyl-1-(2-fluorobenzyl)-5-(5-tetrazolo)methylaminocarbonyl-2,7-dioxo-2,3,4,5,6,7-hexahydro-1H-1,4-benzodiazonine The compound was prepared by an identical route to that used in the preparation of example 67 except that (3R,5S)-4-acetyl-3-(1-adamantyl)methyl-1-(2-fluorobenzyl)-5-(5-tetrazolo)methylaminocarbonyl-2,7-dioxo-2,3,4,5,6,7-hexahydro-1H-1,4-benzodiazonine was used in place of (3R,5S)-4-acetyl-3-(1-adamantyl)methyl-1-benzyl-5-(5-tetrazolo)methylaminocarbonyl-2,7-dioxo-2,3,4,5,6,7-hexahydro-1H-1,4-benzodiazonine (d$^6$-DMSO) $\delta_H$ 1.06(3H,s), 1.22–1.63(12H,m), 1.83(3H,s), 2.35(1H,m), 2.95(1H,dd), 3.75(1H,m), 3.96(2H,m), 4.08(1H,d), 4.35(2H,m), 5.28(1H,d), 7.10(3H,m), 7.33(3H,m), 7.50(3H,m).

The compound was further characterised and tested as the sodium salt.

Found: C, 61.01; H, 6.12; N, 14.68. $C_{34}H_{38}N_7O_4Na \cdot 2H_2O$ requires C, 61.16; H 6.34; N, 14.68%

EXAMPLE 69

Preparation of (+/−)-trans-4-acetyl-3-(1-adamantyl)methyl-1-benzyl-5-carboxymethylaminocarbonyl-2,7-dioxo-9-methoxy-2,3,4,5,6,7-hexahydro-1H-1,4-benzodiazonine The compound was prepared by an identical route to that used to prepare example 61 except that (R/S)-5-methoxy-tryptophan benzyl ester was used in step a in place of (R/S)-5-fluoro-tryptophan benzyl ester (CDCl$_3$) $\delta_H$ 1.18(1H,d), 1.34(3H,s), 1.38(3H,m), 1.54–1.73(9H,m), 1.94(3H,s), 2.72(1H,t), 3.04(1H,dd), 3.85 (3H,s), 3.92(1H,d), 4.00(3H,m), 4.15(1H,d) 5.60(1H,d), 6.45(1H,bs), 6.65(1H,d), 6.88(2H,m), 7.20–7.30(6H,m).

The compound was further characterised and tested as the N-methyl-D-glucamine salt.

Found: C, 59.53; H, 7.28; N, 6.63. $C_{42}H_{58}N_4O_{12} \cdot 2H_2O$ requires C, 59.62; H 7.37; N, 6.62%

EXAMPLE 70

Preparation of (+/−)-trans-4-acetyl-3-(1-adamantyl)methyl-1-benzyl-5-carboxymethylaminocarbonyl-2,7-dioxo-9-methyl-2,3,4,5,6,7-hexahydro-1H-1,4-benzodiazonine The compound was prepared by an identical route to that used to prepare example 61 except that (R/S)-5-methyl-tryptophan benzyl ester was used in step a in place of (R/S)-5-fluoro-tryptophan benzyl ester (CDCl$_3$) $\delta_H$ 1.24(3H,s), 1.38(3H,m), 1.53–1.78(12H,m), 1.93(3H,s), 2.37(3H, s), 2.70(1H,t), 3.04(1H,m), 3.89–4.11 (5H,m), 5.60(1H,d), 6.50(1H,bs), 6.65(1H,d), 7.18–7.27 (7H,m).

The compound was further characterised and tested as the N-methyl-D-glucamine salt.

Found: C, 59.08; H, 6.92; N, 6.27. $C_{41}H_{55}ClN_4O_{11} \cdot H_2O$ requires C, 59.10; H 6.89; N, 6.72%

EXAMPLE 71

Preparation of (3R,5S)-4-acetyl-3-(1-adamantyl)methyl-1-(3-methylbenzyl)-5-carboxymethylaninocarbonyl-2,7-dioxo-2,3,4,5,6,7-hexahydro-1H-1,4-benzodiazonine The compound was prepared by an identical route to that used to prepare example 22 except that (3R,5S)-4-acetyl-3-

(1-adamantyl)methyl-1-(3-methylbenzyl)-2,7-dioxo-2,3,4,5,6,7-hexahydro-1H-1,4-benzodiazonine-5-carboxylate was used in step a in place of (3R,5S)-4-acetyl-3-(1-adamantyl)methyl-1-benzyl-2,7-dioxo-2,3,4,5,6,7-hexahydro-1H-1,4-benzodiazonine-5-carboxylate (CDCl$_3$) $\delta_H$ 1.11(3H,s), 1.29(3H,m), 1.49–1.67(9H,s), 1.88(3H,s), 2.23(3H,s), 2.63(1H,t), 2.97(1H,q), 3.78–4.04 (5H,m), 5.54(1H,d), 6.50(1H,bs), 6.72(1H,d), 6.91(1H,d), 7.00–7.12(3H,m), 7.27–7.42(4H,m).

The compound was further characterised and tested as the N-methyl-D-glucamine salt.

Found: C, 58.67; H, 7.39; N, 6.46. $C_{42}H_{58}N_4O_{11}.3.4H_2O$ requires C, 58.91; H 7.63; N, 6.54%

EXAMPLE 72

Preparation of (3R,5S)-4-acetyl-3-(1-adamantyl)methyl-1-(4-methylbenzyl)-5-carboxymethylaminocarbonyl-2,7-dioxo-2,3,4,5,6,7-hexahydro-1H-1,4-benzodiazonine The compound was prepared by an identical route to that used to prepare example 22 except that (3R,5S)-4-acetyl-3-(1-adamantyl)methyl-1-(4-methylbenzyl)-2,7-dioxo-2,3,4,5,6,7-hexahydro-1H-1,4-benzodiazonine-5-carboxylate was used in step a in place of (3R,5S)-4-acetyl-3-(1-adamantyl)methyl-1-benzyl-2,7-dioxo-2,3,4,5,6,7-hexahydro-1H-1,4-benzodiazonine-5-carboxylate (CDCl$_3$) $\delta_H$ 1.20(6H,m), 1.35–1.74(9H,m), 1.95(3H,s), 2.34(3H,s), 2.71(1H,t), 3.08(1H,dd), 3.92(1H,d), 4.02–4.09 (4H,m), 5.59(1H,d), 6.47(1H,bs), 6.78(1H,d), 7.07(3H,m), 7.16–7.27(2H,m), 7.36–7.46(4H,m).

The compound was further characterised and tested as the N-methyl-D-glucamine salt.

Found: C, 60.07; H, 7.59; N, 6.66. $C_{42}H_{58}N_{411}.2.5H_2O$ requires C, 60.06; H 7.56; N, 6.67%

EXAMPLE 73

Preparation of (3S,5R)-4-acetyl-3-(1-adamantyl)methyl-1-(2-fluorobenzyl)-5-carboxymethylaminocarbonyl-2,7-dioxo-2,3,4,5,6,7-hexahydro-1H-1,4-benzodiazonine The compound was prepared by an identical route to that used to prepare example 22 except that (3S,5R)-4-acetyl-3-(1-adamantyl)methyl-1-(2-fluorobenzyl)-2,7-dioxo-2,3,4,5,6,7-hexahydro-1H-1,4-benzodiazonine-5-carboxylate was used in step a in place of (3R,5S)-4-acetyl-3-(1-adamantyl)methyl-1-benzyl-2,7-dioxo-2,3,4,5,6,7-hexahydro-1H-1,4-benzodiazonine-5-carboxylate (CDCl$_3$) $\delta_H$ 1.21(4H,s), 1.20–1.74(12H,m), 1.95(3H,s), 2.34(3H,s), 2.69(1H,dd), 3.06(1H,dd), 3.90(1H,d), 4.02(5H, d), 5.57(1H,d), 6.77(1H,d), 7.10(5H,m), 7.40(2H,m).

EXAMPLE 74

Preparation of (3R,5S)-4-acetyl-3-(1-adamantyl)methyl-1-(2-methylbenzyl)-5-carboxymethylaminocarbonyl-2,7-dioxo-2,3,4,5,6,7-hexahydro-1H-1,4-benzodiazonine The compound was prepared by an identical route to that used to prepare example 22 except that (3R,5S)-4-acetyl-3-(1-adamantyl)methyl-1-(2-methylbenzyl)-2,7-dioxo-2,3,4,5,6,7-hexahydro-1H-1,4-benzodiazonine-5-carboxylate was used in step a in place of (3R,5S)-4-acetyl-3-(1-adamantyl)methyl-1-benzyl-2,7-dioxo-2,3,4,5,6,7-hexahydro-1H-1,4-benzodiazonine-5-carboxylate (CDCl$_3$) $\delta_H$ 1.20(3H,s), 1.15–1.30(4H,m), 1.43–1.69 (10H,m), 1.87(3H,s), 2.60(1H,t), 2.64(1H,t), 3.10(1H,m), 3.97(2H,m), 4.05(3H,m), 4.20(1H,d), 5.41(1H, d), 6.47(1H, bs), 7.06(3H,m), 7.24–7.46(6H,m).

EXAMPLE 75

Preparation of (3R,5S)-4-acetyl-3-(1-adamantyl)methyl-1-(4-methoxybenzyl)-5-carboxymethylaminocarbonyl-2,7-dioxo-2,3,4,5,6,7-hexahydro-1H-1,4-benzodiazonine The compound was prepared by an identical route to that used to prepare example 22 except that (3R,5S)-4-acetyl-3-(1-adamantyl)methyl-1-(4-methoxybenzyl)-2,7-dioxo-2,3,4,5,6,7-hexahydro-1H-1,4-benzodiazonine-5-carboxylate was used in step a in place of (3R,5S)-4-acetyl-3-(1-adamantyl)methyl-1-benzyl-2,7-dioxo-2,3,4,5,6,7-hexahydro-1H-1,4-benzodiazonine-5-carboxylate (CDCl$_3$) $\delta_H$ 1.17(3H,s), 1.20–1.37(6H,m), 1.53–1.68(9H, m), 1.94(3H,s), 2.70(1H,t), 3.00(1H,q), 3.35–3.41(3H,m), 3.80(3H,s), 3.93–4.04(3H,m),5.53(1H,d), 6.55(1H,t), 6.73–6.81(3H,m), 7.03–7.13(2H,m), 7.40–7.48(2H,m).

The compound was further characterised and tested as the N-methyl-D-glucamine salt.

Found: C, 60.46; H, 7.64; N, 6.92. $C_{42}H_{58}N_4O_{11}.2H_2O$ requires C, 60.64; H 7.52; N, 6.73%

The compounds of the examples were tested for binding at the CCK$_B$ receptor in mouse cortical membranes by means of a radioligand binding assay. The procedure was as follows:

The whole brains from male mice (CD1 22–25 g; Charles River) were removed and placed in ice-cold buffer (pH7.2@21±3° C.) of the following composition (mM); 10 HEPES, 130 NaCl, 4.7 KCl, 5 MgCl$_2$, 1 EDTA and containing 0.25 g.l$^{-1}$ bacitracin. The cortex was dissected, weighed and homogenised in 40 ml ice-cold buffer using a Teflon-in-glass homogeniser. The homogenate was centrifuged at 39,800 g for 20 min at 4° C., the supernatant discarded and the pellet resuspended by homogenisation in fresh buffer. The homogenate was recentrifuged (39,800 g; 20 min @4° C.) and the final pellet was resuspended in HEPES buffer to give a tissue concentration of 2 mg.ml$^{-1}$ (original wet weight).

The membranes (400 $\mu$l) were incubated for 150 min at 21±3° C. in a final volume of 0.5 ml with HEPES buffer containing [$^{125}$I]-CCK8S (0.05 ml; 200 pM NEN 2200 Ci.mmol$^{-1}$) and competing compound. Total and non-specific binding of [$^{125}$I]-CCK8S were defined using 0.05 ml of buffer and 0.05 ml of 10 mM L-365,260, respectively. The assay was terminated by rapid filtration through pre-soaked Whatman GF/B filters using a Brandell Cell harvester. The filters were washed (3×3 ml) with ice-cold 50 mM Tris-HCl (pH7.4@4° C.) and bound radioactivity determined by counting (1 min.) in a gamma-counter.

The compounds of the examples were also tested in a CCK$_A$ binding assay as follows:

The pancreatata were removed from male guinea-pigs (200–300 g; Dunkin Hartley) and placed in ice-cold HEPES buffer (pH 7.2@21±3° C.). The pancreatata were homogenised in 40 ml ice-cold HEPES buffer using a polytron (Brinkmann, PT10, setting 10) 4×1 second. The homogenate was centrifuged at 39,800 g for 15 min at 4° C. The supernatant was discarded and the pellet re-suspended using a Teflon-in-glass homogeniser in 20 volumes of fresh buffer and re-centrifuged as above. The final pellet was re-suspended using a Teflon-in-glass homogeniser to a tissue concentration of 1 mg.ml$^{-1}$ (original wet weight), and filtered through 500 μm pore-size Nytex mesh.

The membranes (400 μl; containing 0.375 μM PD134, 308) were incubated for 150 minutes at 21±3° C. in a final volume of 0.5 ml with HEPES buffer containing [$^{125}$I]-CCK$_8$(S) (50 μl; 200 pM) and competing compound. Total and non-specific binding of [$^{125}$I]-CCK$_8$(S) were defined using 50 μl of buffer and 50 μl of 100 nM L-364,718 respectively. The assay was terminated by rapid filtration through pre-soaked Whatman GF/B filters using a Brandell Cell Harvester. The filters were washed (3×3 ml) with ice-cold 50 mM Tris HCl (pH 7.4 at 4° C.) and bound radioactivity was determined by counting (1 min) in a gamma counter.

TABLE 1

| Example | pK$_i$ (Mouse cortex) | pK$_i$ (Guinea pig pancreas) |
|---|---|---|
| 1 | 5.0 | 6.7 |
| 2 | 5.9 | 7.3 |
| 3 | 5.1 | 6.5 |
| 4 | 5.0 | 5.5 |
| 5 | 5.0 | 5.3 |
| 6 | 5.0 | 5.3 |
| 7 | 5.0 | 5.8 |
| 8 | 5.0 | 6.0 |
| 9 | 5.4 | 6.5 |
| 10 | 5.6 | 6.5 |
| 11 | 6.0 | 5.3 |
| 12 | 5.0 | 5.0 |
| 13 | 5.6 | 5.5 |
| 14 | 5.6 | 5.5 |
| 15 | 5.9 | 5.8 |
| 16 | 5.8 | 5.7 |
| 17 | 5.9 | 5.2 |
| 18 | 5.5 | 5.4 |
| 19 | 5.1 | 4.8 |
| 20 | 5.5 | 5.4 |
| 21 | 5.1 | 5.2 |
| 22 | 6.7 | 5.0 |
| 23 | 6.0 | 5.0 |
| 24 | 6.9 | 5.0 |
| 25 | 6.4 | 5.2 |
| 26 | 6.0 | 5.2 |
| 27 | 5.0 | 5.0 |
| 28 | 5.4 | 4.6 |
| 29 | 5.5 | 5.2 |
| 30 | 5.0 | 5.1 |
| 31 | 5.8 | 5.2 |
| 32 | 5.3 | 5.0 |
| 33 | 5.0 | 5.2 |
| 34 | 5.4 | 5.6 |
| 35 | 5.6 | 5.1 |
| 36 | 5.5 | 5.3 |
| 37 | 5.8 | 5.2 |
| 38 | 5.3 | 5.0 |
| 39 | 5.6 | 5.0 |
| 40 | 5.4 | 4.7 |
| 41 | 6.4 | 5.0 |
| 42 | 4.7 | 5.0 |
| 43 | 4.8 | 5.0 |
| 44 | 5.5 | 6.8 |
| 45 | 5.0 | 7.1 |
| 46 | 5.0 | 5.4 |
| 47 | 5.2 | |
| 48 | 4.8 | |
| 49 | 5.2 | |
| 50 | 5.8 | 5.9 |
| 51 | 5.5 | 6.1 |
| 52 | 5.0 | 6.7 |
| 53 | | 6.2 |
| 54 | 5.4 | |
| 55 | 5.0 | 6.0 |
| 58 | 5.7 | 5.1 |
| 59 | 7.0 | 5.0 |
| 60 | 6.7 | 5.0 |

TABLE 1-continued

| Example | pK$_i$ (Mouse cortex) | pK$_i$ (Guinea pig pancreas) |
|---|---|---|
| 61 | 6.4 | 4.9 |
| 62 | 6.4 | |
| 63 | 7.0 | 5.0 |
| 64 | 6.8 | 4.6 |
| 65 | 6.4 | |
| 66 | 6.3 | |
| 67 | 6.8 | |
| 68 | 6.8 | |
| 69 | 6.9 | |
| 70 | 6.9 | |
| 71 | 6.0 | |
| 72 | 6.2 | |
| 73 | 5.6 | |
| 74 | 6.8 | |
| 75 | 5.9 | |

We claim:
1. A compound of the formula

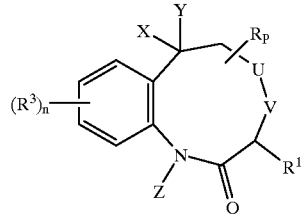

(I)

wherein one of U and V is —CHR$^2$—, and the other of U and V is selected from the group consisting of —N(COR$^4$)—, —CH(COR$^4$)—, —N(SO$_2$R$^4$)— and —CH(SO$_2$R$^4$)—, in which:

R$^2$ is H, —COOR$^5$ wherein R$^5$ is H or C$_1$ to C$_4$ hydrocarbyl, —CONR$^6$R$^7$ wherein R$^6$ is H or methyl and R$^7$ is aryl, substituted aryl, or a group of the formula —(C$_1$ to C$_4$)alkylene-W, in which W is amidino, hydroxy, acyloxy, sulphamoyl, hydroxysulphonyl, carboxy, esterified carboxy, amidated carboxy, tetrazolyl, hydroxamyl, R$^{14}$—SO$_2$—NH—, R$^{14}$—SO$_2$—NH—CO—, R$^{14}$—SO$_2$—, R$^{14}$—SO—, R$^{14}$—CO—, R$^{14}$—CO—NH—, R$^{14}$—CO—NH—SO—, R$^{14}$—CO—NH—SO$_2$—, or R$^{15}$—NH—SO$_2$— wherein R$^{14}$ is selected from the group consisting of H, C$_1$ to C$_6$ alkyl, C$_1$ to C$_6$ haloalkyl, aryl and substituted aryl, except that R$^{14}$ may not be H when attached to a sulphur atom, and R$^{15}$ is H, C$_1$ to C$_6$ alkyl, C$_1$ to C$_6$ haloalkyl, aryl, substituted aryl, —OH or —CN; or R$^6$ and R$^7$ together form a carboxy-substituted propylene, butylene or pentylene group or —COR$^7$; and R$^4$ is H, C$_1$ to C$_6$ hydrocarbyl in which up to three of the carbon atoms may be replaced by a nitrogen, oxygen or sulphur atom, provided that R$^4$ does not contain a —O—O— group, or R$^4$ is a group of the formula —Q—R$^{16}$ wherein Q is selected from the group consisting of a bond, —NR$^7$— in which R$^{17}$ is H or C$_1$ to C$_3$ alkyl and —O—, and R$^{16}$ is aryl, substituted aryl, arylalkyl or (substituted aryl)alkyl;

R is independently C$_1$ to C$_3$ alkyl,

R$^1$ is H or C$_1$ to C$_{15}$ hydrocarbyl wherein one or more hydrogen atoms may be replaced by halogen atoms, and one carbon atom may be replaced by a nitrogen, oxygen or sulphur atom;

R$^3$ is independently halo, alkyl, —NO$_2$, —NH$_2$ or —NHCOR$^5$;

X is H, and Y is H or $C_1$ to $C_{10}$ hydrocarbyl wherein one or more hydrogen atoms may be replaced by halogen atoms, and one carbon atom may be replaced by a nitrogen, oxygen or sulphur atom; or X and Y together are =O or =$CH_2$;

Z is: H; $C_1$ to $C_{15}$ hydrocarbyl, in which one or more hydrogen atoms may be replaced by a halogen atom, and up to three of the carbon atoms may be replaced by a nitrogen, oxygen or sulphur atom, provided that Z does not contain a —O—O— group; or —$(CHR^{18})_m$—$R^8$, wherein $R^{18}$ is H or $C_1$ to $C_3$ alkyl and $R^8$ is phenyl, substituted phenyl or a group of the formula —$COOR^9$ or —$CONR^9R^{10}$, in which $R^9$ and $R^{10}$ are independently H or $C_1$ to $C_6$ alkyl, or $R^9$ and $R^{10}$ together form a propylene, butylene, pentylene or hexylene group; m is 1, 2 or 3; and n and p are independently from 0, 1, 2, or 3, or a pharmaceutically acceptable salt thereof.

2. A compound according to claim 1 in which U is —$CHR^2$— and V is —$N(COR^4)$—.

3. A compound according to claim 1, wherein $R^1$ is H, $C_1$ to $C_6$alkyl- or cycloalkyl-($C_1$ to $C_6$)alkyl.

4. A compound according to claim 3 wherein $R^1$ is t-butyl or (1-adamantyl)methyl.

5. A compound according to claim 1, wherein $R^4$ is selected from the group consisting of H, methyl, methoxy, carboxymethyl, carboxyethyl, benzyloxy and a group of the formula —NH—Ar, wherein Ar is an aromatic group selected from the group consisting of methylphenyl, carboxyphenyl, dicarboxyphenyl, dichlorophenyl, naphthyl and indolyl.

6. A compound according to claim 1, wherein $R^8$ is selected from the group consisting of t-butyloxycarbonyl, ethoxycarbonyl, pyrrolidinyl, phenyl, 3-methoxyphenyl, 4-methoxyphenyl, 3-chlorophenyl, 4-chlorophenyl and 3-aminophenyl.

7. A compound according to claim 1, wherein X and Y together form a =O group.

8. A compound according to claim 1, wherein n is 0.

9. A compound according to claim 1, wherein p is 0.

10. A pharmaceutical composition comprising a compound according to claim 1, together with a pharmaceutically acceptable excipient or carrier.

11. A method of preparing a compound according to claim 1, comprising the step of oxidising a compound of the formula

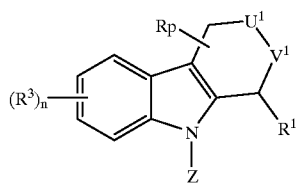

wherein $U^1$ and $V^1$ are U and V, respectively, or protected derivatives thereof, with an oxidant to form a compound of the formula

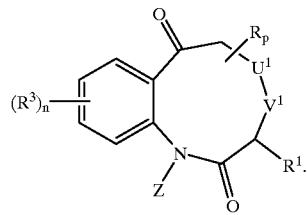

12. A method of preparing a compound according to claim 1, in which X is H and Y is —OH, said method comprising reducing a compound of the formula

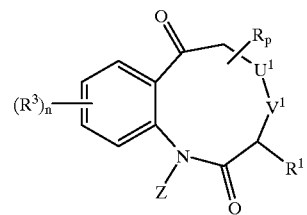

wherein $U^1$ and $V^1$ are U and V, respectively, or protected derivatives thereof.

13. A method of preparing a compound according to claim 1, in which X is H and Y is —$CH_3$, said method comprising reducing a compound of the formula

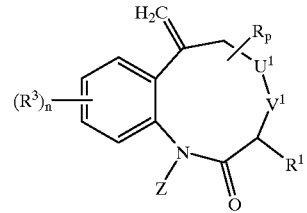

wherein $U^1$ and $V^1$ are U and V, respectively, or suitably protected derivatives thereof.

14. A method of preparing a compound according to formula I above, said method comprising the step of reacting a compound of the formula

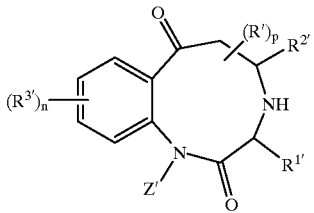

or

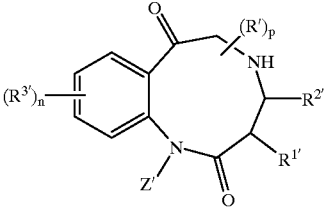

with an isocyanate of the formula $R^{16}$NCO or a carboxylic acid of the formula $R^1COOH$, wherein $R^{1'}$, $R^{2'}$, $R^{3'}$, R', and Z' are $R^1$, $R^2$, $R^3$, R, and Z, respectively, or protected derivatives thereof, and $U^1$ and $V^1$ are U and V, respectively, or suitably protected derivatives thereof.

15. A method of preparing a compound according to claim 1, said method comprising the step of ring closure of a compound of the formula

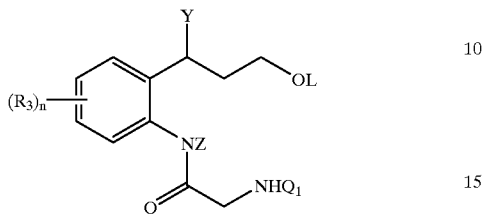

with a base, wherein $Q^1$ is H or a protecting group, and OL is a suitable leaving group.

16. A method of lowering gastrin or cholecystokinin activity in a patient, comprising administering to said patient an effective amount of a compound according to claim 1.

17. A method of preparing a compound according to claim 1, wherein X and Y together form a methylene group, said method comprising the step of reacting a compound of formula

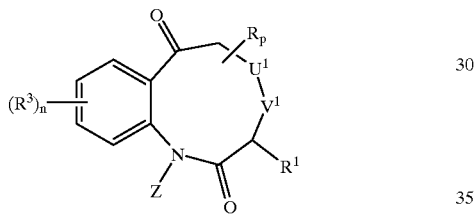

wherein $U^1$ and $V^1$ represent any of the groups recited in claim 1 for U and V, respectively, or protected derivatives thereof, with μ-chloro-μ-methylene-{bis(cyclopentadienyl) titanium}- dimethylaluminium.

18. A compound of the formula

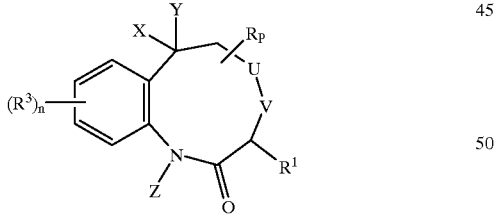

(I)

wherein U is —$CHR^2$—,

V is selected from the group consisting of —$N(COR^4)$—, —$CH(COR^4)$—, —$N(SO_2R^4)$— and —$CH(SO_2R^4)$—, in which:

$R^2$ is H, —$COOR^5$ wherein $R^5$ is H or $C_1$ to $C_4$ hydrocarbyl, —$CONR^6R^7$ wherein $R^6$ is H or methyl and $R^7$ is aryl, substituted aryl, or a group of the formula —($C_1$ to $C_4$)alkylene-W, in which W is amidino, hydroxy, acyloxy, sulphamoyl, hydroxysulphonyl, carboxy, esterified carboxy, amidated carboxy, tetrazolyl, hydroxamyl, $R^{14}$—$SO_2$—NH—, $R^{14}$—$SO_2$—NH—CO—, $R^{14}$—$SO_2$—, $R^{14}$—SO—, $R^{14}$—CO—, $R^{14}$—CO—NH—, $R^{14}$—CO—NH—SO—, $R^{14}$—CO—NH—$SO_2$—, or $R^{15}$—NH—$SO_2$— wherein $R^{14}$ is selected from the group consisting of H, $C_1$ to $C_6$ alkyl, $C_1$ to $C_6$ haloalkyl, aryl and substituted aryl, except that $R^{14}$ may not be H when attached to a sulphur atom, and $R^{15}$ is H, $C_1$ to $C_6$ alkyl, $C_1$ to $C_6$ haloalkyl, aryl, substituted aryl, —OH or —CN; or $R^6$ and $R^7$ together form a carboxy-substituted propylene, butylene or pentylene group or —$COR^7$; and $R^4$ is H, $C_1$ to $C_6$ hydrocarbyl in which up to three of the carbon atoms may be replaced by a nitrogen, oxygen or sulphur atom, provided that $R^4$ does not contain a —O— group, or $R^4$ is a group of the formula —Q—$R^{16}$ wherein Q is selected from the group consisting of a bond, —$NR^7$— in which $R^{17}$ is H or $C_1$ to $C_3$ alkyl and —O—, and $R^{16}$ is aryl, substituted aryl, arylalkyl or (substituted aryl)alkyl;

R is independently $C_1$ to $C_3$ alkyl, $R^1$ is H or $C_1$ to $C_{15}$ hydrocarbyl wherein one or more hydrogen atoms may be replaced by halogen atoms, and one carbon atom may be replaced by a nitrogen, oxygen or sulphur atom;

$R^3$ is independently halo, alkyl, alkoxy, —$NO_2$, —$NH_2$ or —$NHCOR^5$;

X is H, and Y is H or $C_1$ to $C_{10}$ hydrocarbyl wherein one or more hydrogen atoms may be replaced by halogen atoms, and one carbon atom may be replaced by a nitrogen, oxygen or sulphur atom; or X and Y together are =O or =$CH_2$;

Z is: H; $C_1$ to $C_{15}$ hydrocarbyl, in which one or more hydrogen atoms may be replaced by a halogen atom, and up to three of the carbon atoms may be replaced by a nitrogen, oxygen or sulphur atom, provided that Z does not contain a —O—O— group; or —$(CHR^{18})_m$—$R^8$, wherein $R^{18}$ is H or $C_1$ to $C_3$ alkyl and $R^8$ is phenyl, substituted phenyl or a group of the formula —$COOR^9$ or —$CONR^9R^{10}$, in which $R^9$ and $R^{10}$ are independently H or $C_1$ to $C_6$ alkyl, or $R^9$ and $R^{10}$ together form a propylene, butylene, pentylene or hexylene group;

m is 1, 2 or 3; and n and p are independently from 0, 1, 2, or 3, or a pharmaceutically acceptable salt thereof.

19. A compound according to claim 18, wherein V is —$N(COR^4)$—.

20. A compound according to claim 18, wherein $R^1$ is H, $C_1$ to $C_6$ alkyl- or cycloalkyl-($C_1$ to $C_6$)alkyl-.

21. A compound according to claim 20, wherein $R^1$ is t-butyl or (1-adamantyl)methyl.

22. A compound according to claim 18, wherein $R^4$ is selected from the group consisting of H, methyl, methoxy, carboxymethyl, carboxyethyl, benzyloxy and a group of the formula —NH—Ar, wherein Ar is an aromatic group selected from the group consisting of methylphenyl, carboxyphenyl, dicarboxyphenyl, dichlorophenyl, naphthyl and indolyl.

23. A compound according to claim 18, wherein $R^8$ is selected from the group consisting of t-butyloxycarbonyl, ethoxycarbonyl, pyrrolidinyl, phenyl, 3-methoxyphenyl, 4-methoxyphenyl, 3-chlorophenyl, 4-chlorophenyl and 3-aminophenyl.

24. A compound according to claim 18, wherein X and Y together form a =O group.

25. A compound according to claim 18, wherein n is 0.

26. A compound according to claim 18, wherein p is 0.

27. A pharmaceutical composition comprising a compound according to claim 18, together with a pharmaceutically acceptable excipient or carrier.

28. A method of preparing a compound according to claim 18, comprising the step of oxidising a compound of the formula

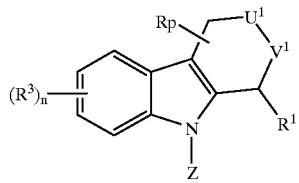

wherein $U^1$ and $V^1$ are U and V, respectively, or protected derivatives thereof with an oxidant to form a compound of the formula

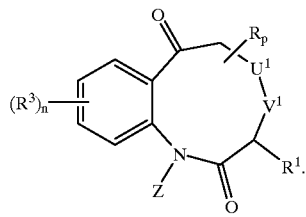

29. A method of preparing a compound according to claim 18, in which X is H and Y is —OH, said method comprising reducing a compound of the formula

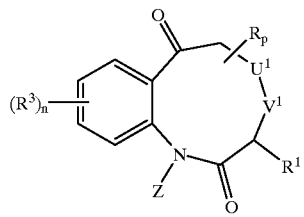

wherein $U^1$ and $V^1$ and U and V, respectively, or protected derivatives thereof.

30. A method of preparing a compound according to claim 18, in which X is H and Y is —CH$_3$, said method comprising reducing a compound of the formula

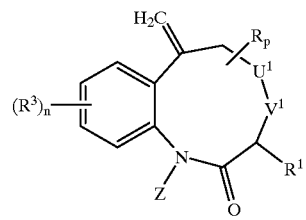

wherein $U^1$ and $V^1$ are U and V, respectively, or protected derivatives thereof.

31. A method of preparing a compound according to claim 18, said method comprising the step of reacting a compound of the formula

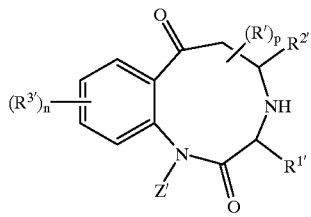

or

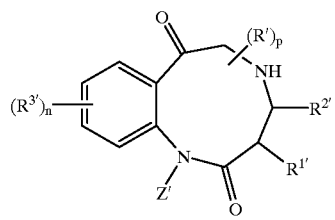

with an isocyanate of the formula $R^{16}NCO$ or a carboxylic acid of the formula $R^1COOH$, wherein $R^{1'}$, $R^{2'}$, $R^{3'}$, R', and Z' are $R^1$, $R^2$, $R^3$, R, and Z, respectively, or protected derivatives thereof, and $U^1$ and $V^1$ are U and V, respectively, or suitably protected derivatives thereof.

32. A method of preparing a compound according to claim 18, said method comprising the step of ring closure of a compound of the formula

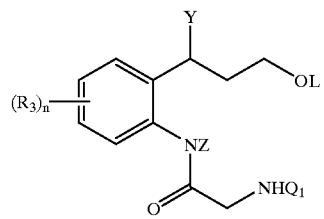

with a base, wherein $Q^1$ is H or a protecting group, and OL is a leaving group.

33. A method of treating a patient suffering from a condition in which lowered gastrin or cholecystokinin activity is desirable, comprising administering to said patient an effective amount of a compound according to claim 18.

34. A method of preparing a compound according to claim 18, wherein X and Y together form a methylene group, said method comprising the step of reacting a compound of formula

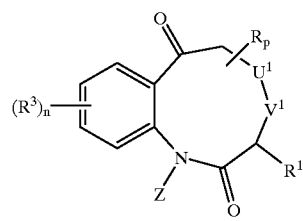

wherein $U^1$ and $V^1$ represents any of the groups recited in claim 18 for U and V, respectively, or protected derivatives thereof, with $\mu$-chloro-$\mu$-methylene-{bis(cyclopentadienyl)titanium}-dimethylaluminium.

* * * * *